US008722643B2

(12) United States Patent
Donald

(10) Patent No.: US 8,722,643 B2
(45) Date of Patent: *May 13, 2014

(54) TARGETING EN2, PAX2, AND/OR DEFB1 FOR TREATMENT OF PROSTATE CONDITIONS

(71) Applicant: Phigenix, Inc., Atlanta, GA (US)

(72) Inventor: Carlton D. Donald, Atlanta, GA (US)

(73) Assignee: Phigenix, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/912,841

(22) Filed: Jun. 7, 2013

(65) Prior Publication Data

US 2013/0296403 A1 Nov. 7, 2013

Related U.S. Application Data

(63) Continuation of application No. 13/310,940, filed on Dec. 5, 2011, now Pat. No. 8,461,126, which is a continuation-in-part of application No. 12/708,294, filed on Feb. 18, 2010, now Pat. No. 8,080,534, which is a continuation-in-part of application No. 12/090,191, filed as application No. PCT/US2006/040215 on Oct. 16, 2006, now Pat. No. 7,964,577.

(60) Provisional application No. 60/726,921, filed on Oct. 14, 2005.

(51) Int. Cl.
*C12N 15/113* (2010.01)
*C07H 21/04* (2006.01)

(52) U.S. Cl.
CPC .............. *C12H 15/113* (2013.01); *C07H 21/04* (2013.01)
USPC ........................................ 514/44 A; 536/24.5

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,585,481 A | 12/1996 | Arnold et al. | |
| 2003/0235874 A1 | 12/2003 | Kao et al. | |
| 2006/0223141 A1 | 10/2006 | Carey et al. | |
| 2008/0081791 A1 | 4/2008 | Huang et al. | |
| 2008/0247996 A1 | 10/2008 | Yu et al. | |
| 2009/0130061 A1 | 5/2009 | Yu et al. | |
| 2010/0029560 A1 | 2/2010 | Donald | |
| 2010/0093558 A1 | 4/2010 | Pandha et al. | |
| 2010/0196450 A1 | 8/2010 | Donald | |
| 2010/0209421 A1 | 8/2010 | Donald | |

OTHER PUBLICATIONS

Bensch et al., "hBD-I: a novel β-defensin from human plasma", FEBS Letters, vol. 368, pp. 331-335 (1995).

Bose et al., "Oncogenic Role of Engrailed-2 (En-2) in Prostate Cancer Cell Growth and Survival", Translational Oncogenomics, vol. 3 pp. 37-43 (2008).

Dressler et al., "Pax2, a new murine paired-box-containing gene and its expression in the developing excretory system", Development, vol. 109, pp. 787-795 (1990).

Furic et al., "eIF4E phosphorylation promotes tumorigenesis and is associated with prostate cancer progression", PNAS, vol. 107, No. 32, pp. 14134-14139 (2010).

Gibson et al., "Inhibition of PAX2 expression results in alternate cell death pathways in prostate cancer cells differing in p53 status", vol. 248, Issue 2, pp. 251-261 (2007).

Graff et al., "Targeting the Eukaryotic Translation Initiation Factor 4E for Cancer Therapy", Cancer Res, vol. 68, Issue 3, pp. 631-634 (2008).

Harder et al., "Mapping of the Gene Encoding Human β-Defensin-2 (DEFB2) to Chromosome Region 8p22-p23.1", Genomics, vol. 46, Issue 3, pp. 472-475 (1997).

Harder et al., "Isolation and Characterization of Human β-Defensin-3, a Novel Human Inducible Peptide Antibiotic", The Journal of Biological Chemistry, vol. 276, No. 8, pp. 5707-5713 (2001).

Jia et al., "Discovery of new human β-defensins using a genomics-based approach", Gene, vol. 263, Issue 1-2, pp. 211-218 (2001).

Joyner et al., "Engrailed, Wnt and Pax genes regulate midbrain—hindbrain development", Trends in Genetics, vol. 12, Issue 1, pp. 15-20 (1996).

Koenig et al., "En2, Pax2/5 and Tcf-4 transcription factors cooperate in patterning the *Xenopus* brain", Developmental Biology, vol. 340, pp. 318-328 (2010).

Kozmik et al., "Deregulated expression of PAX5 in medulloblastoma", Proc. Natl. Acad. Sci. USA, vol. 92 pp. 5709-5713 (1995).

Martin et al., "EN2 is a candidate oncogene in human breast cancer", Oncogene, vol. 24, pp. 6890-6901 (2005).

Zhou et al., "Aptamer-targeted cell-specific RNA interference", Silence, vol. 1, Issue 4, pp. 1-10 (2010).

Papo et al., "A Molecular Mechanism for Lipopolysaccharide Protection of Gram-negative Bacteria from Antimicrobial Peptides", J. Biol. Chem., vol. 280, pp. 10378-10387 (2005).

Stuart et al., "Mammalian Pax Genes", Annual Review of Genetics, vol. 28, pp. 219-238 (1994).

(Continued)

*Primary Examiner* — Tracy Vivlemore

(74) *Attorney, Agent, or Firm* — Ping Wang; Andrews Kurth LLP

(57) ABSTRACT

The present invention relates to methods and compositions for treating a prostate condition in a subject. The method comprises administering to the subject a subject effective amount of a pharmaceutical composition having a first agent that inhibits EN2 expression and/or EN2 activity and a second agent that inhibits PAX2 expression and/or PAX2 activity. The pharmaceutical composition may further comprise a third agent that enhances DEFB1 expression or activity.

13 Claims, 42 Drawing Sheets

(5 of 42 Drawing Sheet(s) Filed in Color)

(56) References Cited

OTHER PUBLICATIONS

Ganz et al., "Antimicrobial peptides of phagocytes and epithelia", Semin Hematol. vol. 34, Issue 4, pp. 343-354 (1997). (abstract only).

Nagel et al., "Activation of HLXB9 by juxtaposition with MYB via formation of t(6;7)(q23;q36) in an AML-M4 cell line (GDM-1)" Genes Chromosomes Cancer, vol. 42, Issue 2, pp. 170-178 (2005). (abstract only).

Bose et al., "PAX2 oncogene negatively regulates the expression of the host defense peptide human beta defensin-1 in prostate cancer", Mol. Immunol. vol. 46, Issue 6, pp. 1140-1148 (2009).

Chen et al., "Synthesis of oligodeoxyribonucleotide N3'-+P5' phosphoramidates", Nucl. Acids. Res., vol. 23, Issue 14, pp. 2661-2668 (1995).

Chen et al., "Antitumor effect of dsRNA-induced p21WAF1/CIP1 gene activation in human bladder cancer cells", Mol. Cancer Ther., vol. 7, Issue 3, pp. 698-703 (2008).

Chu et al., "Aptamer mediated siRNA delivery", Nucl. Acids. Res., vol. 34, Issue 10, pp. 1-6 (2006).

Dassie et al., "Systemic administration of optimized aptamer-siRNA chimeras promotes regression of PSMA-expressing tumors", Nat Biotech., vol. 27, Issue 9, pp. 839-846 (2009). (abstract only).

Gann et al., "A Prospective Evaluation of Plasma Prostate-Specific Antigen for Detection of Prostatic Cancer", JAMA, vol. 273, Issue 4, pp. 289-294 (1995). (abstract only).

Ge et al, "Zarro locked nucleic acid induces sequence-specific gene silencing", FASEB J., vol. 21, No. 8, pp. 1902-1914 (2007).

Heitz et al., "Twenty years of cell-penetrating peptides: from molecular mechanisms to therapeutics", Br. J. Pharmacol., vol. 157, Issue 2, pp. 195-206 (2009).

Joliet, "Transduction peptides: from technology to physiology", Nature Cell Biol., vol. 6, Issue 3, pp. 189-196 (2004).

Kraaij et al., "A small chimeric promoter for high prostate-specific transgene expression from adenoviral vectors", Prostate, vol. 67, Issue 8, pp. 829-839 (2007). (abstract only).

Li et al., "Small dsRNAs induce transcriptional activation in human cells", Proc., Natl. Acad. Sci. USA, vol. 103, Issue 46, pp. 17337-17342 (2006).

McNamara et al., "Cell type-specific delivery of siRNAs with aptamer-siRNA chimeras", Nat. Biotech., vol. 24, Issue 8, pp. 1005-1015 (2000).

Meade et al.,"Enhancing the cellular uptake of siRNA duplexes following noncovalent packaging with protein transduction domain peptides", Adv. Drug Deliv., vol. 60, Issue 4-5, pp. 530-536 (2008).

Morris et al., "A peptide carrier for the delivery of biologically active proteins into mammalian cells", Nat. D Biotechnol., vol. 19, Issue. 12, pp. 1173-1176 (2001 ).

Nielsen et al., "An Introduction to Peptide Nucleic Acid", Curr. Issues Mol. Biol., vol. 1, Issue 2, pp. 89-104 (1999).

Ray et al, "Peptide nucleic acid (PNA): its medical and biotechnical applications and promise for the future", FASEB J., vol. 14, pp. 1041-1060 (2000).

Ray et al., "Aptamers for Targeted Drug Delivery", Pharmaceuticals, vol. 3, pp. 1761-1778 (2010).

Reynolds et al.,"Synthesis and Thermodynamics of Oligonucleotides Containing Chirally Pure RP Methylphosphonate Linkages", Nucl. Acids Res., vol. 24, Issue 22, pp. 4584-4591 (1996).

Sato et al., "Configurations of a two-tiered amplified gene expression system in adenoviral vectors designed to improve the specificity of in vivo prostate cancer imaging", Gene. Ther., vol. 15, Issue 8, pp. 583-593 (2008).

Trujillo et al., "A probasin promoter, conditionally replicating adenovirus that expresses the sodium iodide symporter (NIS) for radiovirotherapy of prostate cancer", Gene. Ther., vol. 17, Issue 11, pp. 1325-1332 (2010).

Veedu, et al., "Locked nucleic acid as a novel class of therapeutic agents", RNA Biol., vol. 6, Issue3, pp. 321-323 (2009).

Zaghloul et al., "Optimizing anti-gene oligonucleotide 'Zorro-LNA' for improved strand invasion into duplex DNA", Nucl. Acids. Res., vol. 39, Issue 3, pp. 1142-1154 (2011).

Zhang et al., "Down-modulation of cancer targets using locked nucleic acid (LNA)-based antisense oligonucleotides without transfection", Gene Ther., vol. 18, pp. 326-333 (2011 ).

International Search Report and Written Opinion of the International Searching Authority of International Patent Application No. PCT/US2011/063298, mailed Aug. 7, 2012.

U.S. Appl. No. 13/310,940, filed Dec. 5, 2011.

U.S. Appl. No. 12/090,191, filed Sep. 15, 2008.

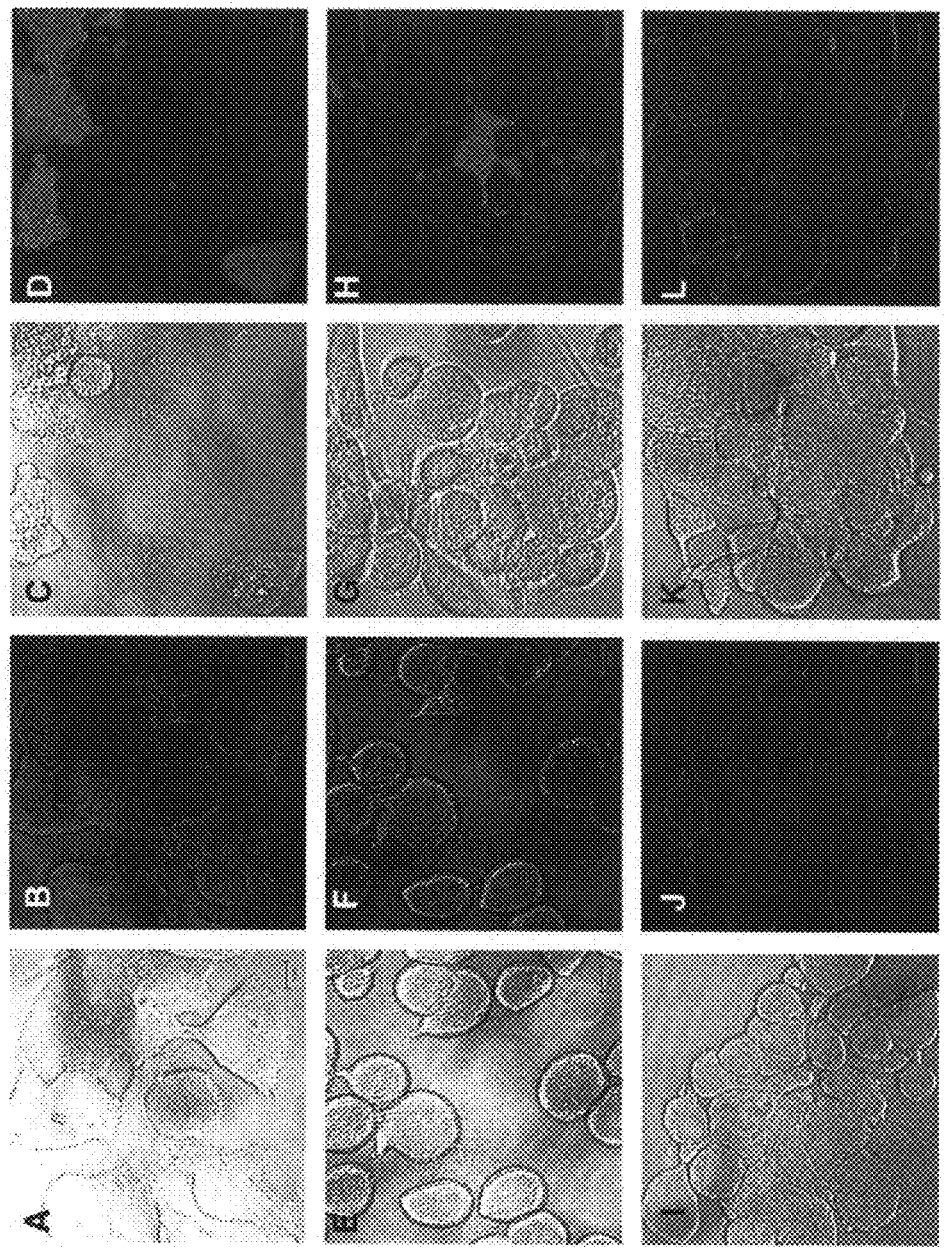
FIG. 5A-L

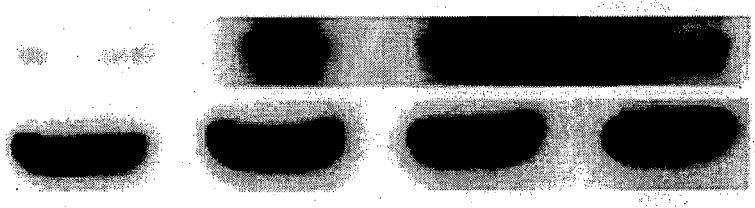
FIG. 36A
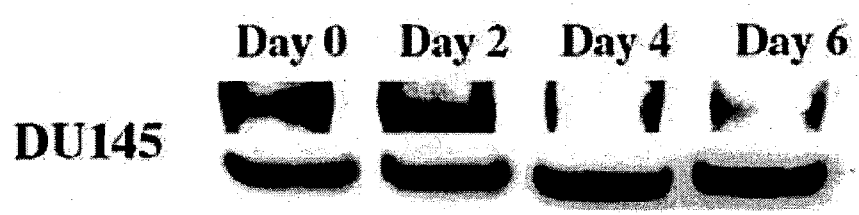
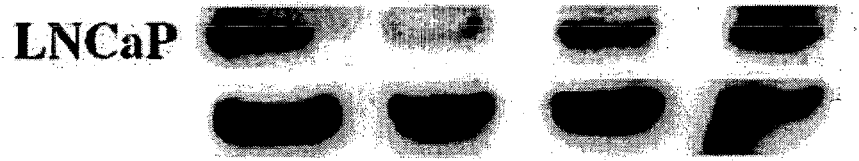
FIG. 36B

US 8,722,643 B2

TARGETING EN2, PAX2, AND/OR DEFB1 FOR TREATMENT OF PROSTATE CONDITIONS

This application is a continuation of U.S. application Ser. No. 13/310,940, filed Dec. 5, 2011, now allowed, which is a continuation-in-part of U.S. application Ser. No. 12/708,294, filed Feb. 18, 2010, now U.S. Pat. No. 8,080,534, which is a continuation-in-part of U.S. patent application Ser. No. 12/090,191, filed on Sep. 15, 2008, now U.S. Pat. No. 7,964,577, as the national entry of PCT Application No. PCT/US2006/040215, filed on Oct. 16, 2006, which claims priority to U.S. Patent Application No. 60/726,921, filed on Oct. 14, 2005. The entirety of all of the aforementioned applications is incorporated herein by reference.

FIELD

This application relates generally to the field of cancer, and, in particular, to compositions and methods for the treatment of prostate conditions.

BACKGROUND

Cancer is a collective term for various forms of malignant cell growth and is one of the leading causes of human deaths worldwide. Healthy cells control their own growth and will destroy themselves if they become unhealthy, while cancer cells divide and grow uncontrollably and invade nearby parts of the body. Cell division is a complex process that is normally tightly regulated. Cancer happens when problems in the genes in a cell prevent these controls from working. These problems with genes may be from damage to the gene or may be inherited. Damage to genes can come from many sources inside or outside of the cell. Faults in two types of genes are especially important: oncogenes, which drive the growth of cancer cells, and tumor suppressor genes, which prevent cancer from developing.

Cancer can be detected in a number of ways, including the presence of certain signs and symptoms, screening tests, or medical imaging. Once a possible cancer is detected it is diagnosed by microscopic examination of a tissue sample. Cancer is usually treated with chemotherapy, radiation therapy and surgery. The chances of surviving the disease vary greatly by the type and location of the cancer and the extent of disease at the start of treatment. Early detection and treatment of cancer greatly increases the chances of survival.

SUMMARY

One aspect of the present application relates to a method for treating a prostate condition in a subject. The method comprises administering to the subject an effective amount of a first agent that inhibits Engrailed-2 (EN2) expression and/or EN2 activity; and administering to the subject an effective amount of a second agent that inhibits paired box homeotic gene 2 (PAX2) expression and/or PAX2 activity. In some embodiments, the method further comprises administering to the subject an effective amount of a third agent that enhances beta-defensin-1 (DEFB1) gene expression and/or DEFB1 activity.

Another aspect of the present application relates to a method of treating prostate cancer or prostatic intraepithelial neoplasia (PIN) in a subject. The method comprises administering to the prostate tissue of the subject an effective amounts of a first agent that that reduces expression and/or activity of EN2 and administering to the subject a second agent that enhances the expression and/or activity of DEFB1.

Another aspect of the present application relates to a method for treating prostate cancer or prostatic intraepithelial neoplasia (PIN) in a subject. The method comprises (a) determining expression levels of EN2, PAX2 and DEFB1, (b) determining a PAX2-to-DEFB1 expression ratio in a diseased prostate tissue from the subject; and (c) based on the results of (a) and (b), administering to said subject (1) an effective amounts of anagent that inhibits EN2 expression and (2) anagent that inhibits PAX2 expression and/or PAX2 activity and/or an agent that enhances expression and/or DEFB1 activity.

Another aspect of the present application relates to a pharmaceutical composition for treating prostate cancer or PIN. The pharmaceutical composition comprises (1) an agent that inhibits EN2 expression and/or EN2 activity and (2) an agent that inhibits PAX2 expression and/or PAX2 activity, and/or an agent that enhances expression and/or DEFB1 activity.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 5A-L show pan-caspase analysis following DEFB1 induction.

FIG. 36A is a Western blot analysis showing expression of PAX2 prior to PAX2 siRNA treatment in HPrEC prostate primary cells, and in DU145, PC3, and LNCaP prostate cancer cell lines. FIG. 36B is a Western blot analysis showing silencing of PAX2 protein expression following PAX2 siRNA treatment of DU145, PC3 and LNCaP cells.

DETAILED DESCRIPTION

Figure 1A:
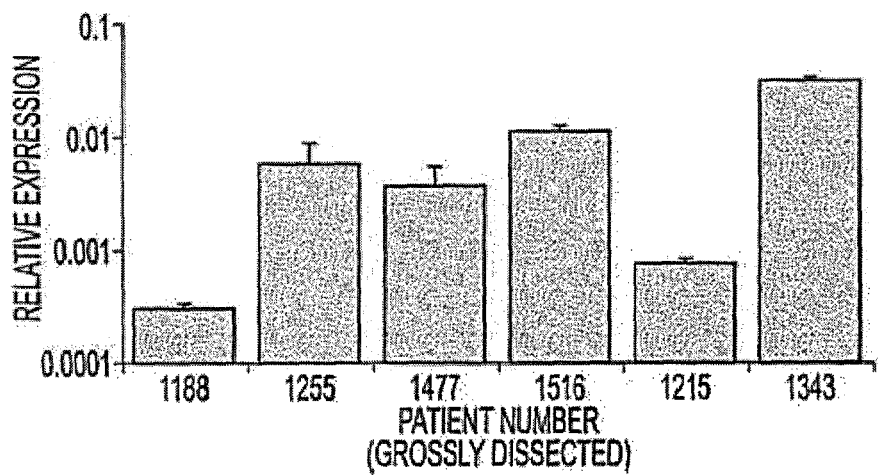
FIGS. 1A-1D show quantitative RT-PCR (QRT-PCR) analysis of DEFB1 expression.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

As used herein, the term "nucleic acid" refers to a polydeoxyribonucleotide (DNA or an analog thereof) or polyribonucleotide (RNA or an analog thereof) made up of at least two, and preferably ten or more bases linked by a backbone structure. In DNA, the common bases are adenine (A), guanine (G), thymine (T) and cytosine (C), whereas in RNA, the common bases are A, G, C and uracil (U, in place of T), although nucleic acids may include base analogs (e.g., inosine) and abasic positions (i.e., a phosphodiester backbone that lacks a nucleotide at one or more positions, U.S. Pat. No. 5,585,481). Exemplary nucleic acids include single-stranded (ss), double-stranded (ds), or triple-stranded polynucleotides or oligonucleotides of DNA and RNA.

The term "polynucleotide" refers to nucleic acids containing more than 10 nucleotides.

The term "oligonucleotide" refers to a single stranded nucleic acid containing between about 15 to about 100 nucleotides.

The term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. The promoter may be constitutively active or it may be active in one or more tissues or cell types in a developmentally regulated manner. A promoter may contain a genomic fragment or it may contain a chimera of one or more TREs combined together.

The term "EN2 expression," "PAX2 expression" or "DEFB1 expression" refers to the expression level of the EN2 gene, PAX2 gene or DEFB1 gene. The expression includes expression at the transcriptional level (e.g., mRNA), translational level (e.g., protein) and post-translational level (e.g., glycosylation).

The term "EN2 activity," "PAX2 activity" or "DEFB1 activity" refers to the biological activity of EN2 protein, PAX2 protein or DEFB1 protein. "Activities" of a protein include, for example, transcription, translation, intracellular translocation, secretion, phosphorylation by kinases, cleavage by proteases, homophilic and heterophilic binding to other proteins, ubiquitination.

Methods of Treatment

One aspect of the present application relates to methods for treating a prostate condition, such as prostate cancer or prostatic intraepithelial neoplasia (PIN), in a subject. In certain embodiments, the method comprises administering to the subject an effective amount of a first agent that inhibits Engrailed-2 (EN2) expression and/or EN2 activity and administering to the subject an effective amount of a second agent that inhibits PAX2 expression and/or PAX2 activity.

The present application provides a variety of inhibitors of PAX/EN2 expression and/or activity. Exemplary inhibitors include siRNA, aptamer-siRNA chimera, PAX2 or EN2 binding inhibitor, double-stranded oligonucleotide binding decoy comprising a PAX2 or EN2 binding site, single stranded antisense oligonucleotide, triplex forming oligonucleotide, ribozyme, external guide sequence, and combination thereof.

An siRNA is a double-stranded RNA that can be engineered to induce sequence-specific post-transcriptional gene silencing of EN2 and PAX2, which can decrease or eliminate expression of EN2 or PAX2 protein products. In one embodiment, the first bioactive component comprises a synthetic EN2-directed short interfering RNA (siRNA). Synthetically produced siRNAs structurally mimic the types of siRNAs normally processed in cells by the enzyme Dicer.

Synthetically produced siRNAs may incorporate any chemical modifications to the RNA structure that are known to enhance siRNA stability and functionality. For example, in some cases, the siRNAs may be synthesized as a locked nucleic acid (LNA)-modified siRNA. An LNA is a nucleotide analogue that contains a methylene bridge connecting the 2'-oxygen of the ribose with the 4' carbon. The bicyclic structure locks the furanose ring of the LNA molecule in a 3'-endo conformation, thereby structurally mimicking the standard RNA monomers. The therapeutic development of LNA-modified siRNAs has been described (Zhang et al., Gene Ther., 18:326-333, 2011; Veedu et al., RNA Biol., 6(3):321-323, 2009).

In certain embodiments, the siRNA and the corresponding EN2 cDNA sequences are:

```
EN2 cDNA:
                                        (SEQ ID NO: 106)
    5' TCAACGAGTCACAGATCAA 3' sense siRNA:
                                        (SEQ ID NO: 107)
    5' UCAACGAGUCACAGAUCAA 3' antisense siRNA:
                                        (SEQ ID NO: 108)
    3' AGUUGCUCAGUGUCUAGUU 5'

EN2 cDNA:
                                        (SEQ ID NO: 109)
    5' CCAACTTCTTCATCGACAA 3' sense siRNA:
                                        (SEQ ID NO: 110)
    5' CCAACUUCUUCAUCGACAA 3' antisense siRNA:
                                        (SEQ ID NO: 111)
    3' GGUUGAAGAAGUAGCUGUU 5'

EN2 cDNA:
                                        (SEQ ID NO: 112)
    5' CTCGAAAACCAAAGAAGAA 3' sense siRNA:
                                        (SEQ ID NO: 113)
    5' CUCGAAAACCAAAGAAGAA 3' antisense siRNA:
                                        (SEQ ID NO: 114)
    3' GAGCUUUUGGUUUCUUCUU 5'
```

Alternatively, or in addition, a PAX2 siRNA comprising a synthetic PAX2-directed siRNA may be used to silence or reduce PAX2 expression in prostate cells. In specific embodiments, the PAX2 siRNA may comprise a sequence selected from the group consisting of SEQ ID NOs: 15 and 73-78:

```
                                        (SEQ ID NO: 15)
            GGAUGCAGAUAGACUCGACUU, (SEQ ID NO: 73)
            AUAGACUCGACUUGACUUC, (SEQ ID NO: 74)
            CUUCAUCACGUUUCCUC, (SEQ ID NO: 75)
            GUAUUCAGCAAUCUUGUCC, (SEQ ID NO: 76)
            GAUUUGAUGUGCUCUGAUG,
```

-continued

GUCGAGUCUAUCUGCAUCC, (SEQ ID NO: 77)

AUGUGUCAGGCACACAGACG, (SEQ ID NO: 78)
and fragments of at least 10, 15 OR 20 nucleic acids and conservative variants thereof; and combinations thereof. In some embodiments, one or both of the first and second bioactive components may comprise an expression vector engineered to transcribe a short double-stranded hairpin-like RNA (shRNA) that is processed into an EN2 targeted siRNA inside the cell. The shRNAs can be cloned in suitable expression vectors using kits, such as Ambion's SILENCER® siRNA Construction Kit, Imgenex's GENESUPPRESSOR™ Construction Kits, and Invitrogen's BLOCK-ITT™ inducible RNAi plasmid and lentivirus vectors. Other PAX2 sequences that have been targeted by siRNA include: #1 ACCCGAC-TATGTTCGCCTGG (SEQ ID NO: 11), #2 AAGCTCTG-GATCGAGTCTTTG (SEQ ID NO: 12), and #4 ATGTGT-CAGGCACACAGACG (SEQ ID NO: 13). #4 was shown to inhibit PAX2 (Davies et al., Hum. Mol. Gen. 2004, 13:235).

Thus, in certain embodiments, the first bioactive component comprises an expression vector capable of expressing an EN2 siRNA comprising a sequence selected from the group consisting of SEQ ID NOS: 107, 108, 110, 111, 113 and 114.

Alternatively, or in addition, the second bioactive component may comprise an expression vector capable of expressing an EN2 siRNA comprising an EN2 sequence selected from the group consisting of SEQ ID NOs: 3-6 and 11-15.

Synthetic siRNAs and shRNAs may be designed using well known algorithms and synthesized using a conventional DNA/RNA synthesizer. PAX2 and EN2 siRNAs, as well as PAX2 and EN2 shRNA expression constructs may be commercially obtained from Origen (Rockville, Md.).

The use of siRNAs exploits the mechanism of RNA interference (RNAi) to silence gene expression of EN2 and/or PAX2. This "silencing" was originally observed in the context of transfecting double stranded RNA (dsRNA) into cells. Upon entry therein, the dsRNA was found to be cleaved by an RNase III-like enzyme, Dicer, into double stranded small interfering RNAs (siRNAs) 21-23 nucleotides in length containing 2 nucleotide overhangs on their 3' ends. In an ATP dependent step, the siRNAs become integrated into a multi-subunit RNAi induced silencing complex (RISC) which presents a signal for AGO2-mediated cleavage of the complementary mRNA sequence, which then leads to its subsequent degradation by cellular exonucleases.

An aptamer-siRNA chimera is a targeted siRNA comprising an siRNA chemically linked to a cell internalizing aptamer. An aptamer is a nucleic acid version of an antibody that comprises a class of oligonucleotides that can form specific three dimensional structures exhibiting high affinity binding to a wide variety of cell surface molecules, proteins, and/or macromolecular structures. Typically, aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase, thrombin, and a variety of cell surface receptors.

An aptamer can be chemically linked or conjugated to the above described nucleic acid inhibitors to form targeted nucleic acid inhibitors (Ray et al., Pharmaceuticals, 3:1761-1778, 2010). An aptamer-siRNA chimera contains a targeting moiety in the form of an aptamer which is linked to an siRNA (Chu et al., Nucl. Acids Res., 34(10):e73, 2006; Zhou et al., Silence, 1:4-10, 2010). In one embodiment, the inhibitor comprises a chimeric aptamer-si RNA oligonucleotide capable of targeting prostate tissue as previously described (Dassie et al., Nat. Biotech., 27(9):839-849, 2009; McNamara et al., Nat. Biotech., 24(8):1005-1015). Preferably, the aptamer is a cell internalizing aptamer. Upon binding to specific cell surface molecules, the aptamer can facilitate internalization into the cell where the nucleic acid inhibitor acts. In one embodiment both the aptamer and the siRNA comprises RNA. The aptamer and the siRNA may comprise any nucleotide modifications as further described herein. In a specific embodiment, the aptamer comprises a targeting moiety specifically binding the prostate-specific membrane antigen (PSMA).

Aptamers can bind very tightly with Kds from the target molecule of less than 10-12M. It is preferred that the aptamers bind the target molecule with a Kd less than 10-6, 10-8, 10-10, or 10-12. Aptamers can bind the target molecule with a very high degree of specificity. For example, aptamers have been isolated that have greater than a 10,000 fold difference in binding affinities between the target molecule and another molecule that differ at only a single position on the molecule.

In another embodiment, one or both of the first and second bioactive components may comprise an antisense oligonucleotide or polynucleotide. The antisense oligonucleotide or polynucleotide may comprise a DNA backbone, RNA backbone, or chemical derivative thereof. In one embodiment, one or both of the first and second bioactive components comprises a single stranded antisense oligonucleotide or polynucleotide targeting EN2 and/or PAX2 for degradation. In preferred embodiments, the bioactive component comprises a single stranded antisense oligonucleotide complementary to EN2 and/or PAX2 mRNA sequences. The single stranded antisense oligonucleotide or polynucleotide may be synthetically produced or it may be expressed from a suitable expression vector. The antisense nucleic acid is designed to bind via complementary binding to the mRNA sense strand so as to promote RNase H activity, which leads to degradation of the mRNA. Preferably, the antisense oligonucleotide is chemically or structurally modified to promote nuclease stability and/or increased binding.

In some embodiments, the antisense oligonucleotides are modified to produce oligonucleotides with nonconventional chemical or backbone additions or substitutions, including but not limited to peptide nucleic acids (PNAs), locked nucleic acids (LNAs), morpholino backboned nucleic acids, methylphosphonates, duplex stabilizing stilbene or pyrenyl caps, phosphorothioates, phosphoroamidates, phosphotriesters, and the like. By way of example, the modified oligonucleotides may incorporate or substitute one or more of the naturally occurring nucleotides with an analog; internucleotide modifications incorporating, for example, uncharged linkages (e.g., methyl phosphonates, phosphotriesters, phosphoamidates, carbamates, etc.) or charged linkages (e.g., phosphorothioates, phosphorodithioates, etc.); modifications incorporating intercalators (e.g., acridine, psoralen, etc.), chelators (e.g., metals, radioactive metals, boron, oxidative metals, etc.), or alkylators, and/or modified linkages (e.g., alpha anomeric nucleic acids, etc.).

In some embodiments, the single stranded oligonucleotides are internally modified to include at least one neutral charge in its backbone. For example, the oligonucleotide may include a methylphosphonate backbone or peptide nucleic acid (PNA) complementary to the target-specific sequence. These modifications have been found to prevent or reduce helicase-mediated unwinding. The use of uncharged probes may further increase the rate of hybridization to polynucleotide targets in a sample by alleviating the repulsion of negatively-charges nucleic acid strands in classical hybridization (Nielsen et al., 1999, Curr. Issues Mol. Biol., 1:89-104).

PNA oligonucleotides are uncharged nucleic acid analogs for which the phosphodiester backbone has been replaced by a polyamide, which makes PNAs a polymer of 2-aminoethyl-glycine units bound together by an amide linkage. PNAs are synthesized using the same Boc or Fmoc chemistry as are use in standard peptide synthesis. Bases (adenine, guanine, cytosine and thymine) are linked to the backbone by a methylene carboxyl linkage. Thus, PNAs are acyclic, achiral, and neutral. Other properties of PNAs are increased specificity and melting temperature as compared to nucleic acids, capacity to form triple helices, stability at acid pH, non-recognition by cellular enzymes like nucleases, polymerases, etc. (Rey et al., 2000, FASEB J., 14:1041-1060; Nielsen et al., 1999, Curr. Issues Mol. Biol., 1:89-104).

Methylphosphonate-containing oligonucleotides are neutral DNA analogs containing a methyl group in place of one of the non-bonding phosphoryl oxygens. Oligonucleotides with methylphosphonate linkages were among the first reported to inhibit protein synthesis via anti-sense blockade of translation. However, the synthetic process yields chiral molecules that must be separated to yield chirally pure monomers for custom production of oligonucleotides (Reynolds et al., 1996, Nucleic Acids Res., 24:4584-4591).

In some embodiments, the phosphate backbone in the oligonucleotides may contain phosphorothioate linkages or phosphoroamidates (Chen et al., Nucl. Acids Res., 23:2662-2668 (1995)). Combinations of such oligonucleotide linkages are also within the scope of the present invention.

In other embodiments, the oligonucleotide may contain a backbone of modified sugars joined by phosphodiester internucleotide linkages. The modified sugars may include furanose analogs, including but not limited to 2-deoxyribofuranosides, α-D-arabinofuranosides, α-2'-deoxyribofuranosides, and 2',3'-dideoxy-3'-aminoribofuranosides. In alternative embodiments, the 2-deoxy-β-D-ribofuranose groups may be replaced with other sugars, for example, β-D-ribofuranose. In addition, β-D-ribofuranose may be present wherein the 2-OH of the ribose moiety is alkylated with a C1-6 alkyl group (2-(O—C1-6 alkyl)ribose) or with a C2-6 alkenyl group (2-(O—C2-6 alkenyl)ribose), or is replaced by a fluoro group (2-fluororibose).

Related oligomer-forming sugars include those used in locked nucleic acids (LNA) as described above. Exemplary LNA oligonucleotides include modified bicyclic monomeric units with a 2'-O-4'-C methylene bridge, such as those described in U.S. Pat. No. 6,268,490, the disclosures of which are incorporated by reference herein.

Chemically modified oligonucleotides may also include, singly or in any combination, 2'-position sugar modifications, 5-position pyrimidine modifications (e.g, 5-(N-benzylcarboxyamide)-2'-deoxyuridine, 5-(N-isobutylcarboxyamide)-2'-deoxyuridine, 5-(N-[2-(1H-indole-3yl)ethyl]carboxyamide)-2'-deoxyuridine, 5-(N-[1-(3-trimethylammonium)propyl]carboxyamide)-2'-deoxyuridine chloride, 5-(N-napthylcarboxyamide)-2'-deoxyuridine, and 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, methylations, unusual base-pairing combinations, such as the isobases isocytidine and isoguanidine, and the like.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming oligonucleotides (TFOs) are molecules that can interact with either double-stranded and/or single-stranded nucleic acid. When TFOs interact with a target region, a structure called a triplex is formed, in which there are three strands of DNA forming a complex dependant on both Watson-Crick and Hoogsteen base-pairing. TFOs can bind target regions with high affinity and specificity. In preferred embodiments, the triplex forming molecules bind the target molecule with a Kd less than 10-6, 10-8, 10-10, or 10-12. Exemplary TFOs for use in the present invention include PNAs, LNAs, and LNA modified PNAs, such as Zorro-LNAs (Ge et al., FASEB J., 21:1902-1914, 2007; Zaghloul et al., Nucl. Acids Res., 39(3):1142-1154, 2011). In a preferred embodiment, the triplex forming oligonucleotide targets a PAX2 binding site in the DEFB1 promoter further described herein.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells.

In one embodiment, the agent that inhibits EN2 expression and/or EN2 activity comprises one or more members selected from the group consisting of EN2 siRNA, aptamer-siRNA chimera, single stranded antisense oligonucleotide, triplex forming oligonucleotide, ribozyme, external guide sequence, polynucleotide encoding a EN2 siRNA.

In another embodiment, the agent that inhibits PAX2 expression and/or PAX2 activity comprises one or more members selected from the group consisting of PAX2 siRNA, aptamer-siRNA chimera, single stranded antisense oligonucleotide, triplex forming oligonucleotide, ribozyme, external guide sequence, polynucleotide encoding a PAX2 siRNA, PAX2 binding inhibitor, double-stranded oligonucleotide binding decoy comprising a PAX2 binding site in the beta defensin-1 (DEFB1) promoter, antagonist of angiotensin II, antagonist of the angiotensin II receptor, antagonist of angiotensin-converting enzyme (ACE), antagonist of mitogen-activated protein kinase (MEK), antagonist of extracellular signal-regulated kinase 1,2 (ERK1,2), AMP kinase activator, antagonist of signal transducer and activator of transcription 3 (STAT3), and blocker of the RAS signaling pathway, and combination thereof.

In one embodiment, the inhibitor of PAX2 expression or activity (or second bioactive component) blocks the binding of PAX2 to PAX2 target sites, such as the DEFB1 promoter. In one embodiment, the second bioactive component comprises a double-stranded oligonucleotide binding decoy comprising a PAX2 binding site in the DEFB1 promoter. The decoy is administered in excess to bind and neutralize PAX2 so as to prevent or reduce its binding to native PAX2 target genes, such as DEFB1. In preferred embodiments, the decoy comprises a sequence known to bind PAX2 at a high affinity. Exemplary decoy sequences include the PAX2 binding sequence in the DEFB1 promoter, as exemplified in SEQ ID NOs: 16, 18, and 19.

In another embodiment, the inhibitor of PAX2 expression or activity comprises an antagonist of angiotensin II, an antagonist of the angiotensin II type 1 receptor (AT1R), or an antagonist of angiotensin-converting enzyme (ACE). In one embodiment, the inhibitor is an antagonist of the angiotensin II type 1 receptor (AT1R). Exemplary AT1R antagonists include losartan, valsartan, olmesartan, and telmisartan. In another embodiment, the inhibitor is an antagonist of angiotensin-converting enzyme (ACE), such as enalapril.

In other embodiments, the inhibitor of PAX2 expression or activity comprises antagonists of MEK, ERK1, or ERK2, such as U0126 or PD98059. U0126 is a chemically synthesized organic compound that was initially recognized as a cellular AP-1 antagonist, and found to be a very selective and highly potent inhibitor of mitogen-activated protein kinase (MAPK) cascade by inhibiting its immediate upstream activators, mitogen activated protein kinases 1 and 2 (also known as MEK1 and MEK2, IC50: 70 and 60 nM respectively). U0126 inhibits both active and inactive MEK1,2, unlike PD98059 which only inhibits activation of inactive MEK. Blockade of MEK activation would prevent downstream phosphorylation of a number of factors including p62TCF (Elk-1), an upstream inducer of c-Fos and c-Jun, components of the AP-1 complex. Inhibition of the MEK/ERK pathway by U0126 can also prevent the oncogenic effects of H-Ras and K-Ras, inhibit the effects upstream growth factors, and block the production of inflammatory cytokines and matrix metalloproteinases.

PD98059 has been shown to act in vivo as a highly selective inhibitor of MEK1 activation and the MAP kinase cascade. PD98059 binds to the inactive forms of MEK1 and prevents activation by upstream activators such as c-Raf. PD98059 inhibits activation of MEK1 and MEK2 with IC50 values of 4 μM and 50 μM, respectively.

In other embodiments, the inhibitor of PAX2 expression or activity comprises an AMP kinase activator. In a preferred embodiment the AMP kinase inhibitor comprises 5-aminoimidazole-4-carboxamide-1-β-4-ribofuranoside (AICAR).

Figure 27:
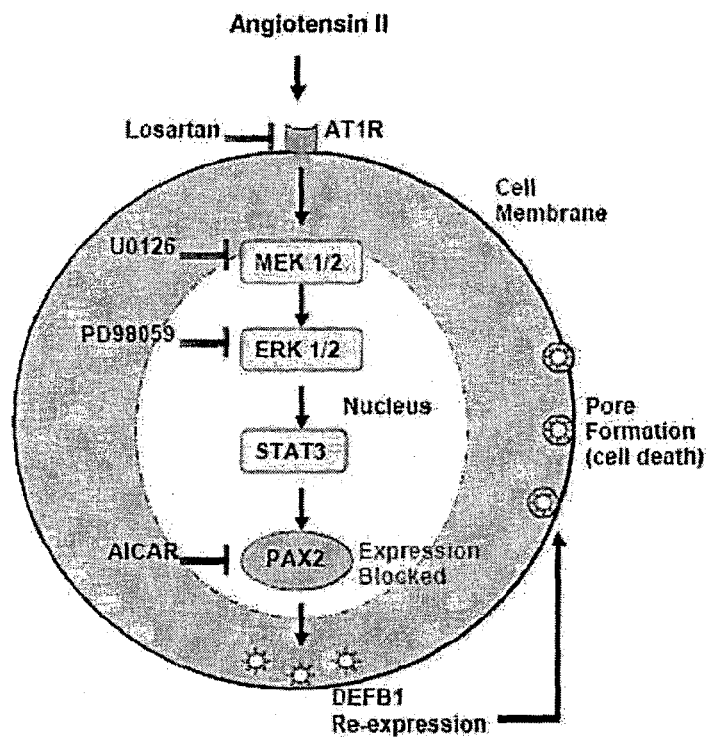
FIG. 27 shows a schematic of blocking PAX2 expression as a therapy for prostate cancer.

It is known that PAX2 expression is regulated by signal transducer and activator of transcription 3 (STAT-3), which is a downstream target of AT1R, MEK, ERK1, ERK2, and AMPK (see e.g., FIG. 27). Accordingly, in another embodiment, the inhibitor of PAX2 expression or activity may comprise a STAT-3 antagonist, such as losartan, valsartan, olmesartan, telmisartan, U0126, PD98059, AICAR, and combinations thereof.

In another embodiment, one or more bioactive components include a targeting domain for targeting the delivery of the bioactive components to prostate tissues. The targeting moiety may comprise an aptamer, peptide, antibody-derived epitope binding domain, virus, or cellular ligand capable of binding to the surface of prostate cells. The targeting moiety may be genetically engineered into a delivery vehicle, such as a viral vector or liposome, or it may be chemically conjugated to a bioactive component, such as an siRNA, as described in Meade et al., Adv. Drug Deliv., 60(4-5):530-536, 2008. In preferred embodiments, the targeting moiety binds to a cell surface epitope whose expression is upregulated in cancerous or pre-cancerous prostate tissues.

In one embodiment, the targeting moiety comprises an aptamer as described above.

In another embodiment, the targeting moiety comprises a peptide known to bind prostate cells. Exemplary prostate-targeting peptides are described in. In one embodiment, the cell-binding peptide is isolated from a phage display library, for example. Phage display libraries engineered for binding cell surface molecules or receptors are well known to those of skill in the art.

In one embodiment, the peptide comprises an internalizing peptide (also referred to as a cell penetrating peptide (CPP) or protein transduction domain (PTD)) to facilitate entry of the bioactive component through the eukaryotic cell membrane as described in e.g., Joliot et al., Nature Cell Biol., 6(3):189-196, 2004 and Heitz et al., Br. J. Pharmacol., 157:195-206, 2009. Exemplary internalizing peptides for use in the present invention include, but are not limited to, HIV TAT49-57 peptide (RKKRRQRRR, SEQ ID NO:79), HIV TAT48-60 peptide (GRKKRRQRRRPPQ, SEQ ID NO:80), low molecular weight protamine (LMWP) peptide (e.g., TDSP5, VSRRRRRRGGRRRR, SEQ ID NO:81, as described in US Publication No. 2007/0071677); Chariot™ (KETWWETWW-TEWSQPKKKRKV, SEQ ID NO:82), also known as PEP-1 (Morris et al., Nat. Biotechnol., 19:1173-1176, 2001); Antp43-58 (RQIKIWFQNRRMKWKK, SEQ ID NO:83) peptide, MPG (HIV Gp41-SV40 NLS, GALFLGFLGAAG-STMGAWSQPKKKRKV, SEQ ID NO:84), SAP (VRLPP-PVRLPPPVRLPPP, SEQ ID NO:85), MPG R9 (RRRRRRRRR, SEQ ID NO:86), MAP (KLALKLALKA-LKAALKLA, SEQ ID NO:87; and KALAKALAKALA, SEQ ID NO:88), K-FGF (AAVALLPAVLLALLAP, SEQ ID NO:89), Penetratin (RQIKIWFQNRRMKWKK, SEQ ID NO:90), Buforin II, (TRSSRAGLQFPVGRVHRLLRK, SEQ ID NO:91), Transportan (GWTLNSAGYLLGKINKA-LAALAKKIL, SEQ ID NO:92), Ku70 (VPMLK, SEQ ID NO:93), Prion (MANLGYWLLALFVTMWTDVGLCK-KRPKP, SEQ ID NO:94), and pVEC (LLIIILRRRIRKQA-HAHSK, SEQ ID NO:95), Pep-7 (SDLWEMMMVSL-ACQY, SEQ ID NO:96), HN-1 (TSPLNIHNGQKL, SEQ ID NO:97), and CP26 (KWKSFIKKLTSAAKKVVTTAKP-LISS (SEQ ID NO:98).

In another embodiment, the targeting moiety comprises an antibody-derived epitope binding domain selected from the group consisting of: IgG, antibody variable region; isolated CDR region; single chain Fv molecule (scFv) comprising VH and VL domain linked by a peptide linker allowing for association between the two domains to form an antigen binding site; bispecific scFv dimer; minibody comprising a scFv joined to a CH3 domain, single chain diabody fragment, dAb fragment, which consists of a VH or a VL domain; Fab fragment consisting of VL, VH, CL and CH1 domains; Fab' fragment, which differs from a Fab fragment by the addition of a few residues at the carboxyl terminus of the heavy chain CH1 domain, including one or more cysteines from the antibody hinge region; Fab'-SH fragment, which is a Fab' fragment in which the cysteine residue(s) of the constant domains bear a free thiol group; F(ab')2, bivalent fragment comprising two linked Fab fragments; Fd fragment consisting of VH and CH1 domains; derivatives thereof, and any other antibody fragment(s) retaining antigen-binding function. Fv, scFv, or diabody molecules may be stabilized by the incorporation of disulphide bridges linking the VH and VL domains. In addition, the targeting moiety may be further linked to at least a portion an Fc region. The Fc region can facilitate recruitment of Fc receptor-bearing natural killer cells, macrophages, neutrophils, and mast cells, which can stimulate phagocytic or cytotoxic cells to destroy the targeted prostate cell by antibody-mediated phagocytosis or antibody-dependent cell-mediated cytotoxicity. Further, when using antibody-derived targeting agents, any or all of the targeting domains therein and/or Fc regions may be "humanized" using methodologies well known to those of skill in the art.

In certain embodiments, the method further comprises administering into the subject a third agent that enhances DEFB1 expression or DEFB1 activity. Examples of the agents that enhances DEFB1 expression or DEFB1 activity include, but are not limited to, DEFB1 protein, DEFB1 saRNAs, expression vectors encoding a DEFB1 saRNA, expression vectors encoding DEFB1 protein, interferon-γ, and a combination thereof.

The first agent, second agent and/or third agent may be administered concurrently in a single pharmaceutical composition or administered individually. In one embodiment, the first agent, the second agent and/or the third agent are administered directly into the prostate cancer tissue or PIN tissue in the subject.

In another aspect, the present invention provides a method for treating prostate cancer or PIN in a subject, comprising administering into the subject an effective amount of a first agent that inhibits EN2 expression and/or EN2 activity, and administering into the subject an effective amount of a second agent that enhances DEFB1 expression and/or DEFB1 activity.

A small activating RNA (saRNA) or dsRNA activator is similar to a siRNA, except that it activates gene expression by a mechanism called "small RNA-induced gene activation" or RNAa. dsRNAs comprise a class of microRNAs (miRNAs) that are a group of small noncoding RNAs that serve as endogenous sources of dsRNA. A DEFB1 saRNA comprises a ribonucleotide strand that is complementary to a non-coding nucleic acid sequence of the gene. In a preferred embodiment, the a DEFB1 saRNA comprises ribonucleic acid sequences targeting DEFB1 transcriptional regulatory sequences, including DEFB1 promoter or enhancer sequences. dsRNA activators and polynucleotides encoding them can be synthesized or constructed as siRNAs or shRNAs as described in Li et al., Proc. Natl. Acad. Sci. USA, 103(46): 17337-17342, 2006; Chen et al., Mol. Cancer. Ther., 7(3): 698-703, 2008.

Another aspect of the present application relates to a method for monitoring or diagnosing cancerous, pre-cancerous, or non-cancerous prostate conditions in a test subject and then based on those results, administering to the prostate tissue of the subject effective amounts of an agent that inhibits EN2 expression and/or EN2 activity and a second agent that inhibits PAX2 expression or PAX2 activity.

In certain embodiments, the method for monitoring or diagnosing cancerous, pre-cancerous, or non-cancerous conditions in a test subject comprises determining a PAX2-to-DEFB1 or EN2-to-DEFB1 expression ratio in cells or bodily fluids obtained from the test subject, wherein the PAX2-to-DEFB1 expression ratio or the EN2-to-DEFB1 expression ratio is correlated with one or more cancerous, pre-cancerous, or non-cancerous conditions.

In one embodiment, a method for treating a prostate condition in a subject, comprises: (a) determining the PAX2-to-DEFB1 expression ratio in a diseased prostate tissue from the subject; and (b) based on the results of (a), administering to the prostate tissue of the subject a first bioactive component that inhibits EN2 expression and/or EN2 activity and a second bioactive component that inhibits PAX2 expression and/or PAX2 activity. In a related embodiment, the method further comprises administering to the prostate tissue of the subject a third bioactive component that enhances expression and/or activity of DEFB1. In some embodiments, the prostate condition is prostate cancer or PIN.

In another embodiment, a method for treating a prostate condition in a subject, comprises: (a) determining expression levels of EN2, PAX2 and DEFB1, (b) determining a PAX2-to-DEFB1 and/or EN2-to-DEFB1 expression ratio in a diseased prostate tissue from the subject; and (c) based on the results of (a) and (b), administering to the subject (1) an effective amounts of an agent that inhibits EN2 expression and (2) an agent that inhibits PAX2 expression and/or PAX2 activity, and/or an agent that enhances DEFB1 expression and/or DEFB1 activity. In some embodiments, the prostate condition is prostate cancer or PIN.

In certain embodiments, the determining step comprises determining the expression level the PAX2 gene relative to the expression level of an internal control gene, determining the expression level of DEFB1 gene relative to the expression level of the same control gene, and determining the PAX2-to-DEFB1 expression ratio based on the expression levels of PAX2 and DEFB1. Any suitable internal control gene may be used as long as its expression is known to be substantially constant in all cell types. Exemplary internal control genes include, but are not limited to the β-actin gene, glyceraldehyde 3-phosphate dehydrogenase (GAPDH) gene, and the like.

In one embodiment, the PAX2-to-DEFB1 expression ratio from prostate cells is used for distinguishing among cancerous, pre-cancerous, and non-cancerous prostate conditions in the test subject. In one embodiment, a PAX2-to-DEFB1 expression ratio of 100:1 or higher is indicative of the presence of prostate cancer in the subject. In another embodiment, a PAX2-to-DEFB 1 expression ratio of 40:1 or higher, but less than 100:1, is indicative of the presence of prostate intraepithelial neoplasia (PIN) in the subject. In yet another embodiment, a PAX2-to-DEFB1 expression ratio of less than 40:1 is indicative of normal prostate in the subject.

In other embodiments, the PAX2-to-DEFB1 expression ratio from prostate cells is used for distinguishing among cancerous, pre-cancerous, and non-cancerous prostate conditions in the test subject. In one embodiment, a PAX2-to-DEFB1 expression ratio of 100:1 or higher is indicative of the presence of prostate cancer in the subject. In another embodiment, a PAX2-to-DEFB1 expression ratio of 40:1 or higher, but less than 100:1, is indicative of the presence of prostate intraepithelial neoplasia (PIN) in the subject. As used herein, the term "prostate intraepithelial neoplasia" includes lobular intraepithelial neoplasia and ductal intraepithelial neoplasia. In yet another embodiment, a PAX2-to-DEFB1 expression ratio of less than 40:1 is indicative of a normal prostate condition.

In certain embodiments, the method for monitoring or diagnosing cancerous, pre-cancerous, and non-cancerous conditions in a test subject comprises determining a PAX2 expression level in cells or bodily fluids obtained from tissue of the test subject suspected to be at risk for cancer, determining an EN2 expression level in cells or bodily fluids obtained from the test subject suspected to be at risk for cancer, and comparing the PAX2 and EN2 expression levels from the tissue of the test subject with the expression levels obtained from the same tissue of a cancer-free control subject, wherein expression level increases of at least 2-fold in each of PAX2 and EN2 in the test subject relative to the control subject are indicative of cancer or of an increased risk for developing cancer. Expression level increases of at least 50%. 100%, 150%, 200%, 250%, 300%, 400% or more may be observed. The cells may be obtained from any tissue in which EN2 and PAX2 are upregulated in cancer. Preferred tissues include prostate and prostate tissue. Preferred bodily fluids include blood, plasma, serum, and urine.

In certain embodiments, the method may alternatively or additionally comprise the step of determining a DEFB1 expression level in the cells or bodily fluids obtained from the tissue of the test subject (in addition to EN2 and PAX2), and comparing those expression levels to corresponding reference levels (e.g., expression levels obtained from the cells or bodily fluids of normal control subjects), wherein expression level increases in EN2 and PAX2 in the test subject relative to the control and an expression level decrease in DEFB1 in the test subject relative to the control are indicative of cancer or a risk for developing cancer.

In addition, the herein disclosed methods can comprise the detection, including measurement, of PAX2, EN2, and/or DEFB1 in bodily fluids of the subject, such as blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

Gene expression levels and gene expression ratios may be determined at the mRNA level (e.g., by RT-PCR, QT-PCR, oligonucleotide array, etc) or at the protein level (e.g., by Western blot, antibody microarray, ELISA, etc.). Preferred methodologies for determining mRNA expression levels (and ratios therefrom) include quantitative reverse transcriptase PCR (QT-PCR), quantitative real-time RT-PCR, oligonucleotide microarray, antibody microarray, or combination thereof. Preferred methodologies for determining protein expression levels (and ratios therefrom) include the use of ELISAs and antibody microarrays.

In some embodiments, the method further comprises determining an androgen receptor (AR) status (i.e., hormone-sensitive or hormone-refractory) in prostate cells or bodily fluids obtained from the test subject. The AR status of the prostate tissue may be used, in combination with the EN2-to-DEFB1 ratio and/or PAX2-to-DEFB1 ratio in the same tissue, for determining the prostate conditions in the subject.

In other embodiments, the method further comprises determining an oestrogen receptor/progesterone receptor (ER/PR) status in cells or bodily fluids obtained from the prostate tissue with the prostate condition. The ER/PR status of the prostate tissue may be used, in combination with the PAX2-to-DEFB1 ratio in the same tissue, for determining the prostate conditions in the subject.

The monitoring and diagnosing methods of the present invention provide clinicians with a prognosticator for initiated or pre-cancerous tissue. Candidates for this test include patients at high risk (based on age, race) for cancer. As a diagnostic, positive or negative PAX2, EN2, and/or DEFB1 tests can then be followed by additional screening with biomarkers to determine cancer status. In addition, these patients can be candidates for treatment with PAX2/EN2/DEFB1 modulators. Alternatively, these tests can be used on patients to monitor the effectiveness of their cancer therapy, to determine treatment course, or to monitor cancer recurrence.

As another example, patients who present with potential indicators of cancer such as the detection of nodules in the prostate during a digital rectal exam by the clinician, or those who experience a sudden rise in PSA often are in the "Watchful Waiting" state. It is often difficult to ascertain whether these patients have cancer or will develop cancer. An analysis of PAX2, EN2, DEFB1 expression levels or PAX2-to-DEFB1 and/or EN2-to-DEFB1 expression ratios in patient samples from e.g., tissues, blood, plasma, serum, and/or urine can be used to assist the decision to obtain a biopsy in men with suspected prostate cancer, which can lead to a reduction in the number of unnecessary prostate biopsies and earlier intervention for the disease. In a biopsy, small tissue samples are removed from a target organ for further analysis. Prostate biopsies are typically performed when the scores from a PSA blood test rise to a level that is associated with the possible presence of prostate cancer.

Identification of blood protein markers can provide a more accurate or earlier diagnosis of cancer can have a positive impact on cancer treatment and management. As disclosed herein, aberrant PAX2 expression occurs early in the progression of cancer and can be an initiating event in tumorigenesis. Therefore, samples from patients collected to screen for the presence of PAX2 protein or antigens can be used for the early detection of cancer.

Furthermore, the incorporation of PAX2/EN2/DEFB1 screening can provide clinicians with a prognosticator for initiated or pre-cancerous tissue. Candidates for this test include patients at high risk (based on age, race) for cancer. As a diagnostic, a positive PAX2 test can then be followed by additional screening with other biomarker(s). In addition, these patients can be candidates for PAX2 inhibitors for chemoprevention for their cancers. Alternatively, this test can be used on patients as a measure of the effectiveness of their cancer therapy or to monitor cancer recurrence.

Compositions for Treatment

In a further aspect, the present invention provides compositions for treating prostate cancer or prostate intraepithelial neoplasia (PIN) in accordance with the methods described herein. In one embodiment, the composition comprises a first agent that inhibits EN2 expression and/or EN2 activity, a second agent that inhibits PAX2 expression and/or PAX2 activity, and a pharmaceutically acceptable carrier. The composition may further include a third agent that enhances expression and/or DEFB1 activity. Examples of agents that inhibit EN2 expression and/or EN2 activity, agent that inhibits PAX2 expression and/or PAX2 activity, and agents that enhances expression and/or DEFB1 activity have been described in the "Method of Treatment" section.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

In another embodiment, the composition for treating prostate cancer or PIN comprises a first bioactive component that inhibits EN2 expression and/or EN2 activity and a second bioactive component that enhances expression and/or activity of DEFB1, and a pharmaceutically acceptable carrier. The bioactive components may include any of the bioactive components and compositions thereof as described herein.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials may be in solution, suspension (for example, incorporated into microparticles, liposomes, or cells). These may be targeted to a particular cell type via antibodies, receptors, or receptor ligands. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

The compositions described herein can be packaged together in any suitable combination as a kit useful for performing, or aiding in the performance of, the disclosed method. In some embodiments, the kit for treating prostate conditions, such as prostate cancer or PIN, comprises an inhibitor of EN2 expression or activity, an inhibitor of PAX2 expression or activity, and/or an activator of DEFB1 expression or activity. The inhibitors or activators may comprise any of the above described bioactive components.

A composition disclosed herein may be administered in a number of ways depending on whether local or systemic treatment is desired, and on the area to be treated. For example, the compositions may be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

The exact amount of the compositions required will vary from subject to subject, depending on the species, age, weight and general condition of the subject, the particular nucleic acid or vector used, its mode of administration and the like. An appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorders are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the disclosed composition used alone might range from about 1 μg/kg to up to 100 mg/kg of body weight or more per day, depending on the factors mentioned above. In certain embodiments, the treatment method is tailored based on the PAX2-to-DEFB1 expression ratio (P/D ratio) and/or the prostate specific antigen (PSA) status of the diseased tissue. Therefore monitoring PAX2 expression levels can be used to predict drug response or resistance, as well as identify patients who may be candidates for anti-EN2, anti-PAX2, and/or DEFB1 therapy. The terms "anti-EN2 therapy" and "anti-PAX2 therapy" refers to methods for inhibiting EN2/PAX2 expression or EN2/PAX2 activity. The term "DEFB1 therapy" refers to methods for increasing DEFB1 expression. The term "DEFB1 therapy" does not include methods for inhibiting EN2/PAX2 expression or EN2/PAX2 activity, although such methods may also result in increase of DEFB1 expression.

Other Inhibitors

In some embodiments, the agents described herein are combined with one or more conventional chemotherapeutic agents. Exemplary chemotherapeutic agents for use in the present invention include 5-alpha-reductase inhibitors, including finasteride, dutasteride, turosteride, bexlosteride, izonsteride, FCE 28260, and SKF 105, 111; integrin-linked kinase (ILK) inhibitors, such as QLT-0267; secreted frizzled-related protein-1 (sFRP1), secreted frizzled-related protein-2 (sFRP2), secreted frizzled related protein-3 (sFRP3/FRZB), secreted frizzled-related protein-4 (sFRP4), secreted frizzled-related protein-5 (SFRP5), Dickkopf-1 (DKK1), Dickkopf-2 (DKK2), Dickkopf-3 (DKK3), Wnt inhibitory factor-1 (WIF1), cerberus, sclerostin, IWR-1-endo, IWP-2, IWP-3, IWP4, pyrvinium, XAV939, and other WNT signalling pathway inhibitors; bevacizumab (Avastin), cabazitaxel, ketoconazole, prednisone, Sipuleucel-T (APC8015, Provenge), Alpharadin (radium-223 chloride), MDV3100, orteronel (TAK-700), PROSTVAC, cabozantinib (XL-184), DMAPT; cyclopamine, IP-926, vismodegib, and other hedgehog (Hh) signalling pathway inhibitors; flutamide, luprolide, antiestrogens, such as tamoxifen; antimetabolites and cytotoxic agents, such as daunorubicin, fluorouracil, floxuridine, interferon alpha, methotrexate, plicamycin, mercaptopurine, thioguanine, adramycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, idamycin, hormones such as, medroxyprogesterone, estramustine, ethinyl oestradiol, oestradiol, leuprolide, megestrol, octreotide, diethylstilbestrol, chlortrianisene, etoposide, podophyllotoxin, goserelin, nitrogen mustard derivatives such as, melphalan, chlorambucil, methlorethamine, thiotepa, steroids such as, betamethasone, and other antineoplastic agents such as live *Mycobacterium bovis*, dicarbazine, asparaginase, leucovor-ibn, mitotane, vincristine, vinblastine, texotere, cydophosphamide, adriamycin, 5-fluorouracil, hexamethylmelamine, acivicin; aclarubicin; acodazole hydrochloride; acrqnine; adozolesin; aldesloukin; altretamine; ambomycin; ametantrone acetate; aminogluthimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomyrin; edatrexate; eflomithine hydrochloride; elsamitrucin; enloplatin; enprorfate; epipropidine; epirubicin hydrochloride; erbulozole; esorubicin hydrochloride; estramustine; estramustine phosphate sodium; etanidazole; ethiodized oil I 131; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; gold Au 198; hydroxyurea; idarubicin hydrochloride; ifosfamide; ilmofosine; interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometerxol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; strontium chloride Sr 89; sulofenur; talisomycin; taxane; taxoid; tecogalan sodium; tegafur; teloxantrone hydrochloride; temoporfin; teniposide; teroxirono; testolactone; thiamiprine; thioguanine; thiotepa; tiazofurin; tirapazamine; topotecan hydrochloride; toremifene citrate; trestolone acetate; triciribine phosphate; trimeterxate; trimeterxate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride, 20-epi-1,25 dihydroxyvitamin D3; 5-ethynyluracil; abiraterone, aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; DHEA; bromineepiandrosterone; epiandrosterone; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTSA, arginine deaminase; asulacrine; atamestane; atrimustine; axinastatin 1; axinastatin 2; axinastatin 3; azasetron; azatoxin; azatyrosine; baccatin III derivatives; balanol; batimastat, BCR/ABL antagonists; benzochlorins; benzoylstaursporine; beta lactam derivatives; beta-alethine; betaclamycin B; betulinic acid; bFGF inhibitor, bicalutamide; bisantrene; bisazindinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthrequinones; cycloplatam; cypemycin; cytarabine ocfosfate; cytolytic factor; cytostatin; dacliximab; decitabine; dehydrodidemnin B; deslorelin; dexifostamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarbine; fenretinido; filgrastim; frnasteride; flavopiridol; flezelastine; fluasterone; fludarabine; fluorodaunorunicin hydrochloride; torfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists, interferons; interleukins; iobonguane; iododoxorubicin; ipomeanol, 4; trinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole liarozole; linear polyamine analogue; lipophilicadisaccharide peptide; lipophilic platinum compounds; lissoclinamide-7; lobaplatin, lombricine; lometerxol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphioryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulator; nitroxide antioxidant; nitrullyn; O6-benzylguanine; octreotide; okicenone; oligonucleotides; onapristone; orldarisetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaepergase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum comprex; platinum compounds; platinum-triamine coil iplex; porfimer sodium; portiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purino mucleoside phosphorylast inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitor; ras-GAP inhibitor, retalliptine demethylated; rhenium Re186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim, Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmonine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimeterxate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erytrocyte gene therapy; velaresol; venom, anti-venom, veramine; verdins; verteporfin; vinorelbine; vinxaltine; vitaxin; vorozole; zanoterone; zeniplatin; zilascorb; zinostatin stimalamer, immunostimulating drugs or therapeutic agents, their metabolites, salts and derivatives thereof, and combinations thereof.

Prostate Cancer

Carcinoma of the prostate has become a significant disease in many countries and it is the most commonly diagnosed malignancy in men in the western world, its occurrence increasing significantly with age. This increase and the recent deaths of many public figures from prostate cancer have highlighted the need to do address this cancer. It has been suggested that the wider availability of screening may limit mortality from prostate cancer.

Prostate cancer screening currently consists of a rectal examination and measurement of prostate specific antigen (PSA) levels. These methods lack specificity as digital rectal examination has considerable inter-examiner variability and PSA levels may be elevated in benign prostatic hyperplasia (BPH), prostatic inflammation and other conditions. The comparative failure of PSA as a diagnostic test was shown in 366 men who developed prostate cancer while being included in the Physicians Health Study, a prospective study of over 22,000 men. PSA levels were measured in serum, which was stored at the start of the study, and elevated levels were found in only 47% of men developing prostate cancer within the subsequent four years (Gann et al, JAMA 273, 289-294, 1995).

Prostate cancers can be scored using the Gleason system, as well known to those skilled in the art (Gleason et al., Cancer Chemother Rep 50, 125-128, 1966). This uses tissue architecture rather than cytological features. A grade of 1 to 5 (well to poorly differentiated) is used, and the combined score of the most frequent and more severe areas of the lesion are combined. Gleason scores provide prognostic information that may be valuable in addition to the assessment of the stage of the tumor (staging). Gleason scores of 2 to 4 and 8 to 10 have good predictive value, but about three quarters of tumors have intermediate values.

Two principal systems are used for staging prostate cancer: TNM and the Jewett system (Benson & Olsson et al., In The Prostate, ed. Fitzpatrick, J. M. and Krane R. J., pp 261-272, Edinburgh, Churchill Livingstone 1989). Staging takes in to account any metastatic spread of the tumor and is difficult, because it is difficult to assess either local lymph node involvement or local invasion. Tumor size is also difficult to measure as tumor tissue cannot be distinguished macroscopically from normal prostate tissue, and because the prostate gland lacks a distinct capsule and is surrounded by a layer of fibrous fatty tissue.

Four categories describe the prostate tumor's (T) stage, ranging from T1 to T4. For T1, the cancer is microscopic, unilateral and non palpable. The doctor can't feel the tumor or see it with imaging such as transrectal ultrasound. Treatment for BPH may have disclosed the disease, or it was confirmed through the use of a needle biopsy done because of an elevated PSA. For T2, the doctor can feel the cancer with a DRE. It appears the disease is confined to the prostate gland on one or both sides of the gland. For T3, the cancer has advanced to tissue immediately outside the gland. For T4, the cancer has spread to other parts of the body.

Present screening methods are therefore unsatisfactory; there is no reliable method for diagnosing the cancer, or predicting or preventing its possible metastatic spread, which is the main cause of death for most patients.

PAX2

PAX genes are a family of nine developmental control genes coding for nuclear transcription factors. They play an important role in embryogenesis and are expressed in a very ordered temporal and spatial pattern. They all contain a "paired box" region of 384 base pairs encoding a DNA binding domain which is highly conserved throughout evolution (Stuart et al., Ann. Rev. Gen., 28(219):219-236, 1994). The influence of PAX genes on developmental processes has been demonstrated by the numerous natural mouse and human syndromes that can be attributed directly to even a heterozygous insufficiency in a PAX gene.

The PAX2 sequence has been disclosed (Dressler et al., Development 109, 787-795, 1990). The amino acid sequences of the human PAX2 protein and its variants, as well as the DNA sequences encoding the proteins, are listed in SEQ ID NOS: 39-50 (SEQ ID NO:39, amino acid sequence encoded by exon 1 of the human PAX2 gene; SEQ ID NO:40, human PAX2 gene promoter and exon 1; SEQ ID NO:41, amino acid sequence of the human PAX2; SEQ ID NO:42, human PAX2 gene; SEQ ID NO:43, amino acid sequence of the human PAX2 gene variant b; SEQ ID NO:44, human PAX2 gene variant b; SEQ ID NO:45, amino acid sequence of the human PAX2 gene variant c; SEQ ID NO:46, human PAX2 gene variant c; SEQ ID NO:47, amino acid sequence of the human PAX2 gene variant d; SEQ ID NO:48, human PAX2 gene variant d; SEQ ID NO:49, amino acid sequence of the human PAX2 gene variant e; SEQ ID NO:50 human PAX2 gene variant e).

PAX proteins bind specific DNA sequences through domains called a "paired domain" and, in some cases, a "homeodomain". The paired domain (PD) is a consensus sequence shared by all PAX proteins, including PAX2. The PD directs DNA binding of amino acids located in the α3-helix forming a DNA-protein complex.

It has been reported that PAX2 suppresses DEFB-1 expression by binding to the DEFB-1 promoter (Bose S K et al., Mol. Immunol. 2009, 46:1140-8) at a 5'-CCTTG-3' (SEQ ID NO:1) recognition site just upstream of the DEFB1 TATA box. For PAX2, the amino acids in the paired domain recognize and interact specifically with a CCTTG (SEQ ID NO:1) DNA core sequence in the DEFB1 promoter. Oligonucleotides up to and exceeding 64 bases in length, which include this sequence or its complement are expected to be inhibitors. Examples of cancers in which PAX2 expression has been detected are listed in Table 1.

TABLE 1

| PAX2-expressing cancers | | | | |
| --- | --- | --- | --- | --- |
| PAX2 Expressing Cancers | Estimated New Cases in US | Estimated Deaths in US | Estimated New Cases Global | Estimated Deaths Global |
| Prostate | 234,460 | 27,350 | 679,023 | 221,002 |
| Breast | 214,600 | 41,430 | 1,151,298 | 410,712 |
| Ovarian | 20,180 | 15,310 | 204,500 | 124,860 |
| Renal | 38,890 | 12,840 | 208,479 | 101,895 |
| Brain | 12,820 | 18,820 | 189,485 | 141,650 |
| Cervical | 9,710 | 3,700 | 493,243 | 273,505 |
| Bladder | 61,420 | 13,060 | 356,556 | 145,009 |
| Leukemia | 35,020 | 22,280 | 300,522 | 222,506 |
| Kaposi Sarcoma | Data Not Available | Data Not Available | Data Not Available | Data Not Available |
| TOTAL(approx.) | 627,100 | 154,790 | 3,583,106 | 1,641,139 |

EN2

The EN1 and EN2 genes, homologues of the mouse and *drosophila* segmentation gene Engrailed, encode homeodomain transcription factors (Joyner, Trends Genet., 12:15-20, 1996). PAX and EN genes are the part of genetic networks that control the development of brain and occupy a prominent position in the developmental regulatory hierarchy (Joyner, 1996). Studies in *Xenopus* suggest that EN2 and PAX2 are essential for the expression of *Xenopus* wnt-1 and for signalling through the wnt/β-catenin pathway (Koenig et al., Dev. Biol., 340:318-328, 2010).

EN2 was identified as a candidate oncogene in human breast cancer (Martin et al., Oncogene, 24:6890-901, 2005) and its expression has been found to be deregulated in pediatric brain tumor and acute myeloid leukemia (AML) (Kozmik et al., Proc. Natl. Acad. Sci. USA. 92:5709-13, 1995; Nagel et al., Genes Chromosomes Cancer, 42:170-8, 2005). Other studies have shown that *Xenopus* EN2 binds to eukaryotic initiation factor 4E (eIF4E) and triggers rapid phosphorylation of eIF4E and eIF4E-binding protein (Brunet, 2005). eIF4E is typically found in translational machinery and is a target for cancer therapy (Graff et al., Cancer Res., 68(3):631-634, 2008). Recent studies have shown that eIF4E phosphorylation promotes tumorigenesis and is associated with prostate cancer progression (Furic et al., PNAS, 107 (32):14134-39, 2010).

The amino acid sequences of the human EN2 protein and the human EN2 mRNAgene sequences are listed in SEQ ID NOS: 99 and 100, respectively.

DEFB1

β-defensins are cationic peptides with broad-spectrum antimicrobial activity that are products of epithelia and leukocytes (Ganz and Weiss, Semin Hematol., 34(4):343-54, 1997). These two-exon, single gene products are expressed at epithelial surfaces and secreted at sites including the skin. To date, five β-defensin genes of epithelial origin have been identified and characterized in humans: DEFB1 (Bensch et al., FEBS Lett., 368(2):331-5, 1995), DEFB2 (Harder et al., Genomics, 46(3):472-5, 1997), DEFB3 (Harder et al., J. Biol. Chem., 276(8):5707-13, 2001; Jia et al., Gene, 263(1-2):211-8, 2001), DEFB4, and HE2/EP2.

The amino acid sequence of human DEFB1 (or hBD-1) and the 5' regulatory sequence of the human DEFB1 gene sequence, including 644 nucleotides upstream of the transcriptional start site, are shown in SEQ ID NOS:63 and 64, respectively. The primary structure of each β-defensin gene product is characterized by small size, a six cysteine motif, high cationic charge and exquisite diversity beyond these features. The most characteristic feature of defensin proteins is their six-cysteine motif that forms a network of three disulfide bonds. The three disulfide bonds in the β-defensin proteins are between C1-C5, C2-C4 and C3-C6. The most common spacing between adjacent cysteine residues is 6, 4, 9, 6, 0. The spacing between the cysteines in the β-defensin proteins can vary by one or two amino acids except for C5 and C6, located nearest the carboxy terminus. In all known vertebrate β-defensin genes, these two cysteine residues are adjacent to each other.

A second feature of the β-defensin proteins is their small size. Each β-defensin gene encodes a preprotein that ranges in size from 59 to 80 amino acids with an average size of 65 amino acids. This gene product is then cleaved by an unknown mechanism to create the mature peptide that ranges in size from 36 to 47 amino acids with an average size of 45 amino acids. The exceptions to these ranges are the EP2/HE2 gene products that contain the β-defensin motif and are expressed in the epididymis.

A third feature of β-defensin proteins is the high concentration of cationic residues. The number of positively charged residues (arginine, lysine, histidine) in the mature peptide ranges from 6 to 14 with an average of 9.

A further feature of the β-defensin gene products is their diverse primary structure but apparent conservation of tertiary structure. Beyond the six cysteines, no single amino acid at a given position is conserved in all known members of this protein family. However, there are positions that are conserved that appear to be important for secondary and tertiary structures and function.

Despite the great diversity of the primary amino acid sequence of the β-defensin proteins, the limited data suggests that the tertiary structure of this protein family is conserved. The structural core is a triple-stranded, antiparallel β-sheet, as exemplified for the proteins encoded by BNBD-12 and DEFB2. The three β-strands are connected by a β-turn, and anα-hairpin loop, and the second β-strand also contains a β-bulge. When these structures are folded into their proper tertiary structure, the apparently random sequence of cationic and hydrophobic residues are concentrated into two faces of a globular protein. One face is hydrophilic and contains many of the positively charged side chains and the other is hydrophobic. In solution, the HBD-2 protein encoded by the DEFB2 gene exhibited anα-helical segment near the N-terminus not previously ascribed to solution structures of alpha-defensins or to the β-defensin BNBD-12. The amino acids whose side chains are directed toward the surface of the protein are less conserved between β-defensin proteins while the amino acid residues in the three β-strands of the core β-sheet are more highly conserved.

β-defensin peptides are produced as pre-pro-peptides and then cleaved to release a C-terminal active peptide fragment; however, the pathways for the intracellular processing, storage and release of the human β-defensin peptides in airway epithelia are unknown.

DEFB1's gene locus (8p23.3) is a hotspot for deletions and has been linked to patients with poorer prognosis. Thus, DEFB1 (and perhaps PAX2) can be used as a biomarker, e.g., in a screening for the early detection of prostate cancer. Furthermore, data presented indicate that its loss may occur as early as PIN (or even before), and may be a major contributing factor to the onset of prostate cancer.

PAX proteins are a family of transcription factors conserved during evolution and able to bind specific DNA sequences through a domains called a "paired domain" and a "homeodomain". The paired domain (PD) is a consensus sequence shared by certain PAX proteins (e.g., PAX2 and PAX6). The PD directs DNA binding of amino acids located in the α3-helix forming a DNA-Protein complex. For PAX2, the amino acids in the HD recognize and interact specifically with a CCTTG (SEQ ID NO:1) DNA core sequence. Oligonucleotides including this sequence or its complement are expected to be inhibitors. A critical DNA region in the DEFB1 promoter for PAX2 protein binding has the sequence of AAGTTCACCCTTGACTGTG (SEQ ID NO: 16).

In one embodiment, the oligonucleotide has the sequence of V-CCTTG-W (SEQ ID NO: 17), wherein V and W are nucleotide sequences of 1 to 35 nucleotides. In certain embodiments, V or W or both comprise contiguous nucleotide sequences that normally flank the CCTTG sequence of the DEFB1 promoter shown in SEQ ID NO: 16. Alternatively, the nucleotide sequences of V and/or W may be unrelated to the DEFB1 promoter, and selected randomly to avoid interference with the PAX2 recognition sequence.

Other examples of oligonucleotides that inhibit PAX2 binding to the DEFB1 promoter include, but are not limited to, oligonucleotide having the sequences of (5' to 3' direction):

CTCCCTTCAGTTCCGTCGAC, (SEQ ID NO: 18)

CTCCCTTCACCTTGGTCGAC, (SEQ ID NO: 19)

ACTGTGGCACCTCCCTTCAGTTCCGTCGACGAGGTTGTGC, (SEQ ID NO: 20)

ACTGTGGCACCTCCCTTCACCTTGGTCGACGAGGTTGTGC, (SEQ ID NO: 21)

ACCCTTGAC, (SEQ ID NO: 101)

TCACCCTTGACTG, (SEQ ID NO: 102)

GTTCACCCTTGACTGTG, (SEQ ID NO: 103)

AGAAGTTCACCCTTGACTGT, (SEQ ID NO: 25)

GCGATTAGAAGTTCACCCTTGACTGTGGC (SEQ ID NO: 104)

GCGATTAGAAGTTCACCCTTGACTGTGGCACCT. (SEQ ID NO: 105)

TTAGCGATTAGAAGTTCACCCTTGACTGTGGCACCTCCC (SEQ ID NO: 28)

Antisense molecules can be designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant (Kd) less than or equal to $10^{-6}$, $10^{-8}$, $10^{-10}$, or $10^{-12}$.

Nucleic Acid Delivery

Nucleic acid based inhibitors of EN2/PAX2 expression or activity, as well as nucleic acid based activators of DEFB1 expression or activity may be delivered to prostate target cells using suitable expression vectors well known to those of skill in the art. As used herein, the term "expression vector" includes any nucleic acid capable of directing expression of a nucleic acid. As such, the term "expression vector" includes viral vectors, plasmid vector, and the like. Expression vectors may be delivered to cells using two primary delivery schemes: viral-based delivery systems using viral vectors and non-viral based delivery systems using, for example, plasmid vectors. Such methods are well known in the art and readily adaptable for use with the compositions and methods described herein. In certain cases, these methods can be used to target certain diseases and cell populations by using the targeting characteristics inherent to the carrier or engineered into the carrier.

The nucleic acids that are delivered to cells contain one or more transcriptional regulatory elements, including promoters and/or enhancers, for directing the expression of exogenous genes, such as EN2 and PAX2. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

Preferred promoters are those capable of directing expression in prostate cells, especially those upregulated in prostate cancer cells. The promoters may include constitutive promoters (e.g., HCMV or SV40) or those exhibiting preferential expression in prostate cells or prostate cancer cells. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in prostate cells, prostate cancer cells, and/or in response to androgen signalling or androgen deprivation.

The promotor and/or enhancer may be specifically activated either by light or specific chemical inducing agents. In some embodiments, inducible expression systems regulated by administration of tetracycline or dexamethasone, for example, may be used. In other embodiments, gene expression may be enhanced by exposure to radiation, including gamma irradiation and external beam radiotherapy (EBRT), or alkylating chemotherapeutic drugs.

Prostate-specific transcriptional regulatory elements (TREs) can be incorporated into expression vectors to allow for transcriptional targeting of expression in pre-cancerous and/or cancerous prostate cells. Exemplary prostate-specific TREs include native TREs and chrimeric TREs comprising one or more regulatory elements from prostate-specific antigen (PSA or hk3), prostate-specific membrane antigen (PSMA), probasin (PB), glandular kallikrein-2 (hk2) genes, osteocalcin, chimeric PSA-PSMA or (PSE) as described in U.S.Patent Application Publication No. 2003/0235874, as well as one or more exogenously added androgen responsive regulatory elements, in addition to those that may already be present.

PSA, probasin, and glandular kallikrein TREs are androgen-inducible and are preferably utilized for sense DEFB1 and/or antisense expression of EN2/PAX2 in androgen-sensitive cells. Conversely, PMSA TREs are specifically induced by androgen deprivation and are preferably utilized for expression in castration-resistant prostate cells.

In one embodiment, high level prostate-specific expression of nucleic acids may be achieved using a prostate-specific two-step transcriptional amplification (TSTA) system two-tiered amplification described by Sato et al., Gene Ther., 15(8):583-593, 2008 and as described in U.S. Patent Application Publication No. 2006/0223141, the disclosures of which are incorporated by reference herein.

Expression vectors generally contain sequences for transcriptional termination, and may additionally contain one or more elements positively affecting mRNA stability. An expression vector may further include an internal ribosome entry site (IRES) between adjacent protein coding regions to facilitate expression two or more proteins from a common mRNA in an infected or transfected cell. Additionally, the expression vectors may further include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

Viral-Based Delivery Systems

In some embodiments, the inhibitors or activators of the herein described bioactive components are delivered as genetically engineered viruses using virus-derived expression vectors. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses, and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers, and can be delivered in aerosol formulation, and can transfect non-dividing cells. Poxyiral vectors are large and have several sites for inserting genes, they are thermostable and can be stored at room temperature. Viral delivery systems typically utilize viral vectors having one or more genes removed and with and an exogenous gene and/or gene/promotor cassette being inserted into the viral genome in place of the removed viral DNA. The necessary functions of the removed gene(s) may be supplied by cell lines which have been engineered to express the gene products of the early genes in trans.

Viral vectors for prostate-specific tissue targeting and/or expression have been described. See e.g., Zhang et al., Cancer Gene Ther., 16:820-831, 2009; Trujillo et al., Gene Ther., 17(11):1325-1332, 2010; Kraaij et al., Prostate, 67(8):829-839, 2007; and U.S. Patent Application Publication Nos. 2008/0247996 and 2009/0130061, the disclosures of which are incorporated by reference herein.

In some embodiments, nonviral delivery systems are utilized for delivery of plasmid vectors or other non nucleic acid bioactive agents using lipid formulations comprising, for example, liposomes, such as cationic liposomes (e.g., DOTMA, DOPE, DC-cholesterol) and anionic liposomes. Liposomes can be further conjugated to one or more proteins or peptides to facilitate targeting to a particular cell, if desired. Administration of a composition comprising a compound and a cationic liposome can be administered to the blood afferent to a target organ or inhaled into the respiratory tract to target cells of the respiratory tract. Furthermore, a bioactive agent can be administered as a component of a microcapsule or nanoparticle that can be targeted to prostate cancer cells using targeting moities described herein or that can be designed for slow release of one or more bioactive agent(s) in accordance with a predetermined rate of release or dosage.

In other embodiments, the nucleic acids may be delivered in vivo by electroporation, the technology for which is available from Genetronics, Inc. (San Diego, Calif.) as well as by means of a SONOPORATION™ machine (ImaRx Pharmaceutical Corp., Tucson, Ariz.).

The bioactive components may be in solution or suspension (for example, incorporated into microparticles, liposomes, or cells). These may be targeted to a particular cell type via antibodies, receptors, or receptor ligands. Vehicles such as "stealth" and other antibody conjugated liposomes (including lipid mediated drug targeting to prostate cells), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

The present invention is further illustrated by the following examples which should not be construed as limiting. The contents of all references, patents and published patent applications cited throughout this application, as well as the Figures and Tables are incorporated herein by reference.

EXAMPLE 1

Human Beta Defensin-1 is Cytotoxic to Late-Stage Prostate Cancer and Plays a Role in Prostate Cancer Tumor Immunity In this example, DEFB1 was cloned into an inducible expression system to examine what effect it had on normal prostate epithelial cells, as well as androgen receptor positive (AR+) and androgen receptor negative (AR−) prostate cancer cell lines. Induction of DEFB1 expression resulted in a decrease in cellular growth in AR− cells DU145 and PC3, but had no effect on the growth of the AR+prostate cancer cells LNCaP. DEFB1 also caused rapid induction of caspase-mediated apoptosis. Data presented are the first to provide evidence of its role in innate tumor immunity and indicate that its loss contributes to tumor progression in prostate cancer.

1.1 Materials and Methods

Cell lines: The cell lines DU145 were cultured in DMEM medium, PC3 were grown in F12 medium, and LNCaP were grown in RPMI medium (Life Technologies, Inc., Grand Island, N.Y.). Growth media for all three lines was supplemented with 10% (v/v) fetal bovine serum (Life Technologies). The hPrEC cells were cultured in prostate epithelium basal media (Cambrex Bio Science, Inc., Walkersville, Md.). All cell lines were maintained at 37° C. and 5% $CO_2$.

Tissue samples and laser capture microdissection: Prostate tissues obtained from consented patients that underwent radical prostatectomy were acquired through the Hollings Cancer Center tumor bank in accordance with an Institutional Review Board-approved protocol. This included guidelines for the processing, sectioning, histological characterization, RNA purification and PCR amplification of samples. Following pathologic examination of frozen tissue sections, laser capture microdissection (LCM) was performed to ensure that the tissue samples assayed consisted of pure populations of benign prostate cells. For each tissue section analyzed, LCM was performed at three different regions containing benign tissue and the cells collected were then pooled.

Prostate tissues were obtained from patients who provided informed consent prior to undergoing radical prostatectomy. Samples were acquired through the Hollings Cancer Center tumor bank in accordance with an Institutional Review Board-approved protocol. This included guidelines for the processing, sectioning, histological characterization, RNA purification and PCR amplification of samples. Prostate specimens received from the surgeons and pathologists were immediately frozen in OCT compound. Each OCT block was cut to produce serial sections which were stained and examined. Areas containing benign cells, prostatic intraepithelial neoplasia (PIN), and cancer were identified and used to guide our selection of regions from unstained slides using the Arcturus PixCell II System (Sunnyvale, Calif.). Caps containing captured material were exposed to 20 µl of lysate from the Arcturus Pico Pure RNA Isolation Kit and processed immediately. RNA quantity and quality was evaluated using sets of primers that produce 5' amplicons. The sets include those for the ribosomal protein L32 (the 3' amplicon and the 5' amplicon are 298 bases apart), for the glucose phosphate isomerase (391 bases apart), and for the glucose phosphate isomerase (842 bases apart). Ratios of 0.95 to 0.80 were routinely obtained for these primer sets using samples from a variety of prepared tissues. Additional tumor and normal samples were grossly dissected by pathologists, snap frozen in liquid nitrogen and evaluated for hBD-1 and cMYC expression.

Cloning of DEFB1 gene: DEFB1 cDNA was generated from RNA by reverse transcription-PCR. The PCR primers harvested by trypsinizing. Cells were lysed and total RNA was isolated by centrifugation through spin columns. For cells collected by LCM, total RNA was isolated using the PicoPure RNA Isolation Kit (Arcturus Biosciences, Mt. View, Calif.) following the manufacturer's protocol. Total RNA (0.5 µg per reaction) from both sources was reverse transcribed into cDNA utilizing random primers (Promega). AMV Reverse Transcriptase II enzyme (500 units per reaction; Promega) was used for first strand synthesis and Tfl DNA Polymerase for second strand synthesis (500 units per reaction; Promega) as per the manufacturer's protocol. In each case, 50 pg of cDNA was used per ensuing PCR reaction. Two-step QRT-PCR was performed on cDNA generated using the MultiScribe Reverse Transcripatase from the TaqMan Reverse Transcription System and the SYBR® Green PCR Master Mix (Applied Biosystems).

The primer pair for DEFB1 was generated from the published DEFB1 sequence (GenBank Accession No. U50930). The primer sequences are:

TABLE 2

Primer pairs for DEFB1 and β-actin

| | Sense (5'-3') | |
|---|---|---|
| β-actin | 5'-CCTGGCACCCAGCACAAT-3' | SEQ ID NO: 51 |
| DEFB1 | 5'-GTTGCCTGCCAGTCGCCATGAGAACTTCCTAC-3' | SEQ ID NO: 53 |
| | Antisense (5'-3') | |
| β-actin | 5'-GCCGATCCACACGGAGTACT-3' | SEQ ID NO: 52 |
| DEFB1 | 5'-TGGCCTTCCCTCTGTAACAGGTGCCTTGAATT-3' | SEQ ID NO: 54 | were designed to contain ClaI and KpnI restriction sites. DEFB1 PCR products were restriction digested with ClaI and KpnI and ligated into a TA cloning vector. The TA/DEFB1 vector was then transfected into E. coli by heat shock and individual clones were selected and expanded. Plasmids were isolated as DNA Midipreps (Qiagen, Valencia, Calif.) from E. coli cultures and sequence integrity verified by automated sequencing. The DEFB1 gene fragment was then ligated into the pTRE2 digested with ClaI and KpnI, which served as an intermediate vector for orientation purposes. Then the pTRE2/DEFB1 construct was digested with ApaI and KpnI to excise the DEFB1 insert, which was ligated into pIND vector of the Ecdysone Inducible Expression System (Invitrogen, Carlsbad, Calif.) also double digested with ApaI and KpnI. The construct was again transfected into E. coli and individual clones were selected and expanded. Plasmids were isolated and sequence integrity of pIND/DEFB1 was again verified by automated sequencing.

Cell transfections: Cells ($1 \times 10^6$) were seeded onto 100-mm Petri dishes and grown overnight. Then the cells were co-transfected using Lipofectamine 2000 (Invitrogen, Carlsbad, Calif.) with 1 µg of pVgRXR plasmid, which expresses the heterodimeric ecdysone receptor, and 1 µg of the pIND/DEFB1 vector construct or empty pIND control vector in Opti-MEM media (Life Technologies, Inc., Grand Island, N.Y.).

RNA isolation and quantitative RT-PCR: In order to verify DEFB1 protein expression in the cells transfected with DEFB1 construct, RNA was collected after a 24 hour induction period with Ponasterone A (Pon A). Briefly, total RNA was isolated using the SV Total RNA Isolation System (Promega, Madison, Wis.) from approximately $1 \times 10^6$ cells Forty cycles of PCR were performed under standard conditions using an annealing temperature of 56° C. In addition, β-actin (Table 2) was amplified as a housekeeping gene to normalize the initial content of total cDNA. DEFB1 expression was calculated as the relative expression ratio between DEFB1 and β-actin and was compared in cells lines induced and uninduced for DEFB1 expression, as well as LCM benign prostatic tissue. As a negative control, QRT-PCR reactions without cDNA template were also performed. All reactions were run three times in triplicate.

MTT cell viability assay: To examine the effects of DEFB1 on cell growth, metabolic 3-[4,5-dimethylthiazol-2yl]-2,5 diphenyl tetrazolium bromide (MTT) assays were performed. PC3, DU145 and LNCaP cells co-transfected with pVgRXR plasmid and pIND/DEFB1 construct or empty pIND vector were seeded onto a 96-well plate at $1-5 \times 10^3$ cells per well. Twenty-four hours after seeding, fresh growth medium was added containing 10 µM Ponasterone A daily to induce DEFB1 expression for 24-, 48- and 72 hours after which the MTT assay was performed according to the manufacturer's instructions (Promega). Reactions were performed three times in triplicate.

Flow cytometry: PC3 and DU145 cells co-transfected with the DEFB1 expression system were grown in 60-mm dishes and induced for 12, 24, and 48 hours with 10 µM Ponasterone A. Following each incubation period, the medium was collected from the plates (to retain any detached cells) and combined with PBS used to wash the plates. The remaining attached cells were harvested by trypsinization and combined with the detached cells and PBS. The cells were then pelleted at 4° C. (500×g) for 5 min, washed twice in PBS, and resuspended in 100 µl of 1×Annexin binding buffer (0.1 M Hepes/

NaOH at pH 7.4, 1.4 M NaCl, 25 mM CaCl2) containing 5 μl of Annexin V-FITC and 5 μl of PI. The cells were incubated at RT for 15 min in the dark, then diluted with 400 μl of 1× Annexin binding buffer and analyzed by FACscan (Becton Dickinson, San Jose, Calif.). All reactions were performed three times.

Microscopic analysis: Cell morphology was analyzed by phase contrast microscopy. DU145, PC3 and LNCaP cells containing no vector, empty plasmid or DEFB1 plasmid were seeded onto 6 well culture plates (BD Falcon, USA). The following day plasmid-containing cells were induced for a period of 48 h with media containing 10 μM Ponasterone A, while control cells received fresh media. The cells were then viewed under an inverted Zeiss IM 35 microscope (Carl Zeiss, Germany). Phase contrast pictures of a field of cells were obtained using the SPOT Insight Mosaic 4.2 camera (Diagnostic Instruments, USA). Cells were examined by phase contrast microscopy under 32× magnification and digital images were stored as uncompressed TIFF files and exported into Photoshop CS software (Adobe Systems, San Jose, Calif.) for image processing and hard copy presentation.

Caspase detection: Detection of caspase activity in the prostate cancer cell lines was performed using APO LOGIX™ Carboxyfluorescin Caspase detection kit (Cell Technology, Mountain View, Calif.). Active caspases were detected through the use of a FAM-VAD-FMK inhibitor that irreversibly binds to active caspases. Briefly, DU145 and PC3 cells (1.5-3×105) containing the DEFB1 expression system were plated in 35 mm glass bottom microwell dishes (Matek, Ashland, Mass.) and treated for 24 hours with media only or with media containing PonA as previously described. Next, 10 μl of a 30× working dilution of carboxyfluorescein labeled peptide fluoromethyl ketone (FAM-VAD-FMK) was added to 300 μl of media and added to each 35 mm dish. Cells were then incubated for 1 hour at 37° C. under 5% CO2. Then, the medium was aspirated and the cells were washed twice with 2 ml of a 1× Working dilution Wash Buffer. Cells were viewed under differential interference contrast (DIC) or under laser excitation at 488 nm. The fluorescent signal was analyzed using a confocal microscope (Zeiss LSM 5 Pascal) and a 63×DIC oil lens with a Vario 2 RGB Laser Scanning Module.

Statistical analysis: Statistical differences were evaluated using the Student's t-test for unpaired values. P values were determined by a two-sided calculation, and a P value of less than 0.05 was considered statistically significant.

1.2 Results

Figure 1B:
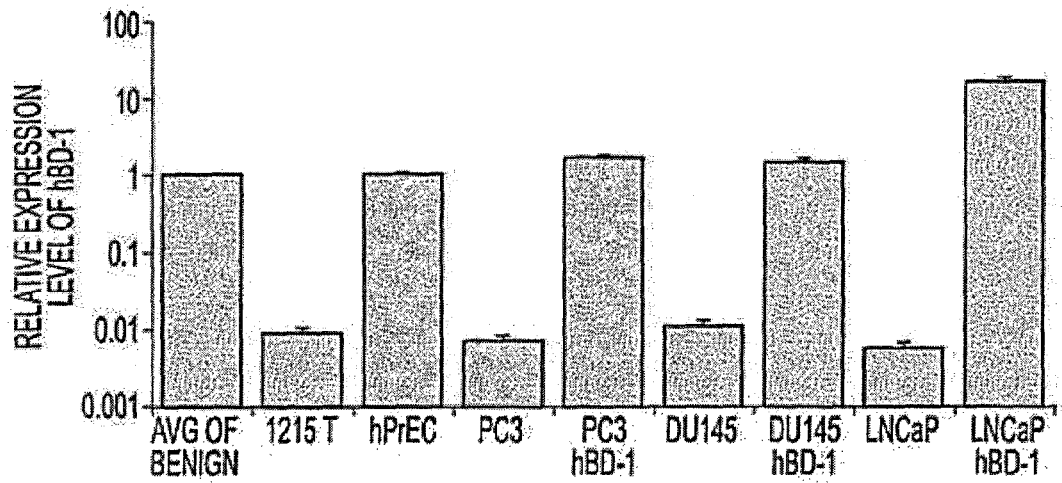

DEFB1 expression in prostate tissue and cell lines: DEFB1 expression levels were measured by QRT-PCR in benign and malignant prostatic tissue, hPrEC prostate epithelial cells and DU145, PC3 and LNCaP prostate cancer cells. DEFB1 expression was detected in all of the benign clinical samples. The average amount of DEFB1 relative expression was 0.0073. In addition, DEFB1 relative expression in hPrEC cells was 0.0089. There was no statistical difference in DEFB1 expression detected in the benign prostatic tissue samples and hPrEC (FIG. 1A). Analysis of the relative DEFB1 expression levels in the prostate cancer cell lines revealed significantly lower levels in DU145, PC3 and LNCaP. As a further point of reference, relative DEFB1 expression was measured in the adjacent malignant section of prostatic tissue from patient #1215. There were no significant differences in the level of DEFB1 expression observed in the three prostate cancer cell lines compared to malignant prostatic tissue from patient #1215 (FIG. 1B). In addition, expression levels in all four samples were close to the no template negative controls which confirmed little to no endogenous DEFB1 expression (data not shown). QRT-PCR was also performed on the prostate cancer cell lines transfected with the DEFB1 expression system. Following a 24 hour induction period, relative expression levels were 0.01360 in DU145, 0.01503 in PC3 and 0.138 in LNCaP. Amplification products were verified by gel electrophoresis.

Figure 1C:
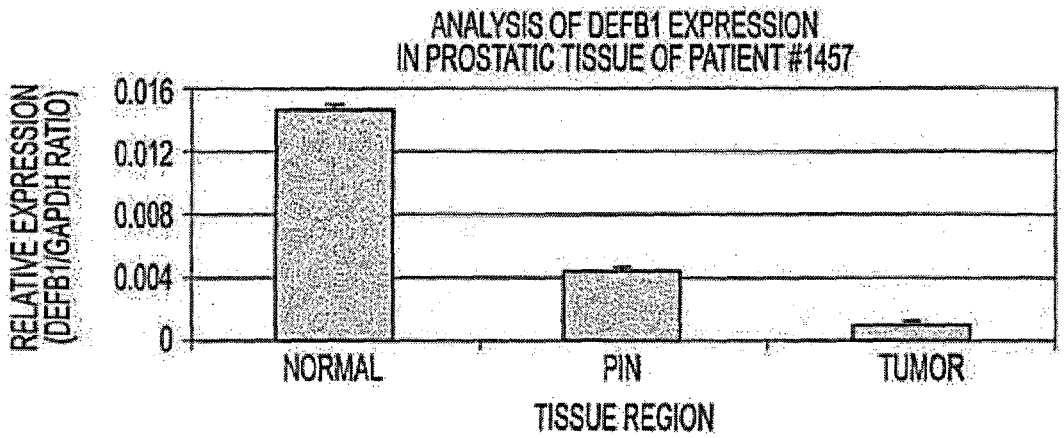
Figure 1D:
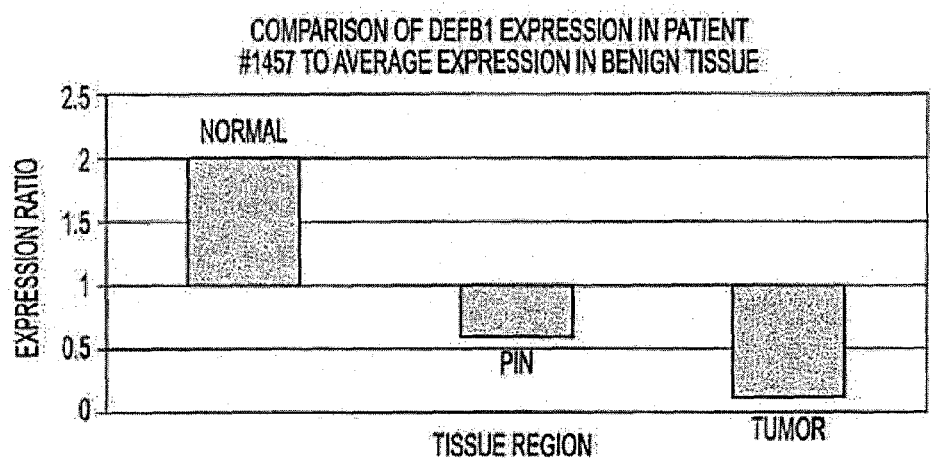

QRT-PCR was performed on prostate tissues by laser capture microdissection, including regions containing benign, PIN and cancer. DEFB1 relative expression was 0.0146 in the benign region compared to 0.0009 in the malignant region (FIG. 1C). This represents a 94% decrease which again demonstrates a significant down-regulation of expression. Furthermore, analysis of PIN revealed that DEFB1 expression level was 0.044 which was a 70% decrease. Comparing expression in patient #1457 to the average expression level found in benign regions of six other patients (FIG. 1A) revealed a ratio of 1.997 representing almost twice as much expression (FIG. 1D). However, the expression ratio was 0.0595 in PIN and was 0.125 in malignant tissue compared to average expression levels in benign tissue.

Figure 2:
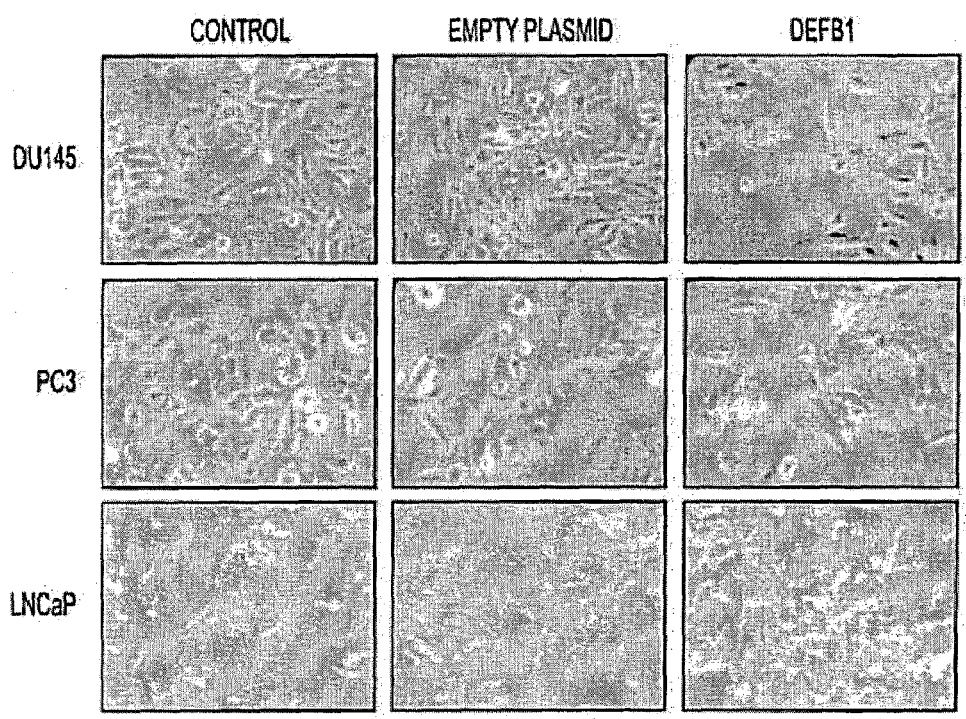
FIG. 2 shows microscopic analysis of DEFB1 induced changes in membrane integrity and cell morphology. Membrane ruffling is indicated by black arrows and apoptotic bodies are indicated white arrows.

DEFB1 causes cell membrane permeability and ruffling: Induction of DEFB1 in the prostate cancer cell lines resulted in a significant reduction in cell number in DU145 and PC3, but had no effect on cell proliferation in LNCaP (FIG. 2). As a negative control, cell proliferation was monitored in all three lines containing empty plasmid. There were no observable changes in cell morphology in DU145, PC3 or LNCaP cells following the addition of PonA. In addition, DEFB1 induction resulted in morphological changes in both DU145 and PC3. Cells appeared more rounded and exhibited membrane ruffling indicative of cell death. Apoptotic bodies were also present in both lines.

Figure 3:
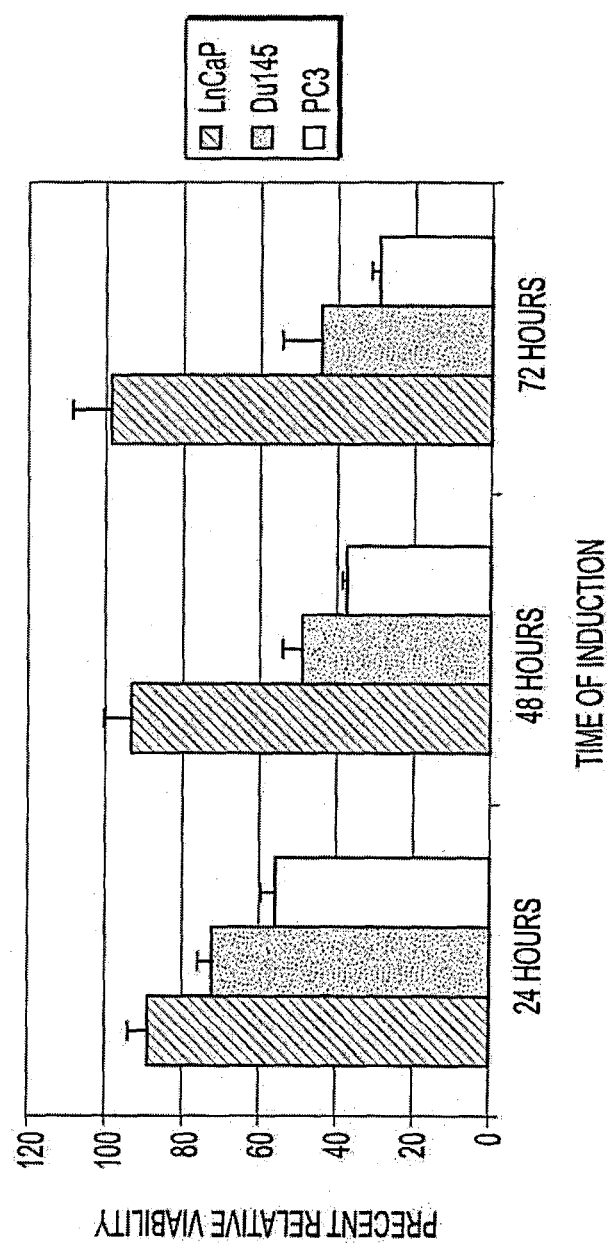
FIG. 3 shows an analysis of DEFB1 cytotoxicity in prostate cancer cell lines DU145, PC3 and LNCaP treated with PonA to induce DEFB1 expression for 1-3 days after which an MTT assay was performed to determine cell viability.

Expression of DEFB1 results in decreased cell viability: The MTT assay showed a reduction in cell viability by DEFB1 in PC3 and DU145 cells, but no significant effect on LNCaP cells (FIG. 3). After 24 hours, relative cell viability was 72% in DU145 and 56% in PC3. Analysis 48 hours after induction revealed 49% cell viability in DU145 and 37% cell viability in PC3. After 72 hours of DEFB1 expression resulted in 44% and 29% relative cell viability in DU145 and PC3 cells, respectively.

Figure 4A:
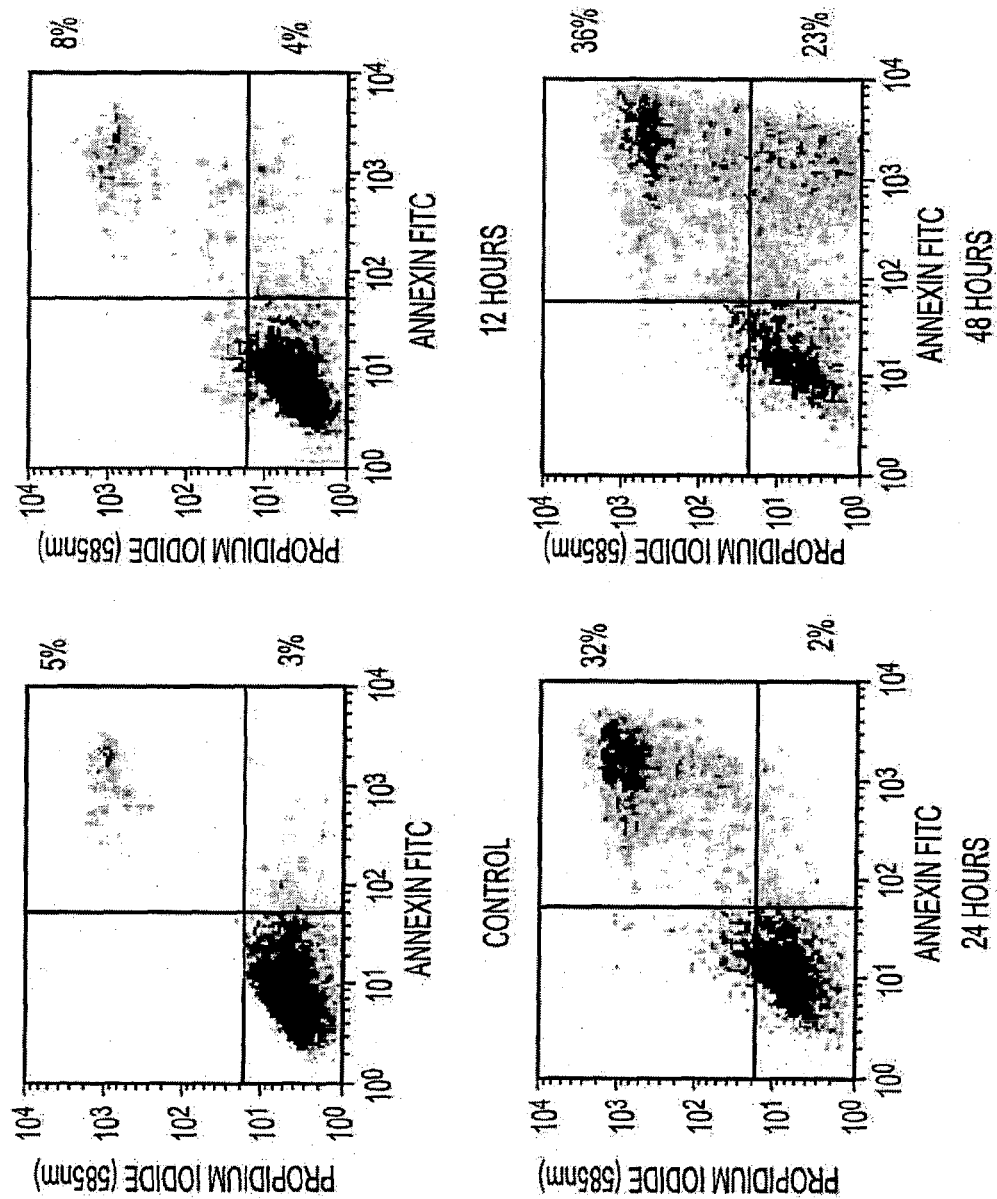
FIGS. 4A and 4B show induction of cell death in DU145 and PC3 cells by DEFB1.
Figure 4B:
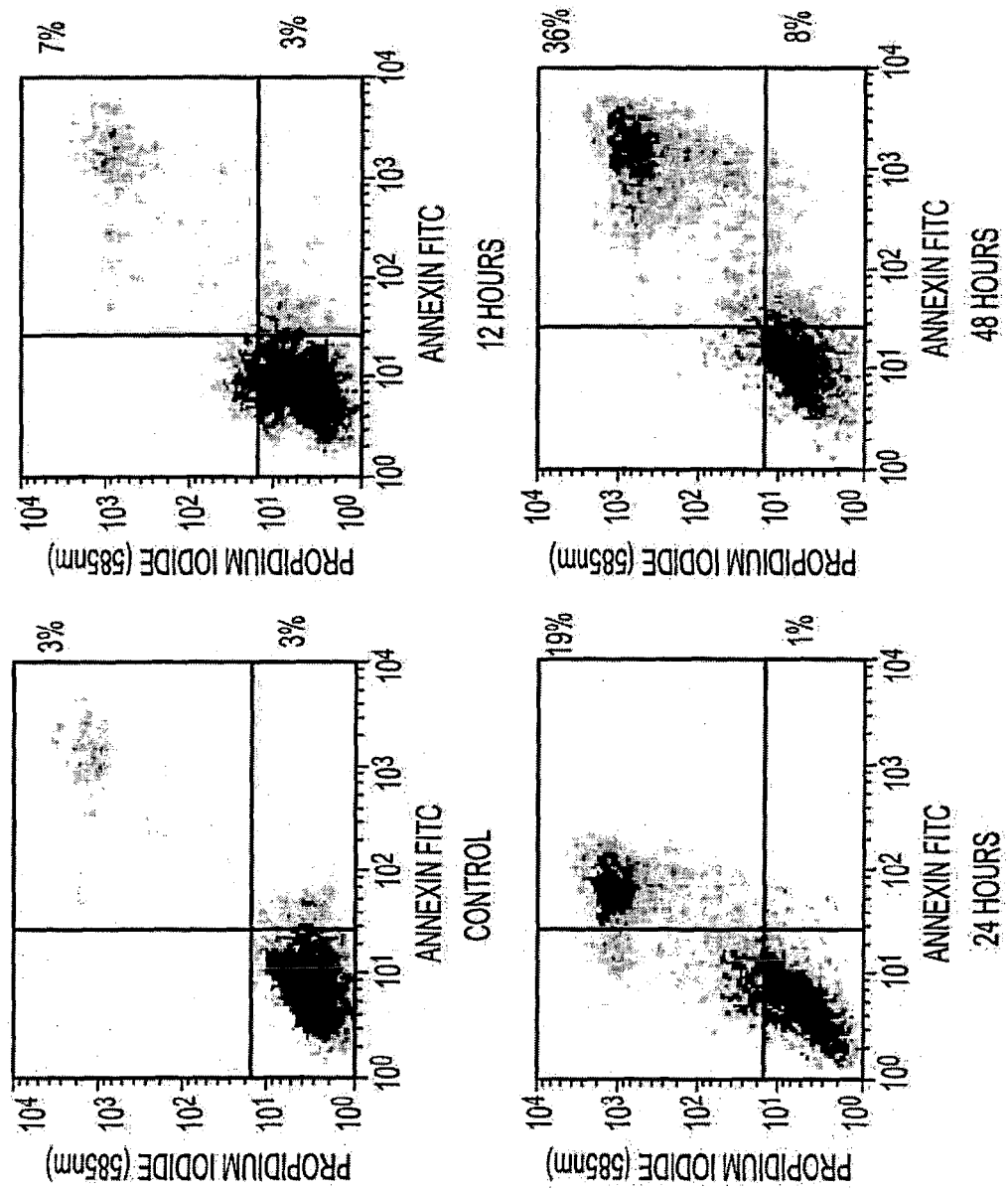

DEFB1 causes rapid caspase-mediated apoptosis in late-stage prostate cancer cells: In order to determine whether the effects of DEFB1 on PC3 and DU145 were cytostatic or cytotoxic, FACS analysis was performed. Under normal growth conditions, more than 90% of PC3 and DU145 cultures were viable and non-apoptotic (lower left quadrant) and did not stain with annexin V or PI. After inducing DEFB1 expression in PC3 cells, the number of apoptotic cells (lower and upper right quadrants) totaled 10% at 12 hours, 20% at 24 hours, and 44% at 48 hours (FIG. 4B). For DU145 cells, the number of apoptotic cells totaled 12% after 12 hours, 34% at 24 hours, and 59% after 48 hours of induction (FIG. 4A). There was no increase in apoptosis observed in cells containing empty plasmid following induction with PonA (data not shown).

Caspase activity was determined by confocal laser microscopic analysis (FIG. 5). DU145 and PC3 cell were induced for DEFB1 expression and activity was monitored based on the binding of green fluorescing FAM-VAD-FMK to caspases in cells actively undergoing apoptosis. Analysis of cells under DIC showed the presence of viable control DU145 (panel A), PC3 (panel E) and LNCaP (panel I) cells at 0 hours. Excitation by the confocal laser at 488 nm produced no detectable green staining which indicates no caspase activity in DU145 (panel B), PC3 (panel F) or LNCaP (panel J). Following induction for 24 hours, DU145 (panel C), PC3 (panel G) and LNCaP (panel K) cells were again visible under DIC. Confocal analysis under fluorescence revealed green staining in DU145 (panel D) and PC3 (panel H) cell indicating caspase activity. However, there was no green staining in LNCaP (panel L), indicating no induction of apoptosis by DEFB1.

In conclusion, this study provides the functional role of DEFB1 in prostate cancer. Furthermore, these findings show that DEFB1 is part of an innate immune system involved in tumor immunity Data presented demonstrate that DEFB1 expressed at physiological levels is cytotoxic to AR– hormone refractory prostate cancer cells, but not to AR+ hormone sensitive prostate cancer cell nor to normal prostate epithelial cells. Given that DEFB1 is constitutively expressed in normal prostate cells without cytotoxicity, it may be that late-stage AR– prostate cancer cells possess distinct phenotypic characteristics that render them sensitive to DEFB1 cytotoxicity. Thus, DEFB1 is a viable therapeutic agent for the treatment of late-stage prostate cancer, and potentially other cancers as well.

EXAMPLE 2 siRNA Mediated Knockdown of PAX2 Expression Results in Prostate Cancer Cell Death Independent of P53 Status This example examines the effects of inhibiting PAX2 expression by RNA interference in prostate cancer cells which differ in p53 gene status. The results demonstrate that the inhibition of PAX2 results in cell death irrespective of p53 status, indicating that there are additional tumor suppressor genes or cell death pathways inhibited by PAX2 in prostate cancer.

2.1 Materials and Methods siRNA silencing of PAX2: In order to achieve efficient gene silencing, a pool of four complementary short interfering ribonucleotides (siRNAs) targeting human PAX2 mRNA (Accession No. NM_003989.1), were synthesized (Dharmacon Research, Lafayette, Colo., USA). A second pool of four siRNAs were used as an internal control to test for the specificity of PAX2 siRNAs. Two of the sequences synthesized target the GL2 luciferase mRNA (Accession No. X65324), and two were non-sequence-specific (Table 3). For annealing of siRNAs, 35 M of single strands were incubated in annealing buffer (100 mM potassium acetate, 30 mM HEPES-KOH at pH 7.4, 2 mM magnesium acetate) for 1 min at 90° C. followed by 1 h incubation at 37° C.

TABLE 3

PAX2 siRNA Sequences.
A pool of four siRNA was utilized to inhibit PAX2 protein expression.

| | Sense (5'-3') | |
|---|---|---|
| Sequence A | 5'-GAAGUCAAGUCGAGUCUAUUU-3' | SEQ ID NO: 7 |
| Sequence B | 5'-GAGGAAACGUGAUGAAGAUUU-3' | SEQ ID NO: 8 |
| Sequence C | 5'-GGACAAGAUUGCUGAAUACUU-3' | SEQ ID NO: 9 |
| Sequence D | 5'-CAUCAGAGCACAUCAAAUCUU-3' | SEQ ID NO: 10 |

TABLE 3 -continued

PAX2 siRNA Sequences.
A pool of four siRNA was utilized to inhibit PAX2 protein expression.

| | Antisense (5'-3') | |
|---|---|---|
| Sequence A | 5'-AUAGACUCGACUUGACUUCUU-3' | SEQ ID NO: 3 |
| Sequence B | 5'-AUCUUCAUCACGUUUCCUCUU-3' | SEQ ID NO: 4 |
| Sequence C | 5'-GUAUUCAGCAAUCUUGUCCUU-3' | SEQ ID NO: 5 |
| Sequence D | 5'-GAUUUGAUGUGCUCUGAUGUU-3' | SEQ ID NO: 6 |

Western blot analysis: Briefly, cells were harvested by trypsinization and washed twice with PBS. Lysis buffer was prepared according to the manufacturer's instructions (Sigma), and was then added to the cells. Following a 15 minute incubation period at 4° C. on an orbital shaker, cell lysate were then collected and centrifuged for 10 minutes at 12000×g to pellet cellular debris. The protein-containing supernatant were then collected and quantitated. Next, 25 µg protein extract was loaded onto an 8-16% gradient SDS-PAGE (Novex). Following electrophoresis, proteins were transferred to PVDF membranes, and then blocked with 5% nonfat dry milk in TTBS (0.05% Tween 20 and 100 mM Tris-Cl) for 1 hour. Blots were then probed with rabbit anti-PAX2 primary antibody (Zymed, San Francisco, Calif.) at a 1:2000 dilution. After washing, the membranes were incubated with anti-rabbit antibody conjugated to horseradish peroxidase (HRP) (dilution 1:5000; Sigma), and signal detection was visualized using chemilluminescence reagents (Pierce) on an Alpha Innotech Fluorchem 8900. As a control, blots were stripped and reprobed with mouse anti-β-actin primary antibody (1:5000; Sigma-Aldrich) and HRP-conjugated anti-mouse secondary antibody (1:5000; Sigma-Aldrich) and signal detection was again visualized.

Phase contrast microscopy: The effect of PAX2 knockdown on cell growth was analyzed by phase contrast microscopy as described in Example 1.

MTT cytotoxicity assay: DU145, PC3 and LNCaP cells (1×105) were transfected with 0.5 µg of the PAX2 siRNA pool or control siRNA pool using Codebreaker transfection reagent according to the manufacturer's protocol (Promega). Next, cell suspensions were diluted and seeded onto a 96-well plate at 1-5×103 cells per well and allowed to grow for 2-, 4- or 6 days. After culture, cell viability was determined by measuring the conversion of 3-[4,5-dimethylthiazol-2yl]-2,5 diphenyl tetrazolium bromide, MTT (Promega), to a colored formazan product. Absorbance was read at 540 nm on a scanning multiwell spectrophotometer.

Pan-caspase detection: Detection of caspase activity in the prostate cancer cell lines was performed s described in Example 1.

Quantitative real-time RT-PCR: Quantitative real-time RT-PCR was performed as described in Example 1 in order to verify gene expression after PAX2 siRNA treatment in PC3, DU145 and LNCaP cell lines. The primer pairs for GAPDH (control gene), BAX, BID and BAD are:

```
Sense (5'-3')
GAPDH
                                      SEQ ID NO: 55
5'-CCACCCATGGCAAATTCCATGGCA-3'

SEQ ID NO: 57
BAD
5'-CTCAGGCCTATGCAAAAAGAGGA-3'

BID
                                      SEQ ID NO: 59
5'-AACCTACGCACCTACGTGAGGAG-3'

BAX
                                      SEQ ID NO: 61
5'-GACACCTGAGCTGACCTTGG-3'

Antisense (5'-3')
GAPDH
                                      SEQ ID NO: 56
5'-TCTAGACGGCAGGTCAGGTCAACC-3'

BAD
                                      SEQ ID NO: 58
5'-GCCCTCCCTCCAAAGGAGAC-3'

BID
                                      SEQ ID NO: 60
5'-CGTTCAGTCCATCCCATTTCTG-3'

BAX
                                      SEQ ID NO: 62
5'-GAGGAAGTCCAGTGTCCAGC-3'
```

Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Gene expression was calculated as the relative expression ratio between the pro-apoptotic genes and GAPDH. All reactions were carried out in triplicate.

Figure 6:
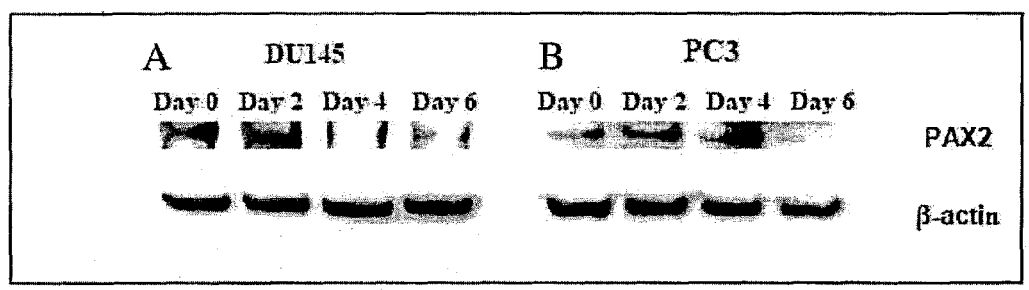
FIG. 6 shows silencing of PAX2 protein expression following PAX2 siRNA treatment.

2.2 Results siRNA inhibition of PAX2 protein expression: In order to confirm that the siRNA effective targeted the PAX2 mRNA, Western blot analysis was performed to monitor PAX2 protein expression levels over a six day treatment period. Cells were given a single round of transfection with the pool of PAX2 siRNA. The results confirmed specific targeting of PAX2 mRNA by showing knock-down of PAX2 protein by day four in DU145 (FIG. 6, panel A) and by day six in PC3 (FIG. 6, panel B).

Figure 7:
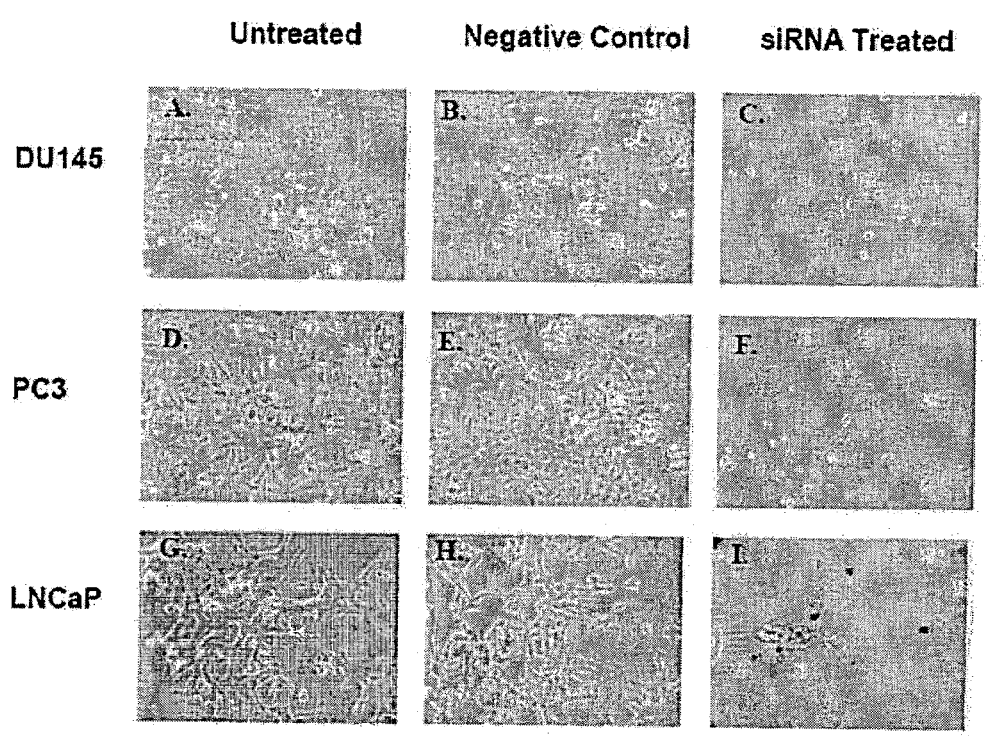
FIG. 7 shows analysis of prostate cancer cells growth after treatment with PAX2 siRNA.

Knock-down of PAX2 inhibits prostate cancer cell growth: Cells were analyzed following a six day treatment period with media only, negative control non-specific siRNA or PAX2 siRNA (FIG. 7). DU145 (panel A), PC3 (panel D) and LNCaP (panel G) cells all reached at least 90% confluency in the culture dishes containing media only. Treatment of DU145 (panel B), PC3 (panel E) and LNCaP (panel H) with negative control non-specific siRNA had no effect on cell growth, and cells again reached confluency after six days. However, treatment with PAX2 siRNA resulted in a significant decrease in cell number. DU145 cells were approximately 15% confluent (panel C) and PC3 cells were only 10% confluent (panel F). LNCaP cell were 5% confluent following siRNA treatment.

Figure 8:
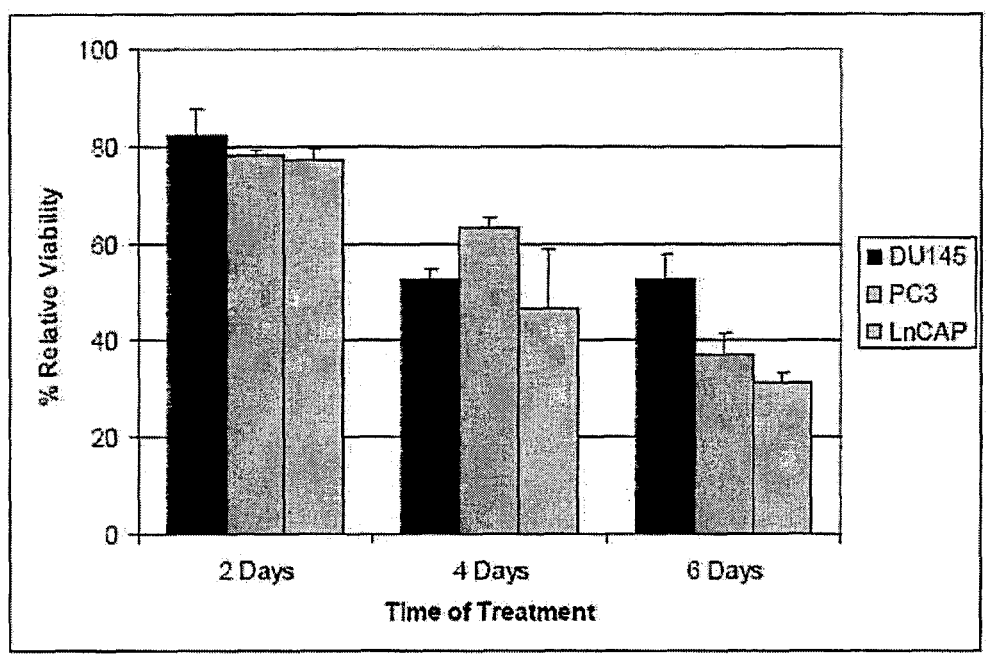
FIG. 8 shows analysis of cell death following siRNA silencing of PAX2. Results represent mean±s.d., n=9.

Cytotoxicity assays: Cell viability was measured after two-, four-, and six-day exposure times, and is expressed as a ratio of the 570-630 nm absorbance of treated cells divided by that of the untreated control cells (FIG. 8). Relative cell viability following 2 days of treatment was 77% in LNCaP, 82% in DU145 and 78% in PC3. After four days, relative cell viability was 46% in LNCaP, 53% in DU145 and 63% in PC3. After six days of treatment, relative cell viability decreased to 31% in LNCaP, 37% in PC3, and was 53% in DU145. As negative controls, cell viability was measured in after a six day treatment period with negative control non-specific siRNA or transfection reagent alone. For both conditions, there was no statistically significant change in cell viability compared to normal growth media.

Figure 9:
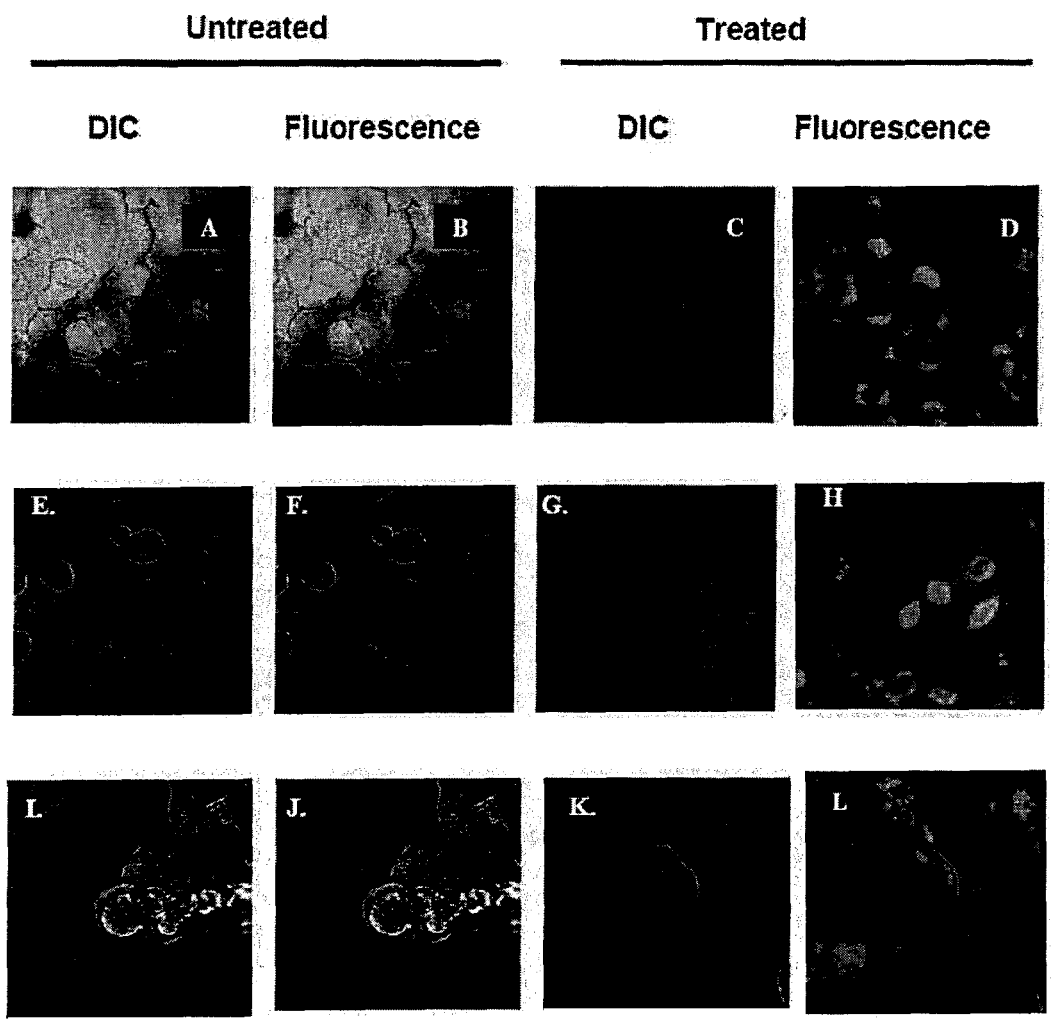
FIG. 9 shows analysis of caspase activity.

Pan-caspase detection: Caspase activity was detected by confocal laser microscopic analysis. DU145, PC3 and LNCaP cells were treated with PAX2 siRNA and activity was monitored based on the binding of FAM-labeled peptide to caspases in cells actively undergoing apoptosis which will fluoresce green. Analysis of cells with media only under DIC shows the presence of viable DU145 (A), PC3 (E) and LNCaP (I) cells at 0 hours (FIG. 9). Excitation by the confocal laser at 488 nm produced no detectable green staining which indicates no caspase activity in untreated DU145 (B), PC3 (F) or LNCaP (J). Following four days of treatment with PAX2 siRNA, DU145 (C), PC3 (G) and LNCaP (K) cells were again visible under DIC. Under fluorescence, the treated DU145 (D), PC3 (H) and LNCaP (L) cells presented green staining indicating caspase activity.

Figure 10A:
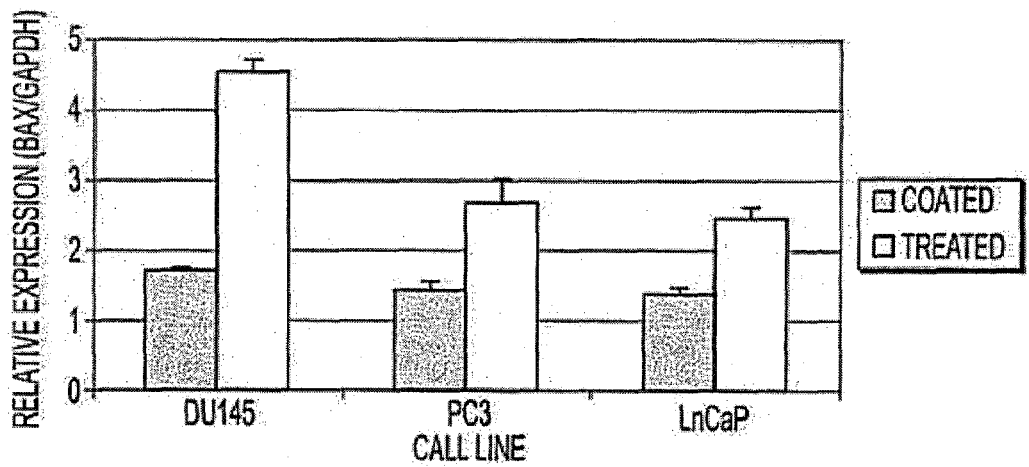
FIGS. 10A-C show analysis of apoptotic factors following PAX2 siRNA treatment.
Figure 10B:
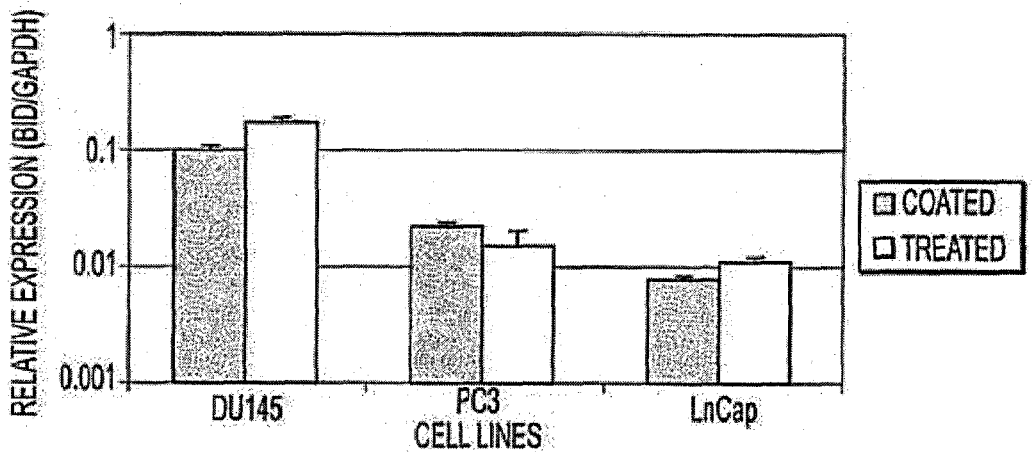
Figure 10C:
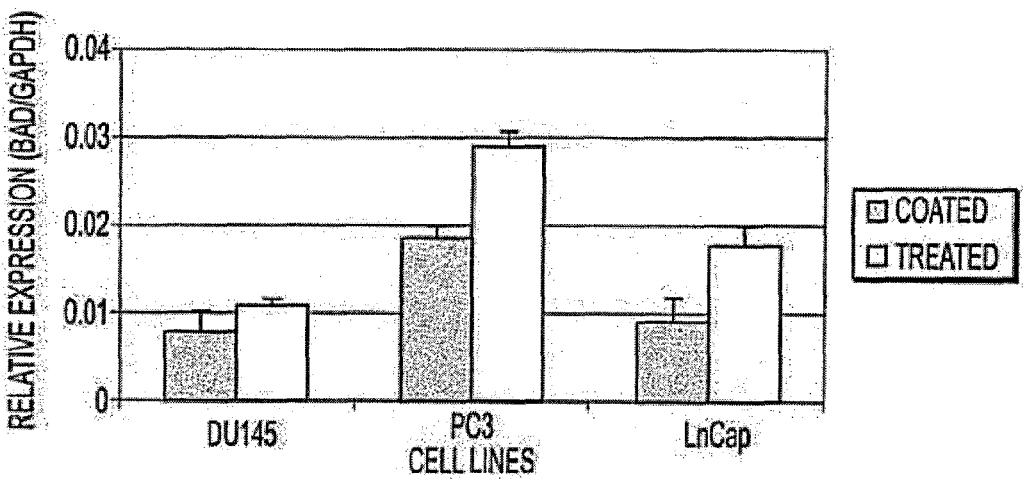

Effect of PAX2 Inhibition on Pro-apoptotic Factors: DU145, PC3 and LNCaP cells were treated with siRNA against PAX2 for six days and expression of pro-apoptotic genes dependent and independent of p53 transcription regulation were measured to monitor cell death pathways. For BAX, there was a 1.81-fold increase in LNCaP, a 2.73-fold increase in DU145, and a 1.87-fold increase in PC3 (FIG. 10, panel A). Expression levels of BID increased by 1.38-fold in LNCaP and 1.77-fold in DU145 (FIG. 10, panel B). However, BID expression levels decreased by 1.44-fold in PC3 following treatment (FIG. 10, panel C). Analysis of BAD revealed a 2.0-fold increase in expression in LNCaP, a 1.38-fold increase in DU145, and a 1.58-fold increase in PC3.

These results demonstrate dependency of prostate cancer cell survival on PAX2 expression. Following p53 activation as a result of PAX2 knock-down in the p53-expressing cell line LNCaP, the p53-mutated line DU145, and the p53-null line PC3, caspase activity was detected in all three lines, indicating of the initiation of programmed cell death. BAX expression was upregulated in all three cell lines independent of p53 status. The expression of pro-apoptotic factor BAD was also increased in all three lines following PAX2 inhibition. Following treatment with PAX2 siRNA, BID expression was increased in LNCaP and DU145, but actually decreased in PC3. These results indicate that cell death observed in prostate cancer is influenced by but is not dependent on p53 expression. The initiation of apoptosis in prostate cancer cells through different cell death pathways irrespective of p53 status indicates that PAX2 inhibits other tumor suppressors.

EXAMPLE 3

Figure 11:
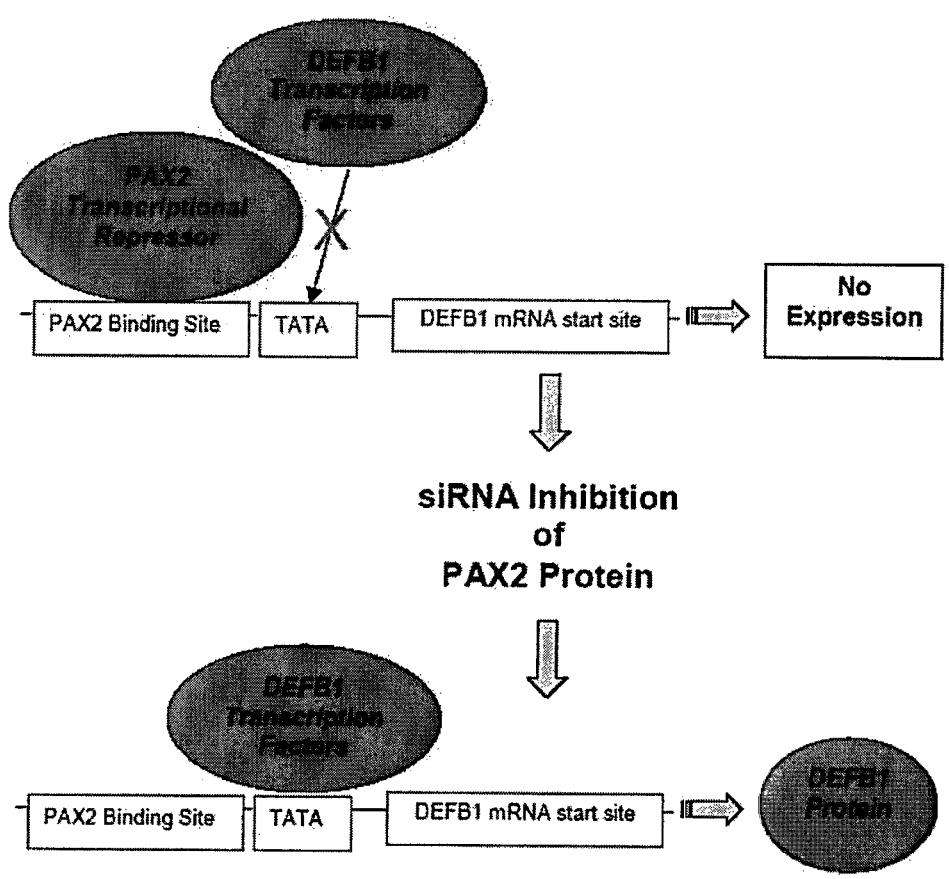
FIG. 11 shows model of PAX2 binding to DNA recognition sequence.

Inhibition of PAX2 Oncogene Results in DEFB1-Mediated Death of Prostate Cancer Cells The identification of tumor-specific molecules that serve as targets for the development of new cancer drugs is considered to be a major goal in cancer research. Example 1 demonstrated that there is a high frequency of DEFB1 expression loss in prostate cancer, and that induction of DEFB1 expression results in rapid apoptosis in androgen receptor negative-stage prostate cancer. These data show that DEFB1 plays a role in prostate tumor suppression. In addition, given that it is a naturally occurring component of the immune system of normal prostate epithelium, DEFB1 is expected to be a viable therapeutic agent with little to no side effects. Example 2 demonstrated that inhibition of PAX2 expression results in prostate cancer cell death independent of p53. These data indicate that there is an addition pro-apoptotic factor or tumor suppressor that is inhibited by PAX2. In addition, the data show that the oncogenic factor PAX2, which is over-expressed in prostate cancer, is a transcriptional repressor of DEFB1. The purpose of this study is to determine if loss of DEFB1 expression is due to aberrant expression of the PAX2 oncogene, and whether inhibiting PAX2 results in expression of DEFB1 and DEFB1-mediated cell death (FIG. 11).

3.1 Materials and Methods

RNA isolation and quantitative RT-PCR: RNA isolation and quantitative RT-PCR of DEFB1 were performed as described in Example 1.

Figure 12:
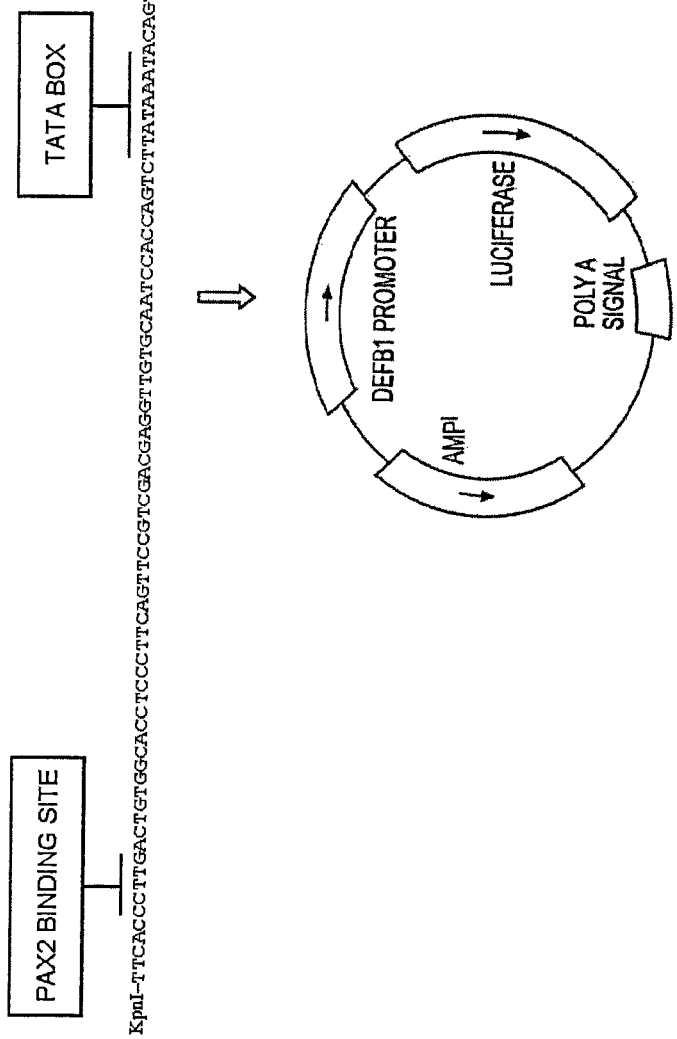
FIG. 12 illustrates the DEFB1 reporter construct.

Generation of the DEFB1 Reporter Construct: The pGL3 luciferase reporter plasmid was used to monitor DEFB1 reporter activity. A region 160 bases upstream of the DEFB1 transcription initiation site and included the DEFB1 TATA box. The region also included the CCTTG (SEQ ID NO: 1) sequence which is necessary for PAX2 binding. The PCR primers were designed to contain KpnI and NheI restriction sites. The DEFB1 promoter PCR product (SEQ ID NO: 117) was restriction digested with KpnI and NheI and ligated into a similarly restriction digested pGL3 plasmid (FIG. 12). The constructs were transfected into E. coli and individual clones were selected and expanded. Plasmids were isolated and sequence integrity of the DEFB1/pGL3 construct was verified by automated sequencing.

Luciferase reporter assay: 1 μg of the DEFB1 reporter construct or the control pGL3 plasmid was transfected into $1 \times 10^6$ DU145 cells. Next, $0.5 \times 10^3$ cells were seeded onto each well of a 96-well plate and allowed to grow overnight. Then, fresh medium was added containing PAX2 siRNA or media only and the cells were incubated for 48 hours. Luciferase was detected by the BrightGlo kit according to the manufacturer's protocol (Promega) and the plates were read on a Veritas automated 96-well luminometer. Promoter activity was expressed as relative luminescence.

Analysis of membrane permeability: Acridine orange (AO)/ethidium bromide (EtBr) dual staining was performed to identify changes in cell membrane integrity, as well as apoptotic cells by staining the condensed chromatin. AO stains viable cells as well as early apoptotic cells, whereas EtBr stains late stage apoptotic cells that have lost membrane permeability. Briefly, cells were seeded into 2 chamber culture slides (BD Falcon, USA). Cells transfected with empty pIND plasmid/pvgRXR or pIND DEFB1/pvgRXR were induced for 24 or 48 h with media containing 10 μM Ponasterone A. Control cells were provided fresh media at 24 and 48 h. In order to determine the effect of PAX2 inhibition on membrane integrity, separate culture slides containing DU145, PC3 and LNCaP were treated with PAX2 siRNA and incubated for 4 days. Following this, cells were washed once with PBS and stained with 2 ml of a mixture (1:1) of AO (Sigma, USA) and EtBr (Promega, USA) (5 ug/ml) solution for 5 min. Following staining, the cells were again washed with PBS. Fluorescence was viewed by a Zeiss LSM 5 Pascal Vario 2 Laser Scanning Confocal Microscope (Carl Zeiss Jena, Germany). The excitation color wheel contain BS505-530 (green) and LP560 (red) filter blocks which allowed for the separation of emitted green light from AO into the green channel and red light from EtBr into the red channel. The laser power output and gain control settings within each individual experiment were identical between control and DEFB1 induced cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems, San Jose, Calif.) for image processing and hard copy presentation.

ChIP analysis of PAX2: Chromatin immunoprecipitation (ChIP) allows the identification of binding sites for DNA-binding proteins based upon in vivo occupancy of a promoter by a transcription factor and enrichment of transcription factor bound chromatin by immunoprecipitation. The DU145 and PC3 cell lines over-expresses the PAX2 protein, but does not express DEFB1. Cells were incubated with PBS containing 1.0% formaldehyde for 10 minutes to crosslink proteins to DNA. Samples were then sonicated to yield DNA with an average length of 600 bp. Sonicated chromatin precleared with Protein A Dynabeads was incubated with PAX2-specific antibody or "no antibody" control [isotype-matched control antibodies]. Washed immunoprecipitates were then collected. After reversal of the crosslinks, DNA was analyzed by PCR using promoter-specific primers to determine whether DEFB1 is represented in the PAX2-immunoprecipitated samples. Primers were designed to amplify the 160 bp region immediately upstream of the DEFB1 mRNA start site which contained the DEFB1 TATA box and the functional CCTTG (SEQ ID NO: 1) PAX2 recognition site. For these studies, positive controls included PCR of an aliquot of the input chromatin (prior to immunoprecipitation, but crosslinks reversed). All steps were performed in the presence of protease inhibitors.

Figure 13:
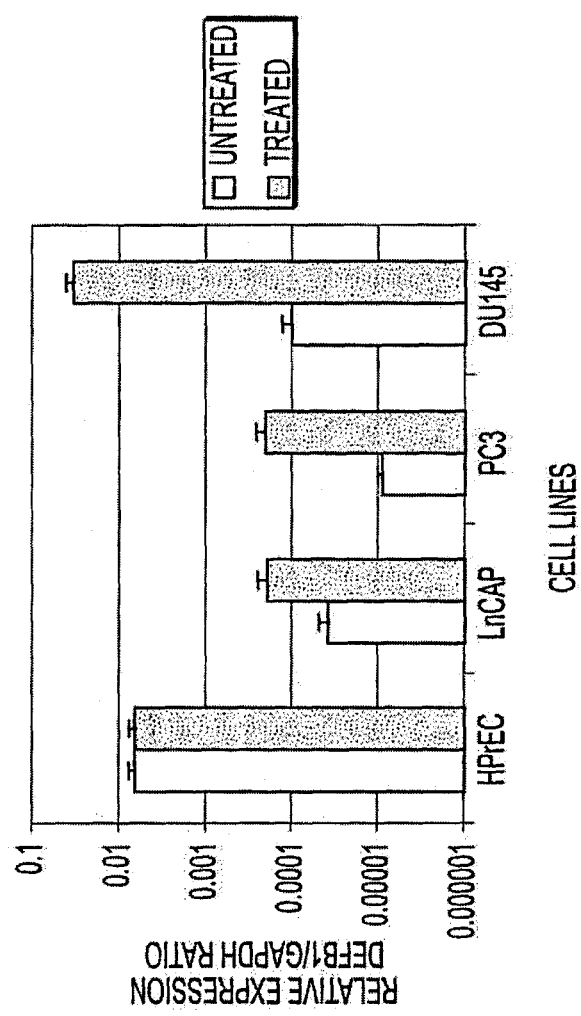
FIG. 13 shows inhibition of PAX2 results in DEFB1 Expression.
Figure 14:
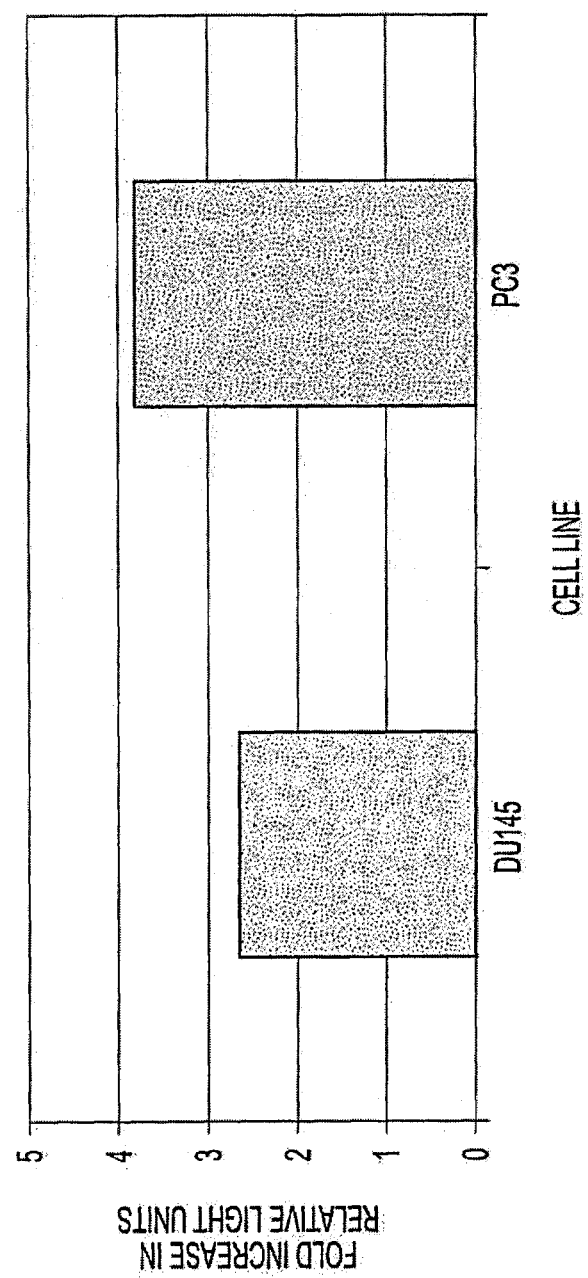
FIG. 14 shows that inhibition of PAX2 results in increased DEFB1 promoter activity.

3.2 Results siRNA inhibition of PAX2 increases DEFB1 expression: QRT-PCR analysis of DEFB1 expression before siRNA treatment revealed relative expression levels of 0.00097 in DU145, 0.00001 in PC3, and 0.00004 LNCaP (FIG. 13). Following siRNA knock-down of PAX2, relative expression was 0.03294 (338-fold increase) in DU145, 0.00020 (22.2-fold increase) in PC3 and 0.00019 (4.92-fold increase) in LNCaP. As a negative control, the human prostate epithelial cell line (hPrEC) which is PAX2 null, revealed expression levels at 0.00687 before treatment and 0.00661 following siRNA treatment confirming no statistical change in DEFB1 expression.

siRNA inhibition of PAX2 increases DEFB1 promoter activity: FIG. 14 shows that inhibition of PAX2 results in increased DEFB1 promoter activity. PC3 promoter/pGL3 and DU145 promoter/pGL3 construct were generated and were transfected into PC3 and DU145 cells, respectively. Promoter activity was compared before and after PAX2 inhibition by siRNA treatment. DEFB1 promoter activity increased 2.65-fold in DU145 and 3.78 fold in PC3 following treatment.

Figure 15:
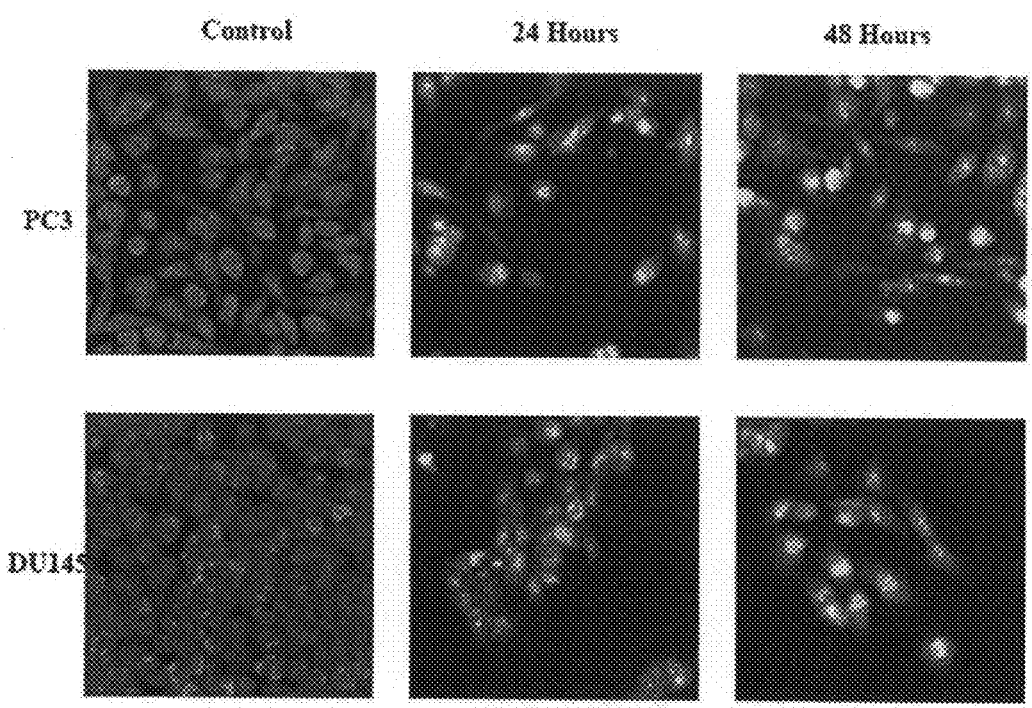
FIG. 15 shows that DEFB1 expression causes loss of membrane integrity.

DEFB1 causes cell membrane permeability: Membrane integrity was monitored by confocal analysis. As shown in FIG. 15, intact cells stain green due to AO which is membrane permeable. In addition, cells with compromised plasma membranes would stain red by EtBr which is membrane impermeable. Uninduced DU145 (A) and PC3 (D) cells stained positively with AO and emitted green color, but did not stain with EtBr. However, DEFB1 induction in both DU145 (B) and PC3 (E) resulted in the accumulation of EtBr in the cytoplasm at 24 hours indicated by the red staining. By 48 hours, DU145 (C) and PC3 (F) possessed condensed nuclei and appeared yellow, which was due to the presence of both green and red staining resulting from the accumulation of AO and EtBr, respectively.

Figure 16:
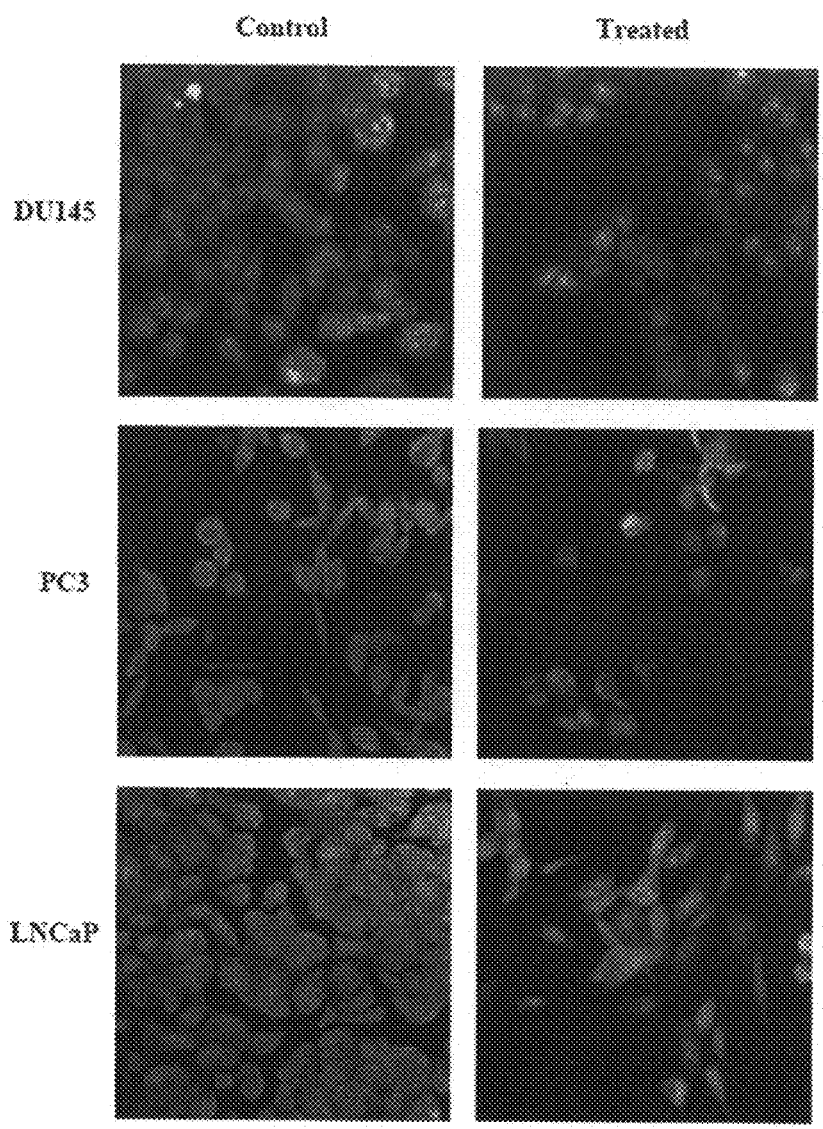
FIG. 16 shows that PAX2 inhibition results in loss of membrane integrity.

Inhibition of PAX2 results in membrane permeability: Cells were treated with PAX2 siRNA for 4 days and membrane integrity was monitored again by confocal analysis. As shown in FIG. 16, both DU145 and PC3 possessed condensed nuclei and appeared yellow. However, LNCaP cells' cytoplasm and nuclei remained green following siRNA treatment. Also red staining at the cell periphery indicates the maintenance of cell membrane integrity. These findings indicate that the inhibition of PAX2 results in specifically DEFB1-mediated cell death in DU1145 and PC3, but not LNCaP cells. Death observed in LNCaP is due to the trans activation of the existing wild-type p53 in LNCap following PAX2 inhibition.

Figure 17A:
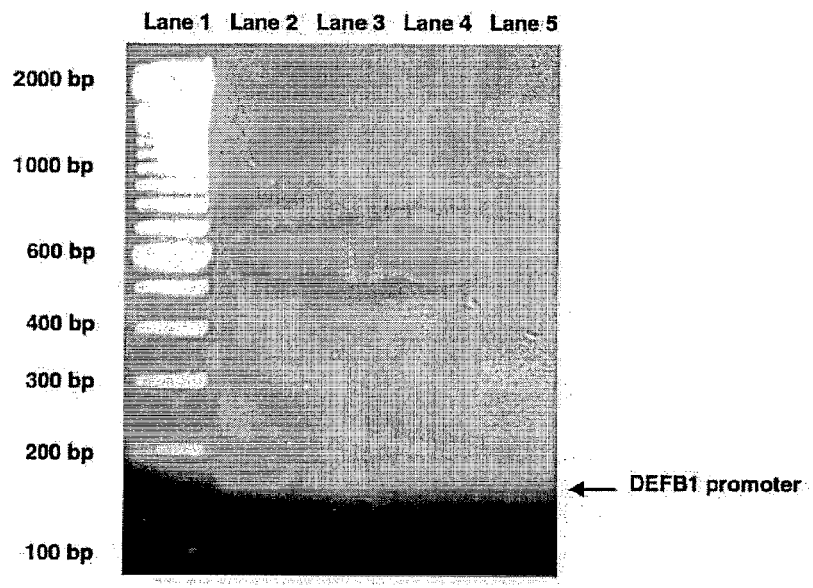
FIGS. 17A (top panel) and 17B (bottom panel) show ChIP analysis showing PAX2 binding to the DEFB1 promoter.

PAX2 binds to the DEFB1 promoter: ChIP analysis was performed on DU145 and PC3 cells to determine if the PAX2 transcriptional repressor is bound to the DEFB1 promoter (FIG. 17). In FIG. 17A, Lane 1 contains a 100 bp molecular weight marker. Lane 2 is a positive control representing 160 bp region of the DEFB1 promoter amplified from DU145 before cross-linking and immunoprecipitation. Lane 3 is a negative control representing PCR performed without DNA. Lanes 4 and 5 are negative controls representing PCR from immunoprecipitations performed with IgG from cross-linked DU145 and PC3, respectively. PCR amplification of 25 pg of DNA (lane 6 and 8) and 50 pg of DNA (lane 7 and 9) immunoprecipitated with anti-PAX2 antibody after crosslinking show a 160 bp promoter fragment in DU145 and PC3, respectively.

Figure 17B:
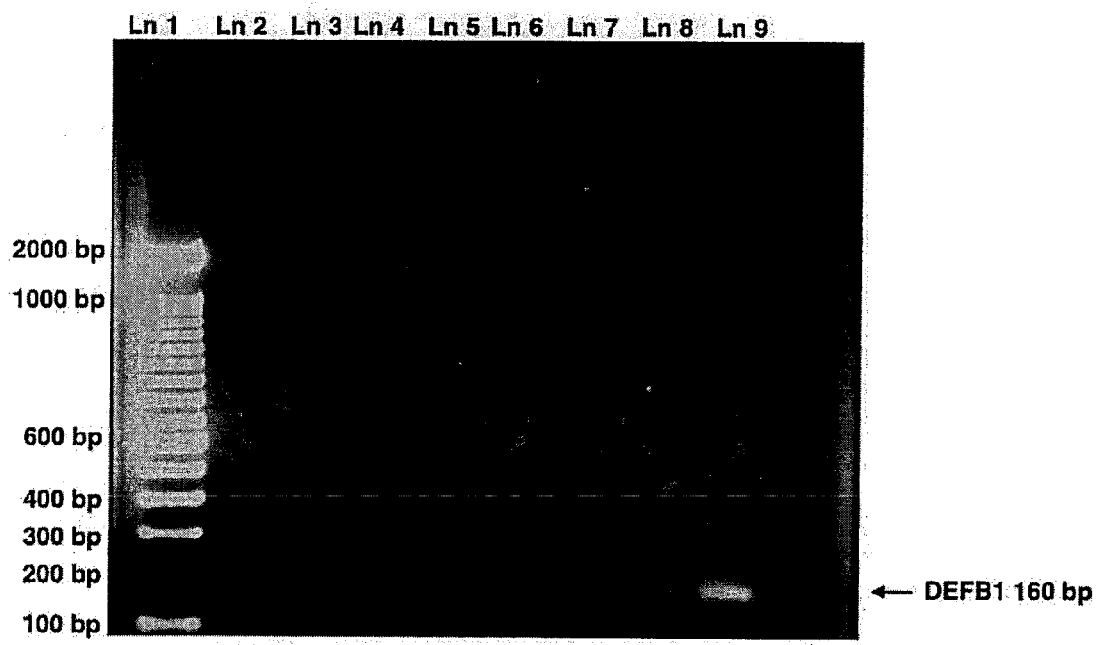

In FIG. 17B, lane 1 contains a 100 bp molecular weight marker. Lane 2 is a positive control representing 160 bp region of the DEFB1 promoter amplified from DU145 before cross-linking and immunoprecipitation. Lane 3 is a negative control representing PCR performed without DNA. Lane 4 and 5 are negative controls representing PCR from immunoprecipitations performed with IgG from cross-linked DU145 and PC3, respectively. PCR amplification of 25 pg of DNA (lane 6 and 8) and 50 pg of DNA (lane 7 and 9) immunoprecipitated with anti-PAX2 antibody after crosslinking show 160 bp promoter fragment in DU145 and PC3, respectively.

The results in this Example demonstrate that the oncogenic factor PAX2 suppresses DEFB1 expression. The suppression occurs at the transcriptional level. Furthermore, computational analysis of the DEFB1 promoter revealed the presence of a CCTTG (SEQ ID NO: 1) DNA binding site for the PAX2 transcriptional repressor near the DEFB1 TATA box (FIG. 1). One of the hallmarks of defensin cytotoxicity is the disruption of membrane integrity. These results show that ectopic expression of DEFB1 in prostate cancer cells results in a loss of membrane potential due to compromised cell membranes. The same phenomenon is observed after inhibiting PAX2 protein expression. Therefore, suppression of PAX2 expression or function, results in the re-establishment of DEFB1 expression and subsequently DEFB1-mediated cell death. Also, the present results establish the utility of DEFB1 as a directed therapy for prostate cancer treatment, and potentially other cancer treatments, through innate immunity.

EXAMPLE 4

Effect of DEFB1 Expression in Implanted Tumor Cells

The anti-tumoral ability of DEFB1 is evaluated by injecting tumor cells that overexpress DEFB1 into nude mice. DEFB1 is cloned into pBI-EGFP vector, which has a bidirectional tetracycline responsible promoter. Tet-Off Cell lines are generated by transfecting pTet-Off into DU145, PC3 and LNCaP cells and selecting with G418. The pBI-EGFP-DEFB1 plasmid is co-transfected with pTK-Hyg into the Tet-off cell lines and selected with hygromycin. Only single-cell suspensions with a viability of >90% are used. Each animal receives approximately 500,000 cells administered subcutaneously into the right flank of female nude mice. There are two groups, a control group injected with vector only clones and a group injected with the DEFB1 over-expressing clones. 35 mice are in each group as determined by a statistician. Animals are weighed twice weekly, tumor growth monitored by calipers and tumor volumes determined using the following formula: volume=$0.5\times(width)2\times length$. All animals are sacrificed by CO2 overdose when tumor size reaches 2 mm3 or 6 months following implantation; tumors are excised, weighed and stored in neutral buffered formalin for pathological examination. Differences in tumor growth between the groups are descriptively characterized through summary statistics and graphical displays. Statistical significance is evaluated with either the t-test or non-parametric equivalent.

EXAMPLE 5

Effect of PAX2 siRNA in Implanted Tumor Cells

Hairpin PAX2 siRNA template oligonucleotides utilized in the in vitro studies are utilized to examine the effect of the up-regulation of DEFB1 expression in vivo. The sense and antisense strand (see Table 3) are annealed and cloned into pSilencer 2.1 U6 hygro siRNA expression vector (Ambion) under the control of the human U6 RNA pol III promoter. The cloned plasmid is sequenced, verified and transfected into PC3, Du145, and LNCap cell lines. Scrambled shRNA is cloned and used as a negative control in this study. Hygromycin resistant colonies are selected, cells are introduced into the mice subcutaneously and tumor growth is monitored as described above.

EXAMPLE 6

Effect of Small Molecule Inhibitors of PAX2 Binding to DEFB1 Promoter

Short oligonucleotides complementary to the PAX2 DNA-binding domain are provided. Examples of such oligonucleotides include the 20-mer and 40-mer oligonucleotides containing the CCTTG (SEQ ID NO: 1) recognition sequence provided below. These lengths were randomly selected, and other lengths are expected to be effective in blocking the binding. As a negative control, oligonucleotides with a scrambled sequence (CTCTG) (SEQ ID NO: 22) were designed to verify specificity. The oligonucleotides are transfected into the prostate cancer cells and the HPrEC cells with lipofectamine reagent or Codebreaker transfection reagent (Promega, Inc). In order to confirm DNA-protein interactions, double stranded oligonucleotides will be labeled with [32P] dCTP and electrophoretic mobility shift assays are performed. DEFB1 expression can be monitored by QRT-PCR and Western blot analysis following treatment with oligonucleotides. Finally, cell death may be detected by the MTT assay and flow cytometry as previously described.

```
Recognition Sequence #1:
                                         (SEQ ID NO: 18)
CTCCCTTCAGTTCCGTCGAC Recognition Sequence #2:
                                         (SEQ ID NO: 19)
CTCCCTTCACCTTGGTCGAC Scramble Sequence #1:
                                         (SEQ ID NO: 23)
CTCCCTTCACTCTGGTCGAC Recognition Sequence #3:
                                         (SEQ ID NO: 20)
ACTGTGGCACCTCCCTTCAGTTCCGTCGACGAGGTTGTGC Recognition Sequence #4:
                                         (SEQ ID NO: 21)
ACTGTGGCACCTCCCTTCACCTTGGTCGACGAGGTTGTGC Scramble Sequence #2:
                                         (SEQ ID NO: 24)
ACTGTGGCACCTCCCTTCACTCTGGTCGACGAGGTTGTGC
```

Further examples of oligonucleotides of the invention include:

```
Recognition Sequence #1:
                                         (SEQ ID NO: 25)
5'-AGAAGTTCACCCTTGACTGT-3'

Recognition Sequence #2:
                                         (SEQ ID NO: 26)
5'-AGAAGTTCACGTTCCACTGT-3'

Scramble Sequence #1:
                                         (SEQ ID NO: 27)
5'-AGAAGTTCACGCTCTACTGT-3'

Recognition Sequence #3:
                                         (SEQ ID NO: 28)
5'-TTAGCGATTAGAAGTTCACCCTTGACTGTGGCACCTCCC-3'

Recognition Sequence #4:
                                         (SEQ ID NO: 29)
5'-GTTAGCGATTAGAAGTTCACGTTCCACTGTGGCACCTCCC-3'

Scramble Sequence #2:
                                         (SEQ ID NO: 30)
5'-GTTAGCGATTAGAAGTTCACGCTCTACTGTGGCACCTCCC-3'
```

This set of alternative inhibitory oligonucleotides includes recognition sequences for PAX2 binding, which are derived from the DEFB1 promoter (SEQ ID NOs: 25 and 28). The PAX2 gene is required for the growth and survival of various cancer cells including prostate. In addition, the inhibition of PAX2 expression results in cell death mediated by the innate immunity component DEFB1. Suppression of DEFB1 expression and activity may be accomplished by binding of the PAX2 protein to an excess quantity of double stranded oligonucleotide decoy comprising the CCTTG (SEQ ID NO: 1) recognition site in the DEFB1 promoter. Use of such oligonucleotide decoys provides a viable therapeutic target for treatment of prostate cancer. In this method, binding of the oligonucleotide decoy to PAX2, prevents or reduces PAX2 binding to the DEFB1 promoter, thereby allowing DEFB1 expression to proceed. The oligonucleotide sequences and experiment described above are examples demonstrating a model for the design of additional PAX2 inhibitor drugs.

EXAMPLE 7

Loss of DEFB1 Expression Results in Increased Tumorigenesis

Generation of loss of function mice: The Cre/loxP system has been useful in elucidating the molecular mechanisms underlying prostate carcinogenesis. A DEFB1 Cre conditional KO is used for inducible disruption within the prostate. The DEFB1 Cre conditional KO involves the generation of a targeting vector containing loxP sites flanking DEFB1 coding exons, targeted ES cells with this vector and the generation of germline chimeric mice from these targeted ES cells. Heterozygotes are mated to prostate-specific Cre transgenics and heterozygous intercross is used to generate prostate-specific DEFB1 KO mice. Four genotoxic chemical compounds have been found to induce prostate carcinomas in rodents: N-methyl-N-nitrosourea (MNU), N-nitrosobis 2-oxopropyl amine (BOP), 3,2X-dimethyl-4-amino-biphenyl (MAB) and 2-amino-1-methyl-6-phenylimidazow 4,5-bxpyridine (PhIP). DEFB1-transgenic mice are treated with these carcinogenic compounds via intra-gastric administration or i.v. injection for prostate adenoma and adenocarcinoma induction studies. Prostate samples are studied for differences in tumor growth and changes gene expression though histological, immunohistological, mRNA and protein analyses.

Generation of GOF mice: For PAX2 inducible GOF mice, PAX2 GOF (bi-transgenic) and wild-type (mono-transgenic) littermates are administered doxycycline (Dox) from 5 weeks of age to induce prostate-specific PAX2 expression. Briefly, PROBASIN-rtTA mono-transgenic mice (prostate cell-specific expression of tet-dependent rtTA inducer) are crossed to our PAX2 transgenic responder lines. For induction, bi-transgenic mice are fed Dox via the drinking water (500 mg/L freshly prepared twice a week). Initial experiments verify low background levels, good inducibility and cell-type specific expression of PAX2 and the EGFP reporter using transgenic founder line in bi-transgenic mice. Regarding experimental group sizes, 5-7 age- and sex-matched individuals in each group (wild-type and GOF) allow for statistical significance. For all animals in this study, prostate tissues are collected initially at weekly intervals for analysis and comparison, to determine carcinogenic time parameters.

PCR genotyping, RT-PCR and qPCR: PROBASIN-rtTA transgenic mice are genotyped using the following PCR primers and conditions:

```
PROBASIN5 (forward)
                                         (SEQ ID NO: 31)
5'-ACTGCCCATTGCCCAAACAC-3';

RTTA3 (reverse)
                                         (SEQ ID NO: 32)
5'-AAAATCTTGCCAGCTTTCCCC-3';
```

95° C. denaturation for 5 min, followed by 30 cycles of 95° C. for 30 sec, 57° C. for 30 sec, 72° C. for 30 sec, followed by a 5 min extension at 72° C., yielding a 600 bp product. PAX2 inducible transgenic mice are genotyped using the following PCR primers and conditions:

```
PAX2For
                                         (SEQ ID NO: 33)
5'-GTCGGTTACGGAGCGGACCGGAG-3';

Rev5'IRES
                                         (SEQ ID NO: 34)
5'-TAACATATAGACAAACGCACACCG-3';
```

95° C. denaturation for 5 min, followed by 34 cycles of 95° C. for 30 sec, 63° C. for 30 sec, 72° C. for 30 sec, followed by a 5 min extension at 72° C., yielding a 460 bp product.

Immortomouse hemizygotes are to be genotyped using the following PCR primers and conditions:

```
Immo11,
                                        (SEQ ID NO: 35)
5'-GCGCTTGTGTCGCCATTGTATTC-3';

Immo12,
                                        (SEQ ID NO: 36)
5'-GTCACACCACAGAAGTAAGGTTCC-3';
```

94° C. 30 sec, 58° C. 1 min, 72° C. 1 min 30 sec, 30 cycles to yield a ~1 kb transgene band. For genotyping PAX2 knockout mice, the following PCR primers and conditions are used:

```
PAX2 For
                                        (SEQ ID NO: 37)
5'-GTCGGTTACGGAGCGGACCGGAG-3';

PAX2Rev
                                        (SEQ ID NO: 38)
5'-CACAGAGCATTGGCGATCTCGATGC-3';
```

94° C. 1 min, 65° C. 1 min, 72° C. 30 sec, 36 cycles to yield a 280 bp band.

DEFB1 peptide animal studies: Six-week-old male athymic (nude) mice purchased from Charles River Laboratories are injected sub-cutaneously over the scapula with $10^6$ viable PC3 cells. One week after injection, the animals are randomly allocated to one of three groups—group I: control; group II: intraperitoneal injections of DEFB1, 100 μg/day, 5 days a week, for weeks 2-14; group III: intraperitoneal injections of DEFB1, 100 mg/day, 5 days a week, for weeks 8-14. Animals are maintained in sterile housing, four animals to a cage, and observed on a daily basis. At 10-day intervals, the tumors are measured by using calipers, and the volumes of the tumors are calculated by using $V=(L\times W2)/2$.

EXAMPLE 8

Targeting PAX2 Expression for the Chemoprevention of Intraepithelial Neoplasia and Cancer Cancer chemoprevention is defined as the prevention of cancer or treatment at the pre-cancer state or even earlier. The long period of progression to invasive cancer is a major scientific opportunity but also an economic obstacle to showing the clinical benefit of candidate chemopreventive drugs. Therefore, an important component of chemopreventive agent development research in recent years has been to identify earlier (than cancer) end points or biomarkers that accurately predict an agent's clinical benefit or cancer incidence-reducing effect. In many cancers, IEN is an early end point such as in prostate cancer. Given that the PAX2/DEFB1 pathway is deregulated during IEN and perhaps at even an earlier histopathological state makes it a powerful predictive biomarker and an excellent target for chemoprevention of cancer.

Figure 18:
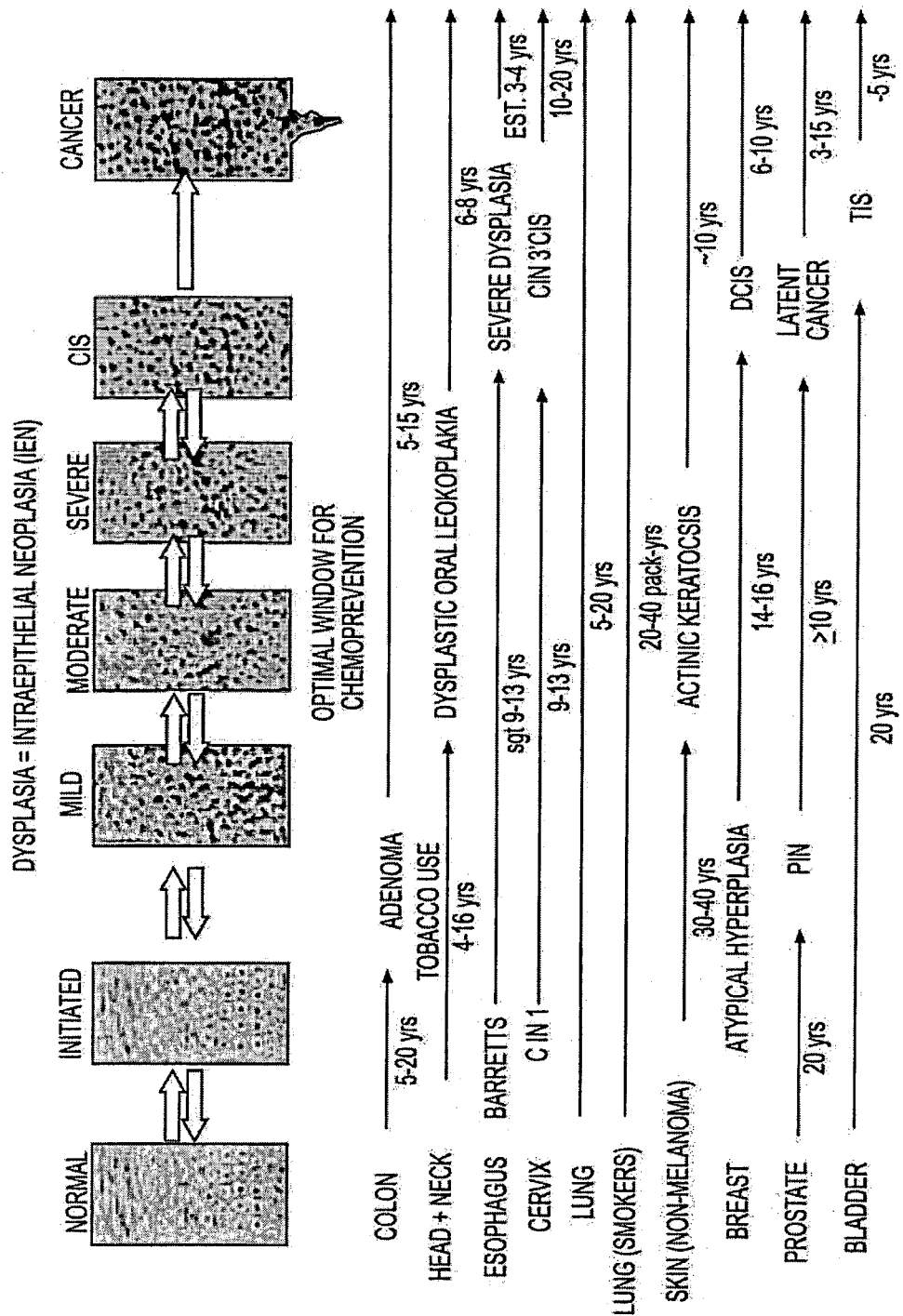
FIG. 18 shows targeting PAX2 as a chemopreventive strategy.

As shown in Table 1, the PAX2 gene is expressed in a number of cancers. In addition, several cancers have been shown to have aberrant PAX2 expression (FIG. 18). Shown in Table 4 are a number of compounds that suppress PAX2 and increases DEFB1 expression that may have utility as chemoprevention agents for prostate cancer. Angiotensin II (AngII) is a major regulator of blood pressure and cardiovascular homeostasis and is recognized as a potent mitogen. AngII mediates its biological effects through binding to two sub-types of receptors, Angiotensin Type I receptor (AT1R) and Angiotensin Type II receptor (AT2R) which belong to the super-family of G-protein-coupled receptors but have different tissue distribution and intracellular signaling pathways. In addition to its effects on blood pressure, AngII has been shown to play a role in various pathological situations involving tissue remodeling, such as wound healing, cardiac hypertrophy and development. In fact, recent studies have revealed local expression of several components of the renin-angiotensin system (RAS) in various cancer cells and tissues including the prostate. Upregulation of AT1R provides a considerable advantage to cancer cells that have "learned" to evade apoptosis and growth regulatory elements. To date a number of cancers have been shown to aberrantly express PAX2. Chemoprevention via target PAX2 expression may have a significant impact on cancer related deaths.

8.1 Materials and Methods

Cell culture: hPrEC cells and DU145, LnCap, and PC3 cell lines were cultured as described in Example 1.

Reagents and treatments: Cells were treated with 5 or 10 μM of AngII, 5 μM of the AT1R antagonist Los, 5 μM of the AT2R antagonist PD123319, 25 μM of the MEK inhibitor U0126, 20 μM of the MEK/ERK inhibitor PD98059 or 250 μM of the AMP kinase inducer AICAR.

Western blot analysis: Western blot analysis was performed as described in Example 2. Blots were then probed with primary antibody (anti-PAX2, -phospho-PAX2, -JNK, -phospho-JNK, -ERK1/2, or -phospho-ERK1/2) (Zymed, San Francisco, Calif.) at 1:1000-2000 dilutions. After washing, the membranes were incubated with anti-rabbit antibody conjugated to horseradish peroxidase (HRP) (dilution 1:5000; Sigma), and signal detection was visualized using chemilluminescence reagents (Pierce) on an Alpha Innotech Fluorchem 8900. As a control, blots were stripped and re-probed with mouse anti-β-actin primary antibody (1:5000; Sigma-Aldrich) and HRP-conjugated anti-mouse secondary antibody (1:5000; Sigma-Aldrich), and signal detection was again visualized.

QRT-PCR analysis: Quantitative real-time RT-PCR was performed as described in Example 1 to verify changes in gene expression following PAX2 knockdown in PC3 and DU145 prostate cancer cell lines and the hPrEC normal prostate epithelial cells. Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Relative expression was calculated as the ratio between each genes and GAPDH. All reactions were carried out in triplicate.

Thymidine incorporation: Proliferation of cells was determined by [3H] thymidine ribotide ([3H] TdR) incorporation into DNA. $0.5\times10^6$ cells/well of suspension DU145 cells were plated in their appropriate media. Cells were incubated for 72 h with or without the presence of AngII at the indicated concentrations. Cells were exposed to 37 kBq/ml [methyl-3H] thymidine in the same medium for 6 h. The adherent cells were fixed by 5% trichloroacetic acid and lysed in SDS/NaOH lysis buffer overnight. Radioactivity was measured by Beckman LS3801 liquid scintillation counter (Canada). Suspension cell cultures were harvested by cell harvester (Packard instrument Co., Meriden, Conn.), and radioactivity was measured by 1450 microbeta liquid scintillation counter (PerkinElmer Life Sciences).

8.2 Results

Figure 19:
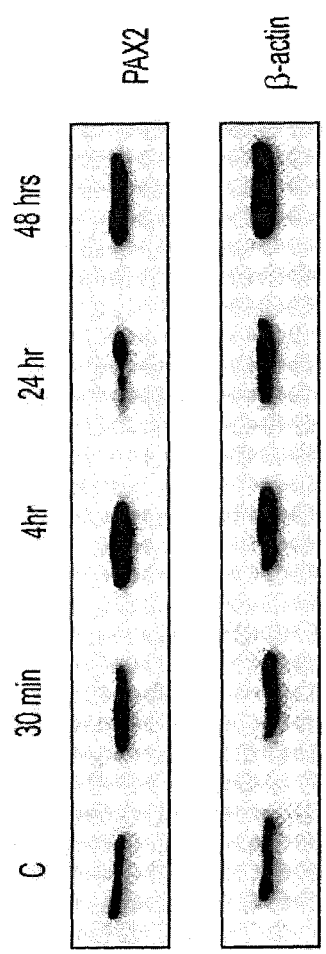
FIG. 19 shows effect of angiotensin II (Ang II) on PAX2 expression in DU145 Cells.

To investigate the effect of AngII on PAX2 expression in DU145 prostate cancer cells, PAX2 expression was examined following treatment with AngII over a 30 min to 48 hour period. As shown in FIG. 19, PAX2 expression progressively increased over time following AngII treatment.

Figure 20A:
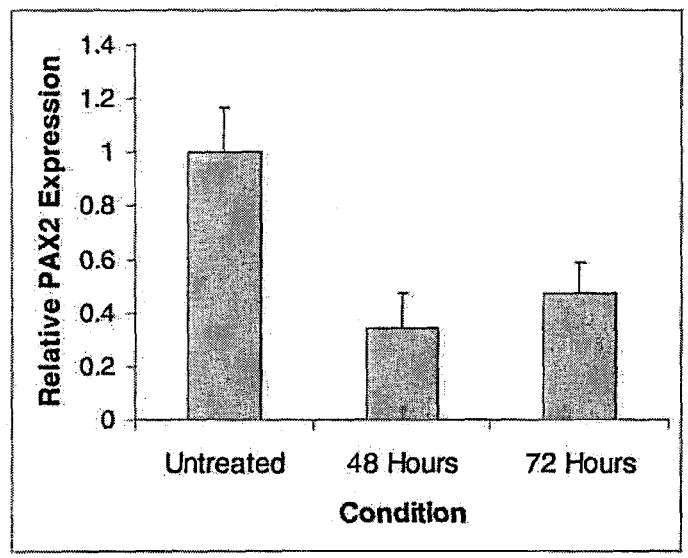
FIG. 20A shows that PAX2 expression is regulated by the AT1R receptor pathway via Ras signalling as evidenced by treatment of DU145 cells with the AT1R blocker, Losartan (Los).

Blocking RAS signaling by treating DU145 with Los significantly reduced PAX2 expression. As shown in FIG. 20A, following treatment of DU145 cells with Los, PAX2 expression was reduced by 37% after 48 hours and by 50% after 72 hours compared to untreated control DU145 cells.

Figure 20B:
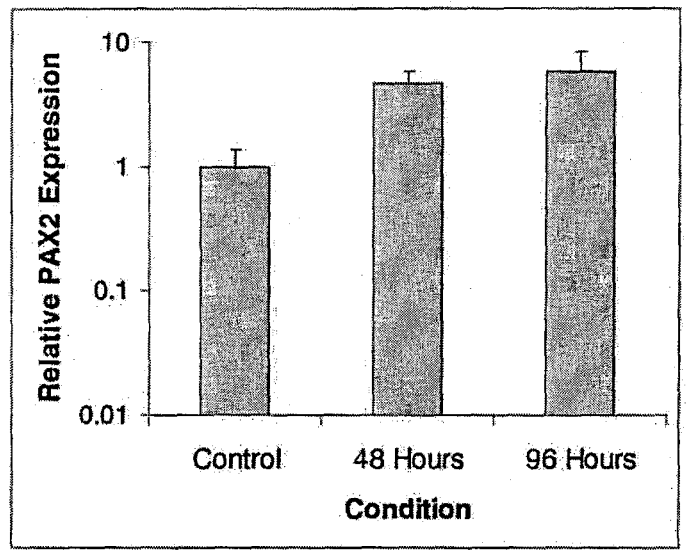
FIG. 20B shows that PAX2 expression is regulated by the AT1R receptor pathway as evidenced by treatment of DU45 cells with the AT2R blocker PD123319.

It is known that the AT2R receptor opposes the action of the AT1R. Therefore, the effect of blocking the AT2R receptor on PAX2 expression was examined. Treatment of DU145 with the AT2R blocker PD123319 resulted in a 7-fold increase in PAX2 expression after 48 hours and an 8-fold increase after 96 hours of treatment (FIG. 20B). Collectively, these findings demonstrate that PAX2 expression is regulated by the AT1R receptor pathway.

Figure 21:
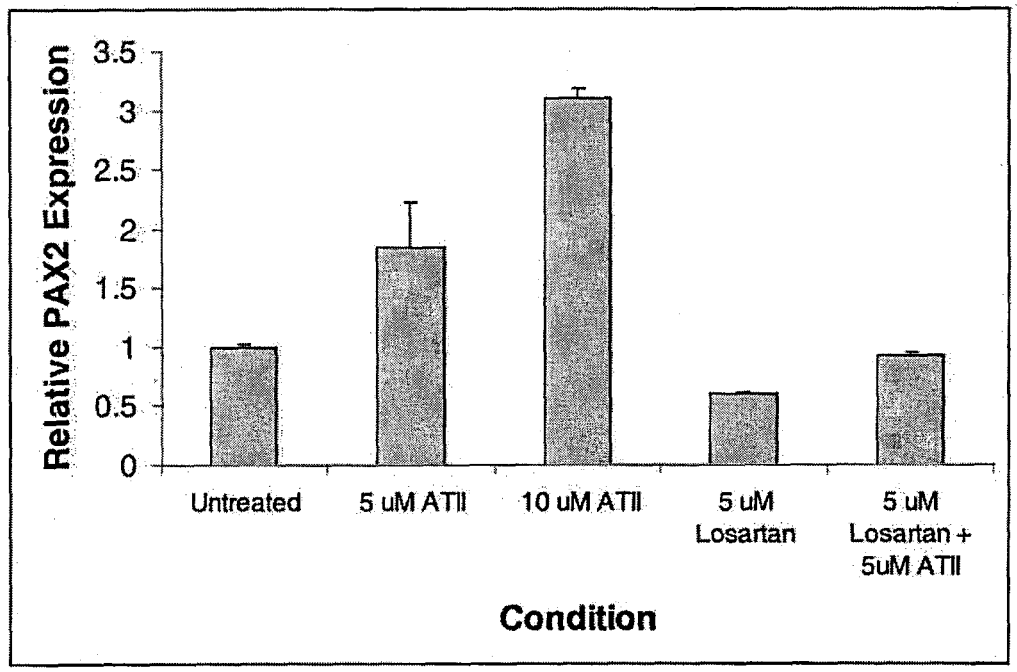
FIG. 21 shows that Los blocks the effect of Angiotensin II (AngII) effect on PAX2 expression in DU145.

It is known that AngII directly affects the proliferation of prostate cancer cells through AT1R-mediated activation of MAPK and STAT3 phosphorylation. Treatment of DU145 with AngII resulted in a two- to three-fold increase in proliferation rate (FIG. 21). However, treatment with Los decreased proliferated rates by 50%. In addition, blocking the AT1R receptor by pre-treating with Los for 30 min suppressed the effect of AngII on proliferation.

Figure 22:
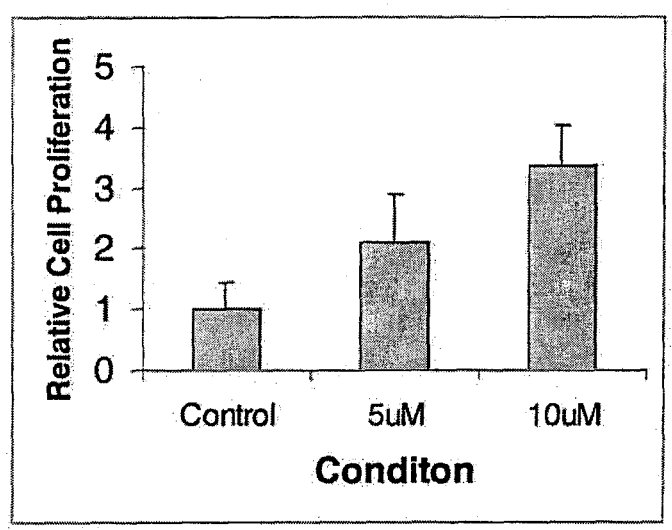
FIG. 22 shows AngII increases DU145 cell proliferation.
Figure 23A:
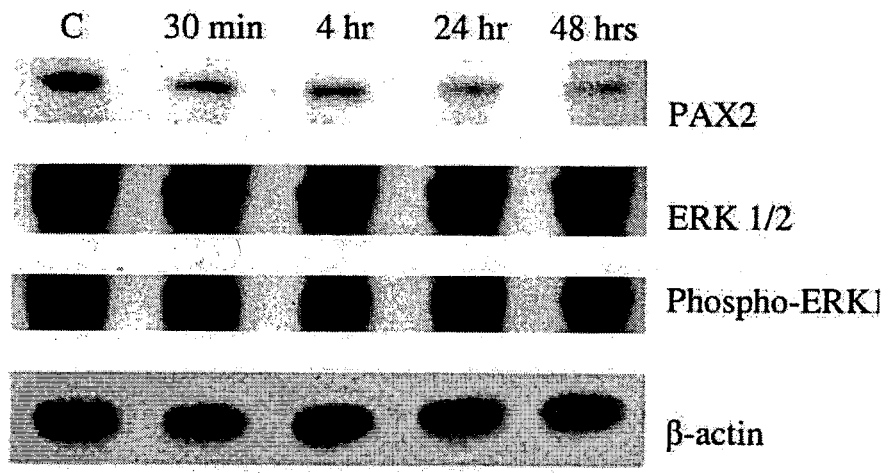
FIG. 23A shows that treatment of DU145 cells with Losartan suppresses phospho-ERK 1/2 and PAX2 protein levels.
Figure 23B:
FIG. 23B shows that the AT1R blocker, Losartan (Los), the MEK kinase antagonists, PD98059 and U0126, and the AMP kinase activator, 5-Aminoimidazole-4-carboxamide-1-β-4-ribofuranoside (AICAR) suppress PAX2 protein levels in DU145 cells compared to the untreated control.
Figure 23C:
FIG. 23C shows that Los, U0126, PD98059, and AICAR suppress phospho-STAT3 protein levels in DU145 cells compared to the untreated control.

To further examine the role of the AT1R signaling in the regulation of PAX2 expression and activation, the effect of blocking various components of the MAP kinase signaling pathway on PAX2 expression was examined. DU145 cells treated with the MEK inhibitor U0126 resulted in a significant reduction of PAX2 expression (FIG. 22). Furthermore, treatment with MEK/ERK inhibitor PD98059 also resulted in decreased PAX2. Treatment of DU145 cells with Los had no effect on ERK protein levels, but reduced the amount of phospho-ERK (FIG. 23A). However, treatment of DU145 with Los resulted in a significant reduction of PAX2 expression. Similar results were observed following treatment with U0126 and PD98059 (FIG. 23B). It is also known that PAX2 expression is regulated by STAT3 which is a down-stream target of ERK. Treatment of DU145 with Los, U0126, and PD98059 reduced phospho-STAT3 protein levels (FIG. 23C). These results demonstrate that PAX2 is regulated via AT1R in prostate cancer cells.

Figure 24A:
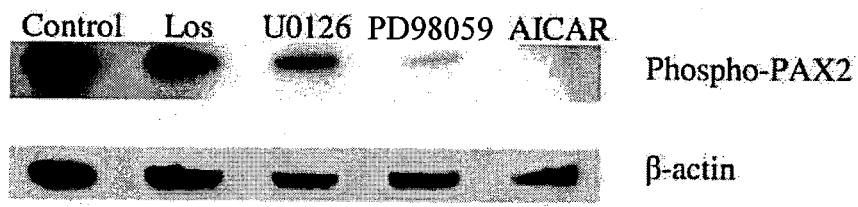
FIG. 24A shows that Los, U0126, PD98059, and AICAR suppress phospho-PAX2 protein expression levels.
Figure 24B:
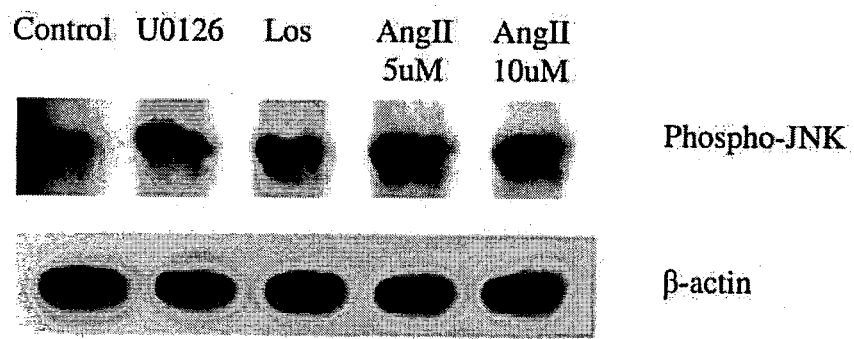
FIG. 24B shows that the decrease in phospho-PAX2 levels in FIG. 24A was due to decreased PAX2 levels, not decreased phosphorylation of PAX2, since Los and U0126 failed to decrease phospho-JNK protein levels.

In addition, the effect of AT1R signaling on PAX2 activation by JNK was examined. Treatment of DU145 with Los, U0126, and PD98059 all resulted in a significant decrease or suppression of phospho-PAX2 protein levels (FIG. 24A). However, Los and U0126 did not decrease phospho-JNK protein levels (FIG. 24B). Therefore, the decrease in phospho-PAX2 appears to be due to decreased PAX2 levels, but not decreased phosphorylation.

5-Aminoimidazole-4-carboxamide-1-β-4-ribofuranoside (AICAR) is widely used as an AMP-kinase activator, which regulates energy homeostasis and response to metabolic stress. Recent reports have indicated anti-proliferative and pro-apoptotic action of activated AMPK using pharmacological agents or AMPK overexpression. AMPK activation has been shown to induce apoptosis in human gastric cancer cells, lung cancer cells, prostate cancer, pancreatic cells, and hepatic carcinoma cells and enhance oxidative stress induced apoptosis in mouse neuroblastoma cells, by various mechanisms that include inhibition of fatty acid synthase pathway and induction of stress kinases and caspase 3. In addition, treatment of PC3 prostate cancer cells increased expression of p21, p27, and p53 proteins and inhibition of PI3K-Akt pathway. All of these pathways are directly or indirectly regulated by PAX2. Treatment of prostate cancer cells with AICAR resulted in the suppression of PAX2 expression (FIG. 23B) as well as its activated form phosphor-PAX2 (FIG. 24A). In addition, phospho-STAT3 which regulated PAX2 expression was also suppressed (FIG. 23C).

Figure 25:
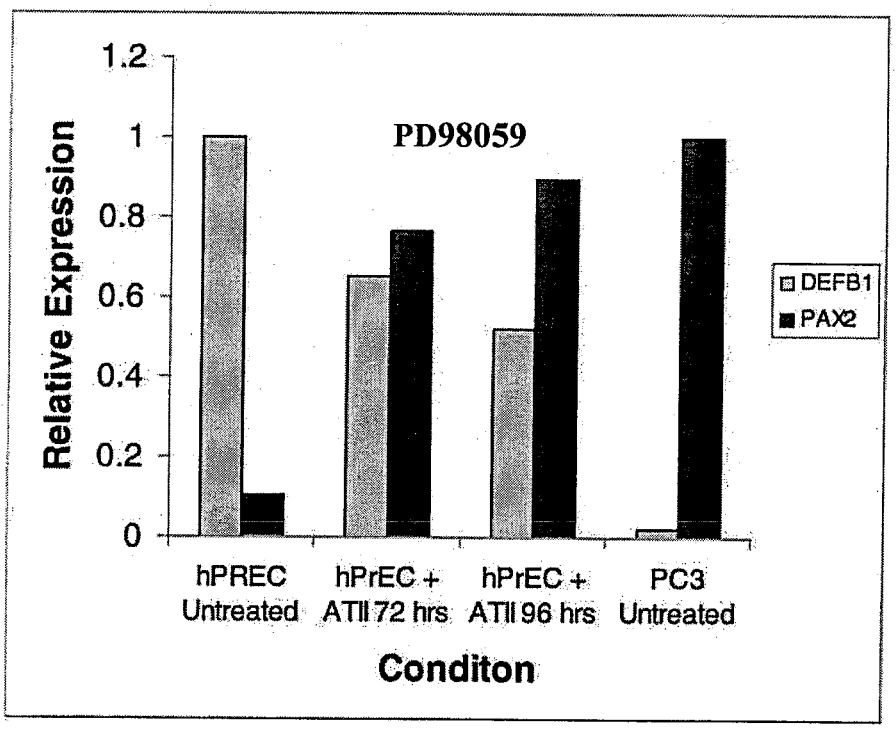
FIG. 25 shows that untreated hPrEC exhibited relatively low PAX2 expression levels and high DEFB1 expression levels, whereas PC3 prostate cancer cells show the reverse. Treatment of hPrEC cells with AngII increases PAX2 expression levels and decreases DEFB1 expression levels as is the case in prostate cancer cells.

Finally, it was hypothesized that aberrant RAS signaling which leads to upregulation and overexpression of PAX2 suppresses the expression of the DEFB1 tumor suppressor gene. To investigate this possibility, a normal prostate epithelial primary culture hPrEC was treated with AngII and examined for expression levels of PAX2 and DEFB1. An inverse relationship between DEFB1 and PAX2 expression was discovered in normal prostate cells versus prostate cancer cells. As shown in FIG. 25, untreated hPrEC exhibited 10% relative PAX2 expression compared to PAX2 expression in PC3 prostate cancer cells. Conversely, untreated PC3 cells exhibited only 2% DEFB1 expression compared to DEFB1 expression in untreated hPrEC cells. Following 72 hours of treatment with 10 μM of AngII in, hPrEC cells, there was a 35% decrease in DEFB1 expression and a 66% increase in PAX2 expression relative to untreated hPrEC cells; by 96 hours there was a 50% decrease in DEFB1 expression and a 79% increase in DEFB1 relative to untreated hPrEC cells. Furthermore, the increase in PAX2 expression in hPrEC after 72 hours was 77% of the PAX2 levels observed in PC3 prostate cancer cells. After 96 hours of AngII treatment, PAX2 expression was 89% of PAX2 expression in PC3 cells. These results demonstrate that deregulated RAS signaling suppresses DEFB1 expression and activates PAX2 expression in prostate cells.

Figure 26:
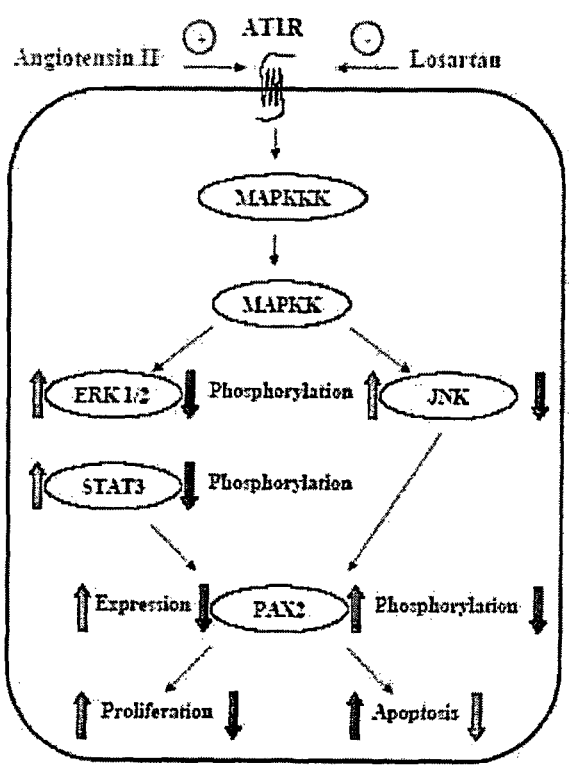
FIG. 26 shows a schematic of AT1R signaling on expression and phosphorylation of PAX2 and on proliferation and apoptosis in prostate cells.

Inhibition of apoptosis is a critical pathophysiological factor that contributes to the development of cancer. Despite significant advances in cancer therapeutics, little progress has been made in the treatment of advanced disease. Given that carcinogenesis is a multiyear, multistep, multipath disease of progression, chemoprevention through the use of drug or other agents to inhibit, delay, or reverse this process has been recognized as a very promising area of cancer research. Successful drug treatment for the chemoprevention of prostate cancer requires the use of therapeutics with specific effects on target cells while maintaining minimal clinical effects on the host with the overall goal of suppressing cancer development. Therefore, understanding the mechanisms in early stage carcinogenesis is critical in determining the efficacy of a specific treatment. The significance of aberrant PAX2 expression and its abrogation of apoptosis, with subsequent contribution to tumor formation, suggest that it may be a suitable target for prostate cancer treatment. PAX2 was regulated by the AT1R in prostate cancer (FIG. 26). In this, deregulated RAS signaling resulted in increased PAX2 oncogene expression, and a decrease in the expression of DEFB1 tumor suppressor. Therefore, the use of AT1R antagonists decreases PAX2 expression and results in increased prostate cancer cell death via re-expression of DEFB1 (FIG. 27). These results offer a novel finding that targeting PAX2 expression via the renin-angiotensin signaling pathway, the AMP kinase pathway, or other methods involving the inactivation of the PAX2 protein (i.e. anti-PAX2 antibody vaccination) represents viable targets for cancer prevention (Table 4).

TABLE 4

Compounds Utilized to Inhibit PAX2
Expression for Chemoprevention

| | NAME | Drug Class |
|---|---|---|
| Drug 1 | Losartan | Angiotensin Type 1 Receptor blocker |
| Drug 2 | PD123319 | Angiotensin Type 2 Receptor blocker |
| Drug 3 | U0126 | MEK inhibitor |
| Drug 4 | PD98059 | MEK/ERK inhibitor |
| Drug 5 | AICAR | AMP kinase inducer |
| | Target | Drug Function |
| Drug A | Anti-PAX2 Antibody | PAX2 Vaccine |
| Drug B | Angiotensinogen | Renin-AngII pathway inhibitor |
| Drug C | Angiotensin Converting Enzyme | Renin-AngII pathway inhibitor |

This study demonstrates that the upregulation of the PAX2 oncogene in prostate cancer is due to deregulated RAS signaling. PAX2 expression is regulated by the ERK 1/2 signaling pathway which is mediated by the Angiotensin type I receptor. In addition, blocking the AT1R with Losartan (Los) suppresses PAX2 expression. In addition, AICAR which is an AMPK activator has also shown promise as a potential PAX2 inhibitor. Collectively, these studies strongly implicate these classes of drugs as potential suppressors of PAX2 expression and may ultimately serve as novel chemoprevention agents.

EXAMPLE 9

PAX2-DEFB1 Expression Level as a Grading Tool for Prostate Tissue and Predictor of Prostate Cancer Development 9.1 Materials and Methods QRT-PCR analysis: Prostate sections were collected from patients that underwent radical prostatectomies. Following pathological examination, laser capture microdisection was performed to isolate areas of Normal, Proliferative Intraepithelial Neoplasia (PIN) and Cancerous tissue. QRT-PCR was performed as previously described to assess expression. DEFB1 and PAX2 expression in each region and GAPDH was used as an internal control.

Blood collection and RNA isolation: For QRT-PCR, blood (2.5 ml) from each individual was collected into a PAXgene™ Blood RNA tube (QIAGEN) following the manufacturer's protocol. Whole blood was thoroughly mixed with PAXgene™ stabilization reagent and stored at room temperature for 6 hours prior to RNA extraction. Total RNA was then extracted using the PAXgene™ Blood RNA kit according to the manufacturer's directions (QIAGEN). In order to remove contaminating genomic DNA, total RNA samples absorbed to the PAXgene™ Blood RNA System spin column was incubated with DNase I (QIAGEN) at 25° C. for 20 min to remove genomic DNA. Total RNA was eluted, quantitated, and QRT-PCR is performed as previously mentioned to compare PAX2 and DEFB1 expression ratios.

9.2 Results

Figure 28:
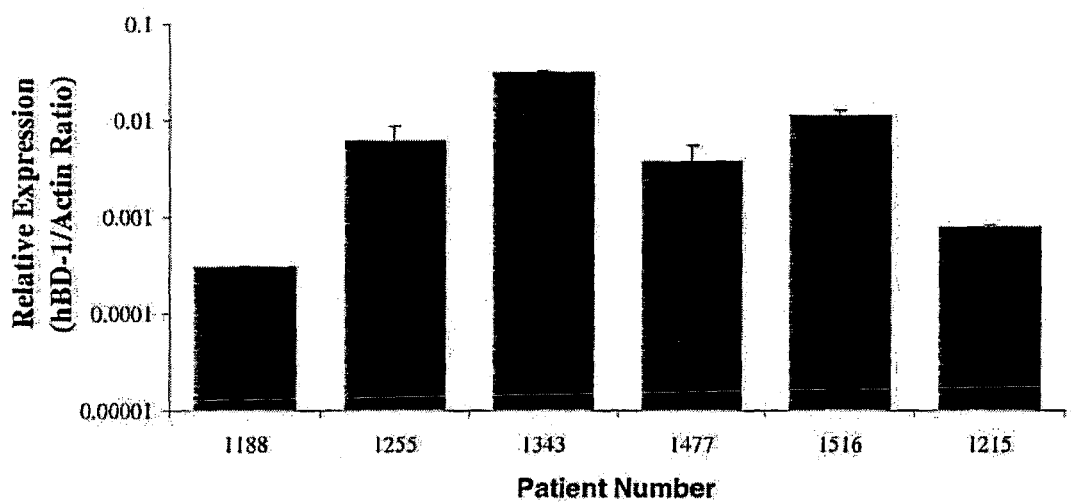
FIG. 28 shows a QRT-PCR analysis of DEFB1 (hBD-1) expression in prostate tissue sections being correlated with Gleason scores, where Patient Numbers 1255, 1343, 1477, and 1516 with relative DEFB1 expression levels greater than 0.005 had Gleason scores of 6, and where Patient Numbers 1188 and 1215 with DEFB1 expression levels lower than 0.005 had Gleason scores of 7.

In FIG. 28, a QRT-PCR analysis of prostate tissue sections from Patient Numbers 1255, 1343, 1477, and 1516 showed relative DEFB1 expression levels greater than 0.005 correlated with a Gleason score of 6, whereas Patient Numbers 1188 and 1215 with DEFB1 expression levels lower than 0.005 had Gleason scores of 7. Thus, there is an inverse relationship between DEFB1 expression and Gleason score, which is further confirmed in FIG. 29A. Conversely, there was a positive correlation between PAX2 expression and Gleason score in malignant prostate tissue and PIN as shown in FIG. 29B.

Figure 29A:
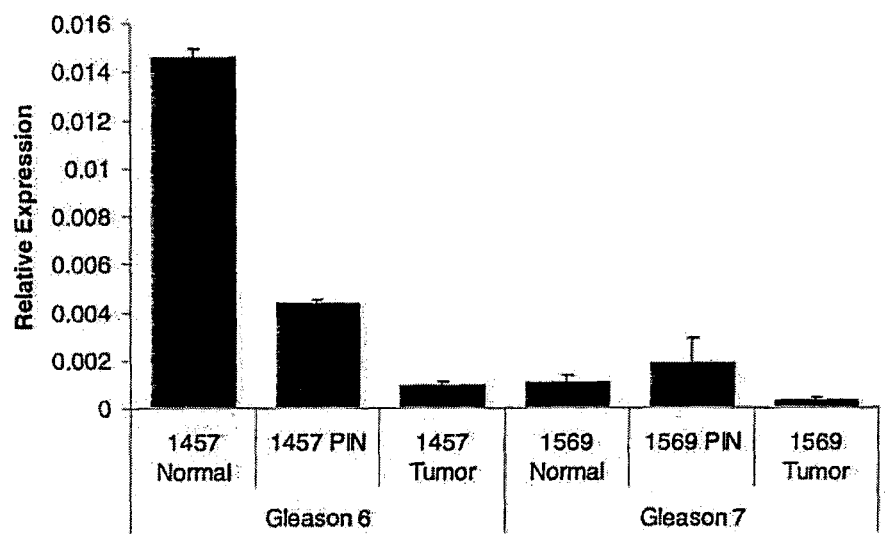
FIGS. 29A and 29B show QRT-PCR analyses of DEFB1 expression (FIG. 29A) and PAX2 expression (FIG. 29B) in normal, PIN, and cancerous tissues from separate patients showing an inverse correlation between DEFB expression and Gleason score in FIG. 29A and a positive correlation between PAX2 expression and Gleason score in FIG. 29B.
Figure 29B:
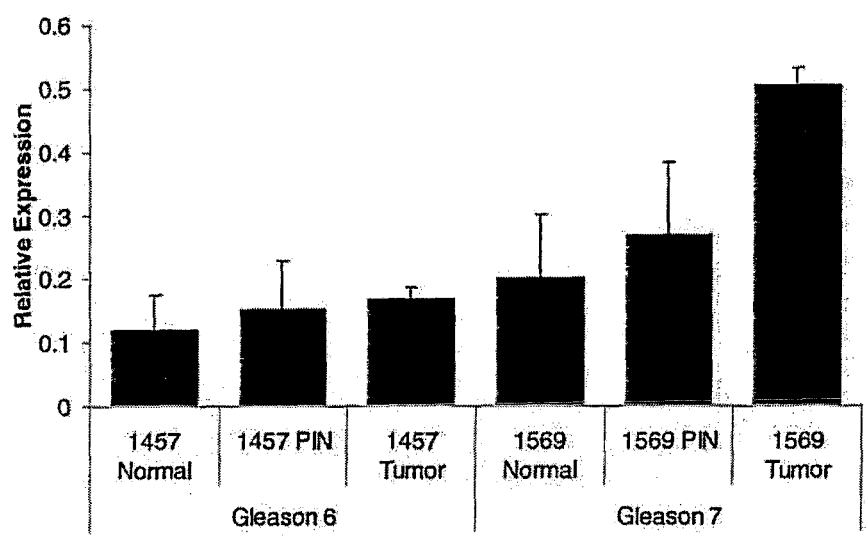
Figure 30:
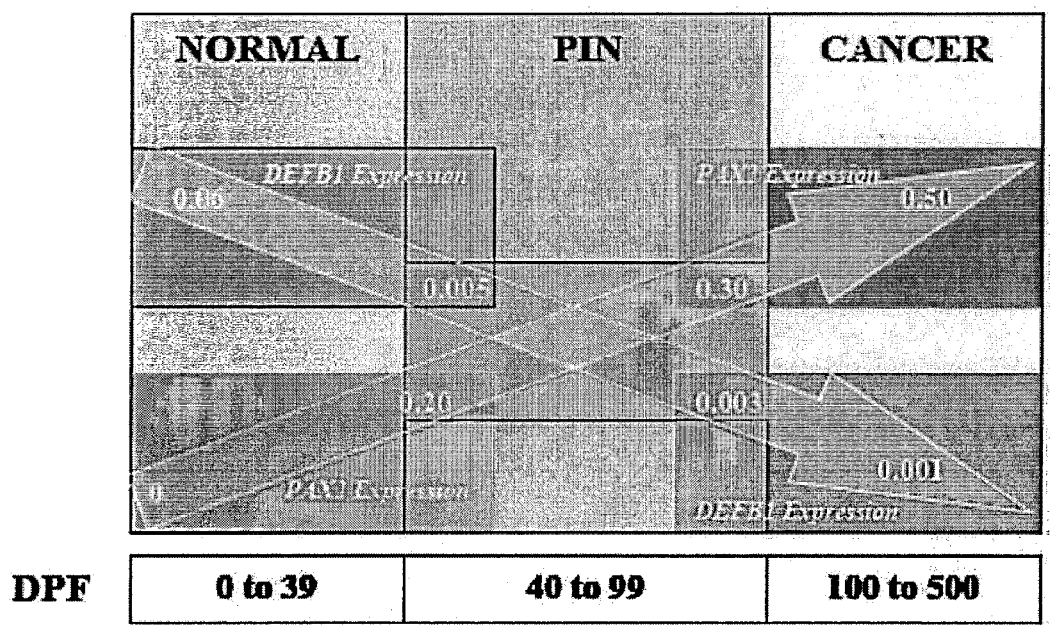
FIG. 30 shows the Donald Predictive Factor (DPF) based on the relative PAX2-DEFB1 expression ratio.

In FIGS. 29A and 29B, normal, PIN, and cancerous tissues from separate patients were tested and compared for relative DEFB1 (FIG. 29A) and PAX2 (FIG. 29B) expression levels. Overall, PAX2 expression levels relative to GAPDH internal control ranged between 0 and 0.2 in normal (benign) tissue, 0.2 and 0.3 in PIN, and between 0.3 and 0.5 in cancerous (malignant) tissue (FIG. 29B). For DEFB1, there was an inverse relationship compared to PAX2. DEFB1 expression levels relative to GAPDH internal control ranged between 0.06 and 0.005 in normal (benign) tissue, 0.005 and 0.003 in PIN, and between 0.003 and 0.001 in cancerous (malignant) tissue. Therefore, disclosed is a predictive scale, designated as the Donald Predictive Factor (DPF), which utilizes the PAX2-DEFB1 expression ratio as a prognosticator of benign, precancerous (PIN) and malignant prostate tissue. Tissues with PAX2-DEFB1 ratios between 0 and 39 based on the DPF represents normal (pathologically benign) prostate tissue. Tissue with a PAX2-DEFB1 ratio between 40 and 99 is representative of PIN (pre-cancerous) tissue, based on the DPF scale. Finally, tissue with a PAX2-DEFB1 ratio between 100 and 500 represents malignant tissue (low to high grade cancer).

There currently is a critical need for predictive biomarkers for prostate cancer development. It is known that the onset of prostate cancer occurs long before the disease is detectable by current screening methods such as the PSA test or the digital rectal exam. It is thought that a reliable test which could monitor the progression and early onset of prostate cancer would greatly reduce the mortality rate through more effective disease management. Disclosed herein is a predictive index to allow physicians to know well in advance the pathological state of the prostate. The DPF measures the decrease in the PAX2-DEFB1 expression ratio associated with prostate disease progression. This powerful measure can not only predict the likelihood of a patient developing prostate cancer, but also may pinpoint the early onset of pre-malignant cancer. Ultimately, this tool can allow physicians to segregate which patients have more aggressive disease from those which do not.

The identification of cancer-specific markers has been utilized to help identify circulating tumor cells (CTCs). There is also emerging evidence which demonstrates that detection of tumor cells disseminated in peripheral blood can provide clinically important data for tumor staging, prognostication, and identification of surrogate markers for early assessment of the effectiveness of adjuvant therapy. Furthermore, by comparing gene expression profiling of all circulating cells, one can examine the expression of the DEFB1 and PAX2 genes which play a role in "immunosurveillance" and "cancer survival", respectively as a prognosticator for the early detection of prostate cancer.

EXAMPLE 10

Functional Analysis of the Host Defense Peptide Human Beta Defensin-1: New Insight into its Potential Role in Cancer 10.1 Materials and Methods Cell culture: hPrEC cells and DU145, LnCap, and PC3 cell lines were cultured as described in Example 1.

Tissue samples and laser capture microdissection: Prostate tissues were obtained from patients who provided informed consent prior to undergoing radical prostatectomy. Samples were acquired through the Hollings Cancer Center tumor bank in accordance with an Institutional Review Board-approved protocol. This included guidelines for the processing, sectioning, histological characterization, RNA purification and PCR amplification of samples. Prostate specimens received from the surgeons and pathologists were immediately frozen in OCT compound. Each OCT block was cut to produce serial sections which were stained and examined. Areas containing benign cells, prostatic intraepithelial neoplasia (PIN), and cancer were identified and used to guide our selection of regions from unstained slides using the Arcturus PixCell II System (Sunnyvale, Calif.). Caps containing captured material were exposed to 20 µl of lysate from the Arcturus Pico Pure RNA Isolation Kit and processed immediately. RNA quantity and quality was evaluated using sets of primers that produce 5' amplicons. The sets include those for the ribosomal protein L32 (the 3' amplicon and the 5' amplicon are 298 bases apart), for the glucose phosphate isomerase (391 bases apart), and for the glucose phosphate isomerase (842 bases apart). Ratios of 0.95 to 0.80 were routinely obtained for these primer sets using samples from a variety of prepared tissues. Additional tumor and normal samples were grossly dissected by pathologists, snap frozen in liquid nitrogen and evaluated for hBD-1 and cMYC expression.

Cloning of hBD-1 gene: hBD-1 cDNA was generated from RNA by reverse transcription-PCR using primers generated from the published hBD-1 sequence (accession no. U50930) (Ganz, 2004). The PCR primers were designed to contain ClaI and KpnI restriction sites. hBD-1 PCR products were restriction digested with ClaI and KpnI and ligated into a TA cloning vector. The TA/hBD-1 vector was then transfected into the XL-1 Blue strain of *E. coli* by heat shock and individual clones were selected and expanded. Plasmids were isolated by Cell Culture DNA Midiprep (Qiagen, Valencia, Calif.) and sequence integrity verified by automated sequencing. The hBD-1 gene fragment was then ligated into the pTRE2 digested with ClaI and KpnI, which served as an intermediate vector for orientation purposes. The pTRE2/hBD-1 construct was digested with ApaI and KpnI to excise the hBD-1 insert. The insert was ligated into pIND vector of the Ecdysone Inducible Expression System (Invitrogen, Carlsbad, Calif.) also double digested with ApaI and KpnI. The construct was transfected into *E. coli* and individual clones were selected and expanded. Plasmids were isolated and sequence integrity of pIND/hBD-1 was again verified by automated sequencing.

Cell transfections: Cells ($1 \times 10^6$) were seeded onto 100-mm Petri dishes and grown overnight. Next, the cells were co-transfected using Lipofectamine 2000 (Invitrogen) with 1 µg of pvgRXR plasmid, which expresses the heterodimeric ecdysone receptor, and 1 µg of the pIND/hBD-1 vector construct or pIND/β-galactosidase (β-gal) control vector in Opti-MEM media (Life Technologies, Inc.). Transfection efficiency was determined by inducing β-gal expression with Ponasterone A (PonA) and staining cells with a β-galactosidase detection kit (Invitrogen). Assessment of transfection efficiency by counting positive staining (blue) colonies which demonstrated that 60-85% of cells expressed β-galactosidase for the cell lines.

Immunocytochemistry: In order to verify hBD-1 protein expression, DU145 and hPrEC cells were seeded onto 2-chamber culture slides (BD Falcon, USA) at $1.5-2 \times 10^4$ cells per chamber. DU145 cells transfected with pvgRXR alone (control) or with the hBD-1 plasmid were induced for 18 h with media containing 10 µM PonA, while untransfected cells received fresh growth media. Following induction, cells were washed in 1×PBS and fixed for 1 h at room temperature with 4% paraformaldehyde. Cells were then washed six times with 1×PBS and blocked in 1×PBS supplemented with 2% BSA, 0.8% normal goat serum (Vector Laboratories, Inc., Burlingame, Calif.) and 0.4% Triton-X 100 for 1 h at room temperature. Next, cells were incubated overnight in primary rabbit anti-human BD-1 polyclonal antibody (PeproTech Inc., Rocky Hill, N.J.) diluted 1:1000 in blocking solution. Following this, cells were washed six times with blocking solution and incubated for 1 h at room temperature in Alexa Fluor 488 goat anti-rabbit IgG (H+L) secondary antibody at a dilution of 1:1000 in blocking solution. After washing cells with blocking solution six times, coverslips were mounted with Gel Mount (Biomeda, Foster City, Calif.). Finally, cells were viewed under differential interference contrast (DIC) and under laser excitation at 488 nm. The fluorescent signal was analyzed by confocal microscopy (Zeiss LSM 5 Pascal) using a 63×DIC oil lens with a Vario 2 RGB Laser Scanning Module. The digital images were exported into Photoshop CS Software (Adobe Systems) for image processing and hard copy presentation.

RNA isolation and quantitative RT-PCR: QRT-PCR was performed as previously described (Gibson et al., 2007). Briefly, total RNA (0.5 µg per reaction) from tissue sections were reverse transcribed into cDNA utilizing random primers (Promega). Two-step QRT-PCR was performed on cDNA generated using the MultiScribe Reverse Transcriptase from the TaqMan Reverse Transcription System and the SYBR Green PCR Master Mix (Applied Biosystems, Foster City, Calif.). The primer pairs for hBD-1 and c-MYC were generated from the published sequences (Table 5). Forty cycles of PCR were performed under standard conditions using an annealing temperature of 56.4° C. for hBD-1 and c-MYC and 55° C. for PAX2. In addition, β-actin (Table 5) was amplified as a housekeeping gene to normalize the initial content of total cDNA. Gene expression in benign prostate tissue samples was calculated as the expression ratio compared to β-actin. Levels of hBD-1 expression in malignant prostate tissue, hPREC prostate primary culture, and prostate cancer cell lines before and after induction were calculated relative to the average level of hBD-1 expression in hPrEC cells. As a negative control, QRT-PCR reactions without cDNA template were also performed. All reactions were run a minimum of three times.

TABLE 5

Sequences of QRT-PCR primers

|  | Sense (5'-3') | Antisense (5'-3') |
|---|---|---|
| β-Actin | CCTGGCACCCAGCACAAT (SEQ ID NO: 51) | GCCGATCCACACGGAGTACT (SEQ ID NO: 52) |
| hBD-1 | TCAGCAGTGGAGGGCAATG (SEQ ID NO: 65) | CCTCTGTAACAGGTGCCTTG AAT (SEQ ID NO: 66) |
| cMYC | ACAGCAAACCTCCTCACAG CC (SEQ ID NO: 67) | TGGAGACGTGGCACCTCTTG (SEQ ID NO: 68) |

MTt cell viability assay: To examine the effects of hBD-1 on cell growth, metabolic 3-[4,5-dimethylthiazol-2yl]-2,5-diphenyl tetrazolium bromide (MTT) assay was performed. DU145, LNCaP, PC3 and PC3/AR+cells co-transfected with pvgRXR plasmid and pIND/hBD-1 construct or control pvgRXR plasmid were seeded onto a 96-well plate at $1-5 \times 10^3$ cells per well. Twenty-four hours after seeding, fresh growth medium was added containing 10 µM Pon A daily to induce hBD-1 expression for 24, 48 and 72 h after which the MTT assay was performed according to the manufacturer's instructions (Promega). Reactions were performed three times in triplicate.

Analysis of membrane integrity: Acridine orange (AO)/ethidium bromide (EtBr) dual staining was performed to identify changes in cell membrane integrity, as well as apoptotic cells by staining the condensed chromatin. AO stains viable cells and early apoptotic cells, whereas EtBr stains late stage apoptotic cells that have compromised membranes. Briefly, PC3, DU145 and LNCaP cells were seeded into 2-chamber culture slides (BD Falcon). Cells transfected with empty plasmid or hBD-1 plasmid were induced for 24 or 48 h with media containing 10 µM Pon A, while control cells received fresh growth media at each time point. After induction, cells were washed once with PBS and stained with 2 ml of a mixture (1:1) of AO (Sigma, St. Louis, Mo.) and EtBr (Promega) (5 µg/ml) solution for 5 min and were again washed with PBS.

Fluorescence was viewed by a Zeiss LSM 5 Pascal Vario 2 Laser Scanning Confocal Microscope (Carl Zeiss). The excitation color wheel contains BS505-530 (green) and LP560 (red) filter blocks which allowed for the separation of emitted green light from AO into the green channel and red light from EtBr into the red channel. The laser power output and gain control settings within each individual experiment were identical between control and hBD-1 induced cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems) for image processing and hard copy presentation.

Flow cytometry: PC3 and DU145 cells transfected with the hBD-1 expression system were grown in 60-mm dishes and induced for 12, 24, and 48 h with 10 µM Pon A. The cells were harvested and analyzed by flow cytometry as described in Example 1.

Caspase detection: Detection of caspase activity in the prostate cancer cell lines was performeds described in Example 1.

siRNA silencing of PAX2: SiRNA knock-down and verification was performed as described in Example 2.

Figure 31A:
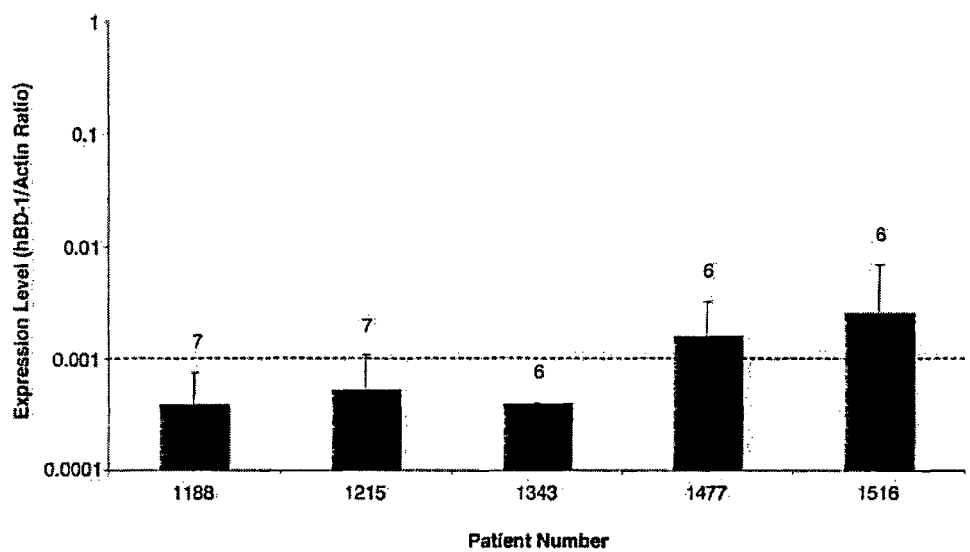
FIGS. 31A and 31B show an analysis of DEFB1 (hBD-1) expression in human prostate tissues.
Figure 31B:
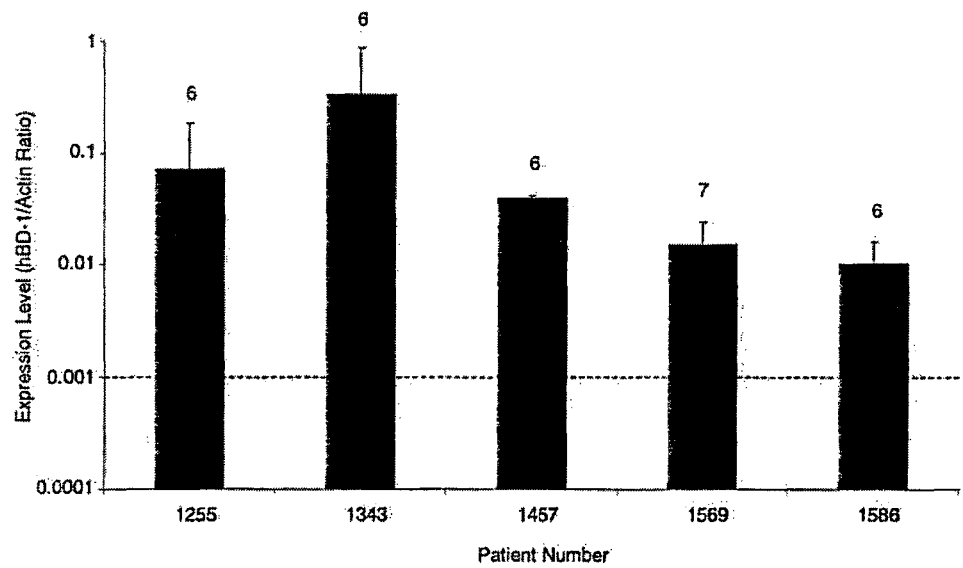
Figure 32A:
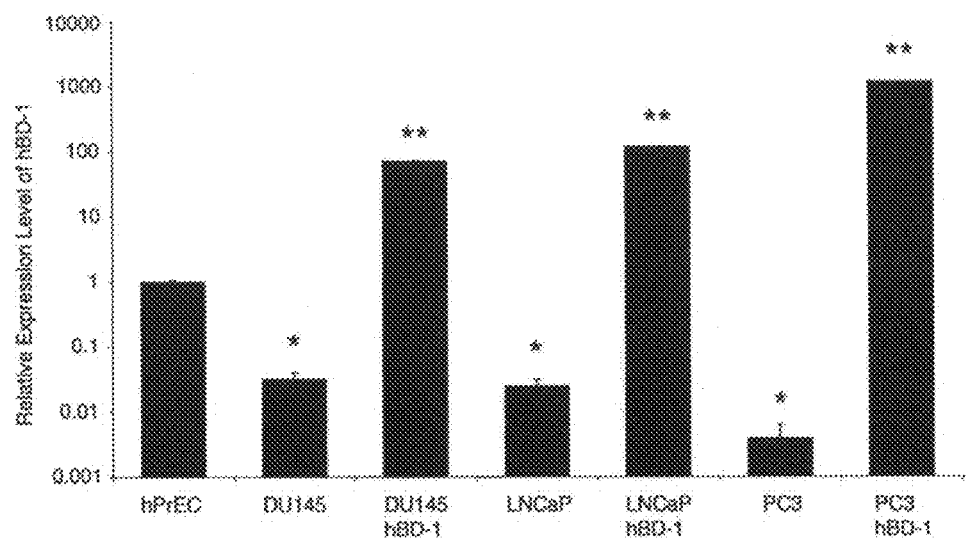
FIG. 32A shows an analysis of DEFB1 (hBD-1) expression in prostate cells, including expression before and after induction of DEFB1 expression in prostate cancer cell lines transfected with a DEFB1 (hBD-1) expression system inducible with Ponasterone A (Pon A).

10.2 Results hBD-1 expression in prostate tissue: 82% of prostate cancer frozen tissue sections analyzed exhibited little or no expression of hBD-1 (Donald et al., 2003). To compare hBD-1 expression levels, QRT-PCR analysis was performed on normal prostate tissue obtained by gross dissection or LCM of normal prostate tissue adjacent to malignant regions which were randomly chosen. hBD-1 was detected in all of the gross dissected normal clinical samples with a range of expression that represents approximately a 6.6-fold difference in expression levels (FIG. 31A). LCM captured normal tissue samples expressed hBD-1 at levels in a range that represents a 32-fold difference in expression (FIG. 31B). Matching sample numbers to corresponding patient profiles revealed that in most cases, the hBD-1 expression level was higher in patient samples with a Gleason score of 6 than in patient samples with a Gleason score of 7. In addition, a comparison of hBD-1 expression levels in tissue obtained by gross dissection and LCM from the same patient, #1343, demonstrated an 854-fold difference in expression between the two isolation techniques. Therefore, these results indicate that LCM provides a more sensitive technique to assess hBD-1 expression in prostate tissue.

hBD-1 expression in prostate cell lines: To verify upregulation of hBD-1 in the prostate cancer cell lines, QRT-PCR was performed in cells transfected with a DEFB1 (hBD-1) expression system inducible with Ponasterone A (Pon A). In addition, no template negative controls were also performed, and amplification products were verified by gel electrophoresis. FIG. 32A shows hBD-1 expression levels compared relative to hPrEC cells in prostate cancer cell lines before and after hBD-1 induction. hBD-1 expression was significantly lower in the prostate cancer cell lines compared to hPrEC cells. Following a 24 h induction period, relative expression levels of hBD-1 significantly increased in DU145, PC3 and LNCaP as compared to the cell lines prior to hBD-1 induction. In FIG. 32A, an asterisk represents statistically higher expression levels compared to hPrEC. Double asterisks represent statistically significant levels of expression compared to the cell line before hBD-1 induction (Student's t-test, $p<0.05$).

Figure 32B:
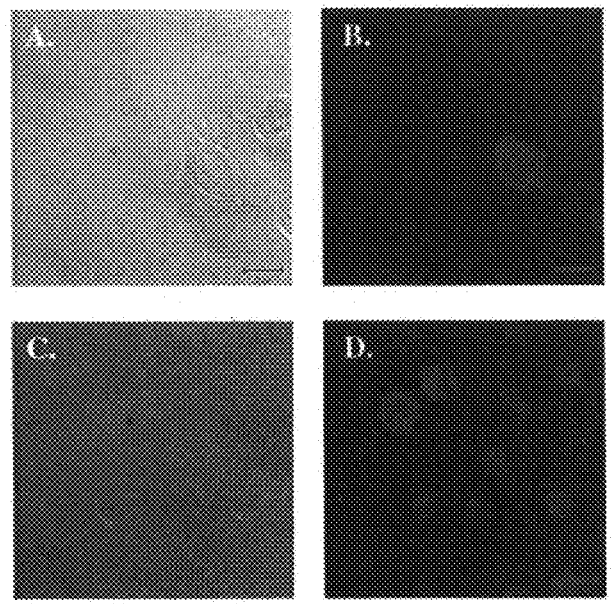
FIG. 32B shows DEFB1 (hBD-1) expression levels in positive control hPrEC cells (Panel A: DIC and Panel B: fluorescence) and in DU145 prostate cancer cells transfected with hBD-1 and following induction with Pon A (Panel C: DIC and Panel D: fluorescence).

FIG. 32B shows verification of hBD-1 expression by immunocytochemistry in hPrEC cells as a positive control (Panel A: DIC and Panel B: fluorescence) and in DU145 cells (Panel C: DIC and Panel D: fluorescence) transfected with hBD-1 and induced with Pon A. Cells were stained with primary antibody against hBD-1 and protein expression was monitored based on the green fluorescence of the secondary antibody, wherein excitation by the confocal laser at 488 nm produced green fluorescence indicative of the presence of hBD-1 protein in the hPrEC positive control. There was no detectable green fluorescence in control DU145 cells or empty plasmid induced DU145 cells (data not shown). However, confocal analysis of DU145 cells induced for hBD-1 expression revealed green fluorescence indicating the presence of hBD-1 protein following induction with Pon A (Panel D). Sizebar=20 µM.

Figure 33:
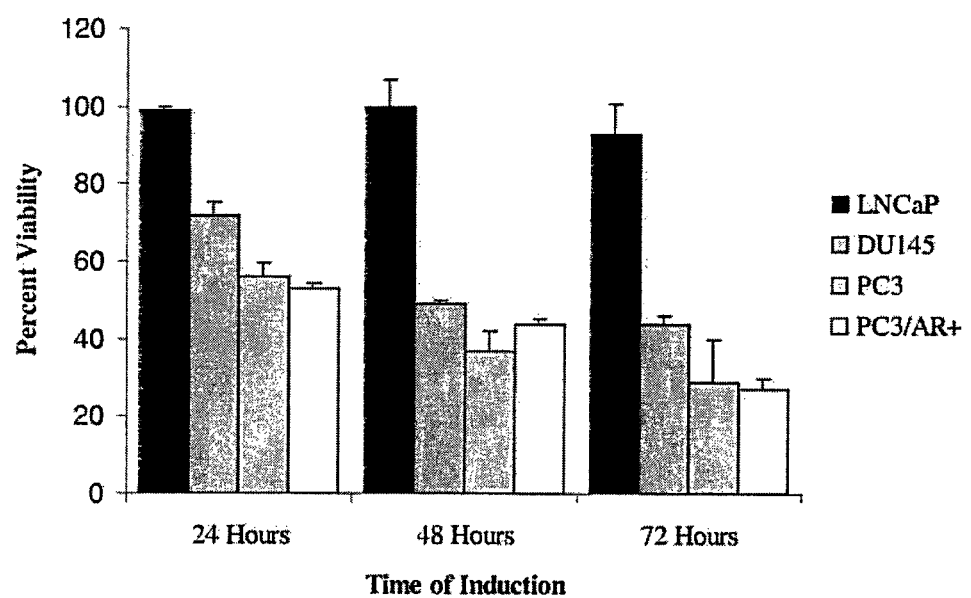
FIG. 33 shows analysis of hBD-1 cytotoxicity in prostate cancer cells. Each bar represents the mean±S.E.M. of three independent experiments performed in triplicate.

Expression of hBD-1 results in decreased cell viability: MTT assay was performed to assess the effect of hBD-1 expression on relative cell viability in DU145, PC3, PC3/AR+ and LNCaP prostate cancer cell lines. MTT analysis with empty vector exhibited no statistical significant change in cell viability. Twenty-four hours following hBD-1 induction, relative cell viability was 72% in DU145 and 56% in PC3 cells, and after 48 h cell viability was reduced to 49% in DU145 and 37% in PC3 cells (FIG. 33). Following 72 h of hBD-1 induction, relative cell viability decreased further to 44% in DU145 and 29% PC3 cells. Conversely, there was no significant effect on the viability of LNCaP cells. In order to assess whether the resistance to hBD-1 cytotoxicity observed in LNCaP was due to the presence of the androgen receptor (AR), the hBD-1 cytotoxicity in PC3 cells was examined with ectopic AR expression (PC3/AR+). There was no difference between PC3/AR+ and PC3 cells. Therefore, the data indicates that that hBD-1 is cytotoxic specifically to late-stage prostate cancer cells.

To determine whether the effects of hBD-1 on PC3 and DU145 were cytostatic or cytotoxic, FACS analysis was performed to measure cell death. Under normal growth conditions, more than 90% of PC3 and DU145 cultures were viable and non-apoptotic (lower left quadrant) and did not stain with annexin V or PI. After inducing hBD-1 expression in PC3 cells, the number of cells undergoing early apoptosis and late apoptosis/necrosis (lower and upper right quadrants, respectively) totaled 10% at 12 h, 20% at 24 h, and 44% at 48 h (FIG. 4B). For DU145 cells, the number of cells undergoing early apoptosis and late apoptosis/necrosis totaled 12% after 12 h, 34% at 24 h, and 59% after 48 h of induction (FIG. 4A). No increase in apoptosis was observed in cells containing empty plasmid following induction with Pon A. Annexin V and propidium iodide uptake studies have demonstrated that hBD-1 has cytotoxic activity against DU145 and PC3 prostate cancer cells and results indicate apoptosis as a mechanism of cell death.

hBD-1 causes alterations in membrane integrity and caspase activation: It was investigated whether the cell death observed in prostate cancer cells after hBD-1 induction is caspase-mediated apoptosis. To better understand the cellular mechanisms involved in hBD-1 expression, confocal laser microscopic analysis was performed (FIG. 5) on DU145 and LNCaP cells induced for hBD-1 expression. Pan-caspase activation was monitored based on the binding and cleavage of green fluorescing FAM-VAD-FMK to caspases in cells actively undergoing apoptosis. Analysis of cells under DIC showed the presence of viable control DU145 (panel A) and LNCaP (panel E) cells at 0h. Excitation by the confocal laser at 488 nm produced no detectable green staining which indicates no caspase activity in DU145 (panel B) or LNCaP (panel F) control cells. Following induction for 24 h, DU145 (panel C) and LNCaP (panel G) cells were again visible under DIC. Confocal analysis under fluorescence revealed green staining in DU145 (panel D) cells indicating pan-caspase activity after the induction of hBD-1 expression. However, there was no green staining in LNCaP (panel H) cells induced for hBD-1 expression. Therefore, cell death observed following induction of hBD-1 is caspase-mediated apoptosis.

The proposed mechanism of antimicrobial activity of defensin peptides is the disruption of the microbial membrane due to pore formation (Papo and Shai, 2005). In order to determine if hBD-1 expression altered membrane integrity EtBr uptake was examined by confocal analysis. Intact cells were stained green due to AO which is membrane permeable, while only cells with compromised plasma membranes stained red due to incorporation of membrane impermeable EtBr. Control DU145 and PC3 cells stained positively with AO and emitted green color, but did not stain with EtBr. However, hBD-1 induction in both DU145 and PC3 resulted in the accumulation of EtBr in the cytoplasm at 24 as indicated by the red staining. By 48 h, DU145 and PC3 possessed condensed nuclei and appeared yellow due to the colocalization of green and red staining from AO and EtBr, respectively. Conversely, there were no observable alterations to membrane integrity in LNCaP cells after 48 h of induction as indicated by positive green fluorescence with AO, but lack of red EtBr fluorescence. This finding indicates that alterations to membrane integrity and permeabilization in response to hBD-1 expression differ between early- and late-stage prostate cancer cells.

Figure 34A:
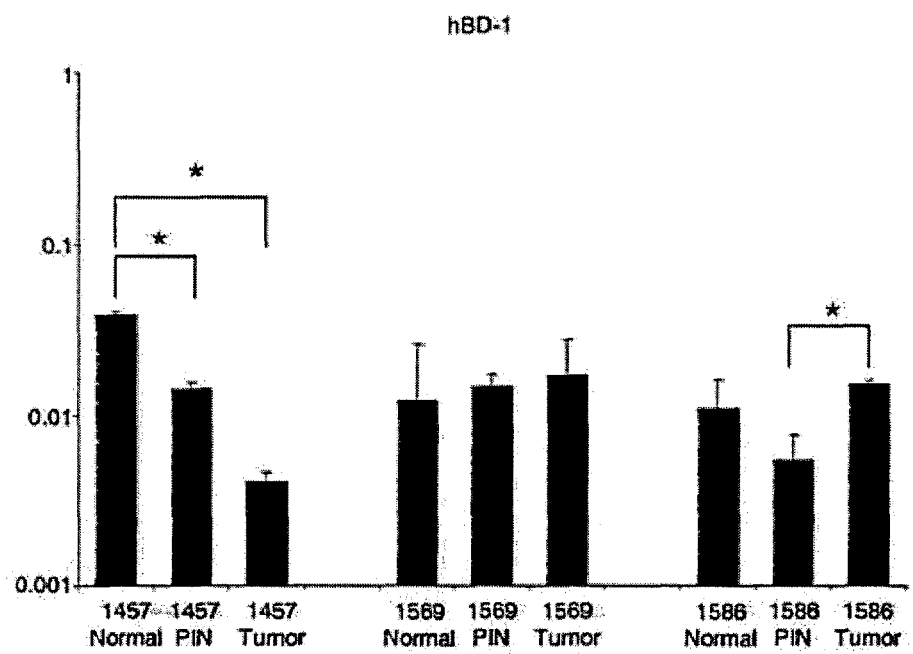
FIG. 34A shows a QRT-PCR analysis of hBD-1 expression levels in LCM human prostate tissue sections of normal, PIN and tumor tissue.
Figure 34B:
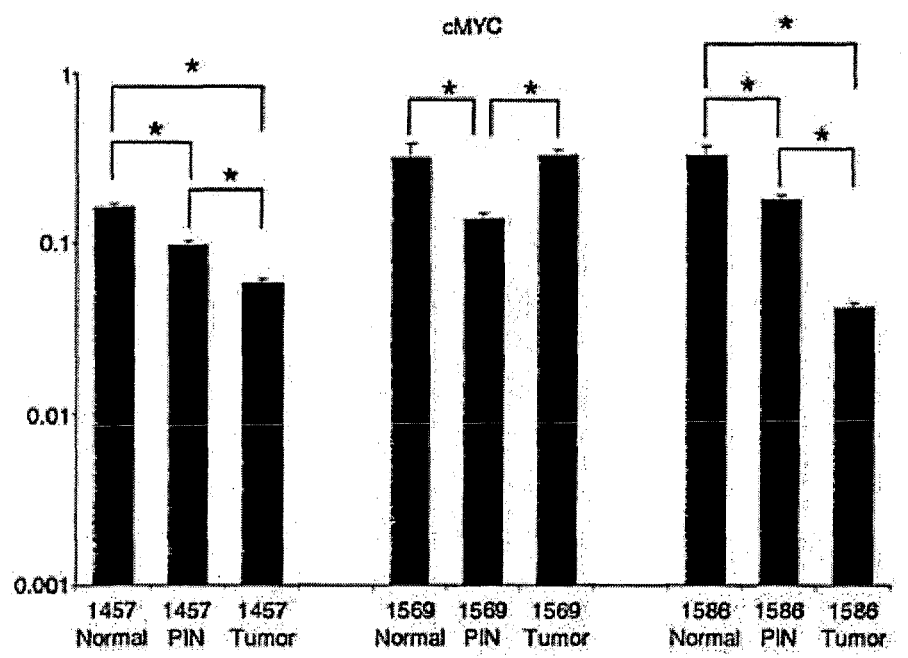
FIG. 34B shows a QRT-PCR analysis of cMYC expression levels in LCM human prostate tissue sections of normal, PIN and tumor tissue.

Comparison of hBD-1 and cMYC expression levels: QRT-PCR analysis was performed on LCM prostate tissue sections from three patients (FIG. 32). In patient #1457, hBD-1 expression exhibited a 2.7-fold decrease from normal to PIN, a 3.5-fold decrease from PIN to tumor and a 9.3-fold decrease from normal to tumor (FIG. 34A). Likewise, cMYC expression followed a similar expression pattern in patient #1457 where expression decreased by 1.7-fold from normal to PIN, 1.7-fold from PIN to tumor and 2.8-fold from normal to tumor (FIG. 34B). In addition, there was a statistically significant decrease in cMYC expression in the other two patients. Patient #1569 had a 2.3-fold decrease from normal to PIN, while in patient #1586 there was a 1.8-fold decrease from normal to PIN, a 4.3-fold decrease from PIN to tumor and a 7.9-fold decrease from normal to tumor.

Figure 35:
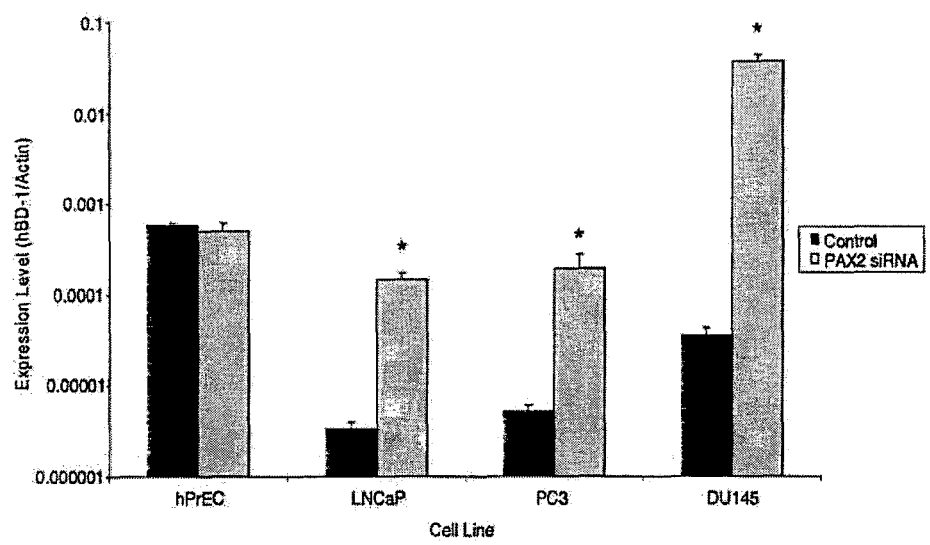
FIG. 35 shows a QRT-PCR analysis of hBD1 expression following PAX2 knockdown with siRNA.

Induction of hBD-1 expression following PAX2 inhibition: To further examine the role of PAX2 in regulating hBD-1 expression, siRNA was utilized to knock-down PAX2 expression and QRT-PCR performed to monitor hBD-1 expression. Treatment of hPrEC cells with PAX2 siRNA exhibited no effect on hBD-1 expression (FIG. 35). However, PAX2 knockdown resulted in a 42-fold increase in LNCaP, a 37-fold increase in PC3 and a 1026-fold increase in DU145 expression of hBD-1 compared to untreated cells. As a negative control, cells were treated with non-specific siRNA which had no significant effect on hBD-1 expression. In FIG. 35, hBD-1 expression levels are presented as expression ratios compared to β-actin. An asterisk represents statistically higher expression levels compared to the cell line before PAX2 siRNA treatment (Student's t-test, p<0.05).

EXAMPLE 11

Inhibition of PAX2 Expression Results in Alternate Cell Death Pathways in Prostate Cancer Cells Differing in P53 Status 11.1 Materials and Methods Cell lines: The cancer cell lines PC3, DU145 and LNCaP, which all differ in p53 mutational status (Table 6), were cultured as described in Example 1. The prostate epithelial cell line hPrEC was obtained from Cambrex Bio Science, Inc., (Walkersville, Md.) and were cultured in prostate epithelium basal media. Cells were maintained at 37° C. in 5% $CO_2$.

TABLE 6 p53 gene mutation in prostate cancer cell lines

| Nucleotide change | Amino acid change | Gene status | Reference |
|---|---|---|---|
| CCT-CTT | Pro-Leu | Gain/loss-of-function | Tepper et al. 2005; Bodhoven et al. 2003 |
| GTT-TTT Deleted a C, GCC-GC | Val-Phe Frame-shift | No activity | Isaacs et al. 1991 |
| No deletion, wild-type | — | Normal function | Carroll et al. 1993 | siRNA silencing of PAX2: siRNA silencing or PAX2 was performed as described in Example 2.

Western blot analysis: Western blot analysis was performed as described in Example 2.

Phase contrast microscopy: The effect of PAX2 knockdown on cell number was analyzed by phase contrast microscopy as described in Example 1.

MTT cytotoxicity assay: MTT cytotoxicity assay was performed as described in Example 1.

Pan-caspase detection: Detection of caspase activity in the prostate cancer cell lines was performed as described in Example 1.

Quantitative real-time RT-PCR: To verify changes in gene expression following PAX2 knockdown in PC3, DU145 and LNCaP cell lines, quantitative real-time RT-PCR was performed as described in Example 1. The primer pairs for BAX, BID, BCL-2, AKT and BAD were generated from the published sequences (Table 7). Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Relative expression was calculated as the ratio between each genes and GAPDH. All reactions were carried out in triplicate.

TABLE 7

Quantitative RT-PCR primers

| | Sense (5'-3') | Antisense (5'-3') |
|---|---|---|
| GAPDH | CCACCCATGGCAAATTCCAT GGCA (SEQ ID NO: 55) | TCTAGACGGCAGGTCAGGTC AACC (SEQ ID NO: 56) |
| BAD | CTCAGGCCTATGCAAAAAGA GGA (SEQ ID NO: 57) | GCCCTCCCTCCAAAGGAGAC (SEQ ID NO: 58) |
| BID | AACCTACGCACCTACGTGAG GAG (SEQ ID NO: 59) | CGTTCAGTCCATCCCATTTC TG (SEQ ID NO: 60) |
| BAX | GACACCTGAGCTGACCTTGG (SEQ ID NO: 61) | GAGGAAGTCCAGTGTCCAGC (SEQ ID NO: 62) |
| BCL-2 | TATGATACCCGGGAGATCGT GATC (SEQ ID NO: 69) | GTGCAGATGCCGGTTCAGGT ACTC (SEQ ID NO: 70) |
| AKT | TCAGCCCTGGACTACCTGCA (SEQ ID NO: 71) | GAGGTCCCGGTACACCACGT (SEQ ID NO: 72) |

Membrane permeability assay: Membrane permeability assay was performed s described in Example 3.

Analysis of PAX2 protein expression in prostate cells: PAX2 protein expression was examined by Western blot analysis in hPrEC prostate primary culture and in LNCaP, DU145 and PC3 prostate cancer cell lines. PAX2 protein was detected in all of the prostate cancer cell lines (FIG. 36A). However, no PAX2 protein was detectable in hPrEC. Blots were stripped and re-probed for β-actin as internal control to ensure equal loading. PAX2 protein expression was also monitored after selective targeting and inhibition by PAX2 specific siRNA in DU145, PC3 and LNCaP prostate cancer cell lines. Cells were given a single round of transfection with the pool of PAX2 siRNA over a 6-day treatment period. PAX2 protein was expressed in control cells treated with media only. Specific targeting of PAX2 mRNA was confirmed by observing knockdown of PAX2 protein in all three cell lines (FIG. 36B).

Figure 37:
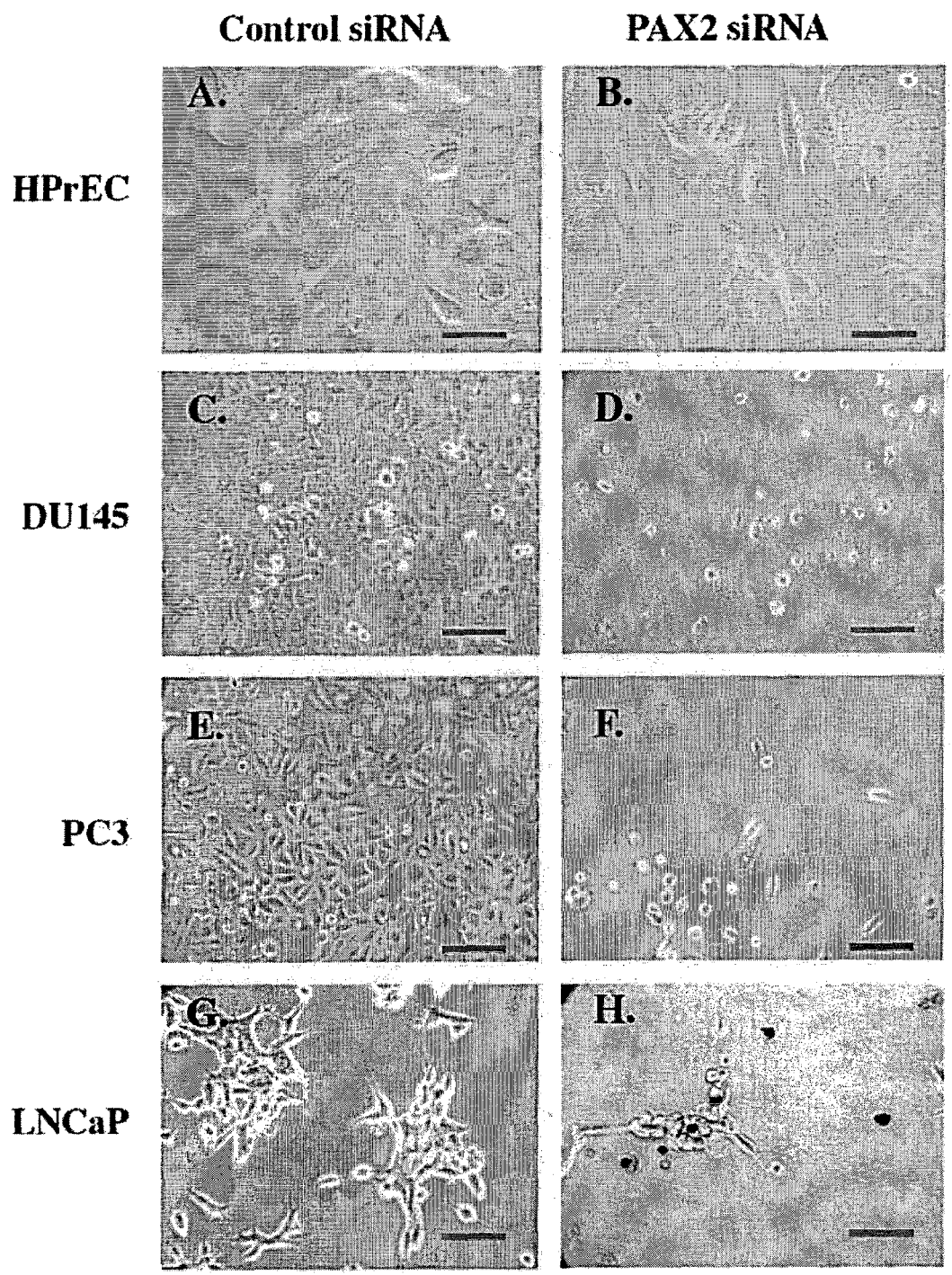
FIG. 37 shows an analysis of prostate cancer cell growth after treatment with PAX2 siRNA. Bar=20 μm.

Effect of PAX2 knockdown on prostate cancer cell growth: The effect of PAX2 siRNA on cell number and cell viability was analyzed using light microscopy and MTT analysis. To examine the effect of PAX2 siRNA on cell number, PC3, DU145 and LNCaP cell lines were transfected with media only, non-specific siRNA or PAX2 siRNA over a period of 6 days. Each of the cell lines reached a confluency of 80-90% in 60 mm culture dishes containing media only. Treatment of hPrEC, DU 145, PC3 and LNCaP cells with non-specific siRNA appeared to have little to no effect on cell growth compared to cell treated with media only (FIGS. 37A, 37C, and 37E, respectively). Treatment of the PAX2-null cell line HPrEC with PAX2 siRNA appeared to have no significant effect on cell growth (FIG. 37B). However, treatment of the prostate cancer cell lines DU145, PC3 and LNCaP with PAX2 siRNA resulted in a significant decrease in cell number (FIGS. 37D, 37F and 37H, respectively).

Figure 38:
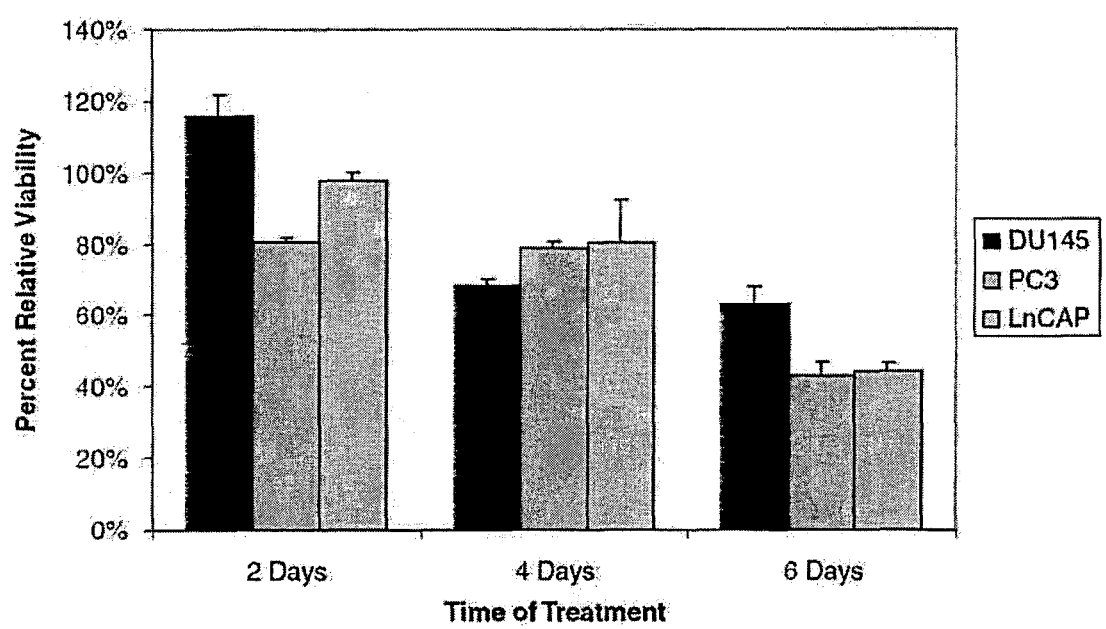
FIG. 38 shows an analysis of cell death following siRNA silencing of PAX2. Results represent mean±SD, n=9.

Effect of PAX2 knockdown on prostate cancer cell viability: Cell viability was measured after 2-, 4-, and 6-day exposure times. Percent viability was calculated as the ratio of the 570-630 nm absorbance of cell treated with PAX2 siRNA divided by untreated control cells. As negative controls, cell viability was measured after each treatment period with negative control non-specific siRNA or transfection with reagent alone. Relative cell viability was calculated by dividing percent viability following PAX2 siRNA treatment by percent viability following treatment with non-specific siRNA (FIG. 38). After 2 days of treatment, relative viability was 116% in DU145, 81% in PC3 and 98% in LNCaP. After 4 days of treatment, relative cell viability decreased to 69% in DU145, 79% in PC3, and 80% in LNCaP. Finally, by 6 days relative viability was 63% in DU145, 43% in PC3 and 44% in LNCaP. In addition, cell viability was also measured following treatment with transfection reagent alone. Each cell line exhibited no significant decrease in cell viability.

Figure 39:
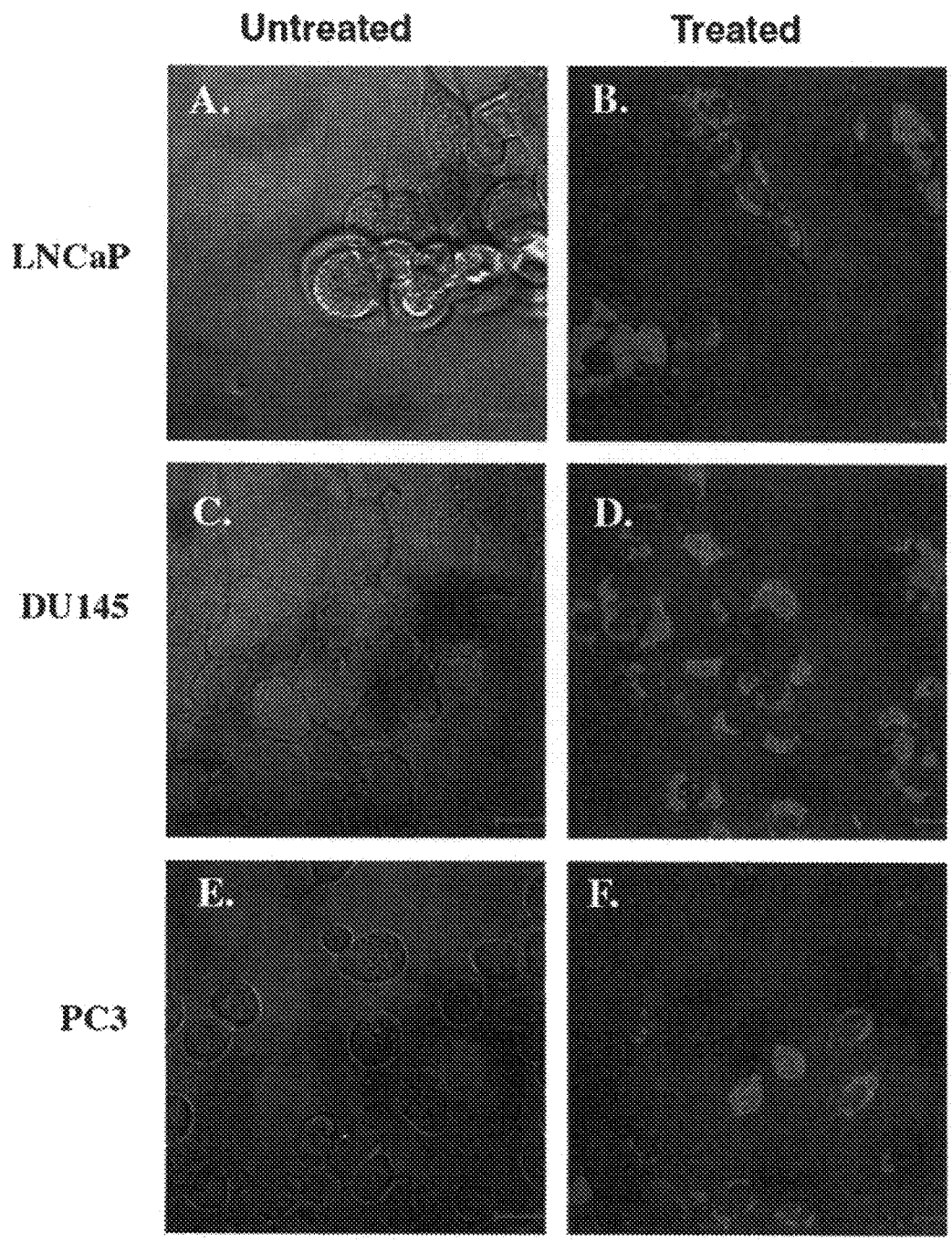
FIG. 39 shows an analysis of caspase activity. Bar=20 μm.

Detection of Pan-caspase activity: Caspase activity was detected by confocal laser microscopic analysis. LNCaP, DU145 and PC3 cells were treated with PAX2 siRNA and activity was monitored based on the binding of FAM-labeled peptide to caspases in cells actively undergoing apoptosis which will fluoresce green. Analysis of cells with media only shows the presence of viable LNCaP, DU145 and PC3 cells, respectively. Excitation by the confocal laser at 488 nm produced no detectable green staining which indicates no caspase activity in the untreated cells (FIGS. 39A, 39C and 39E, respectively). Following 4 days of treatment with PAX2 siRNA, LNCaP, DU145 and PC3 cells under fluorescence presented green staining indicating caspase activity (FIGS. 39B, 39D, and 39F, respectively).

Figure 40A:
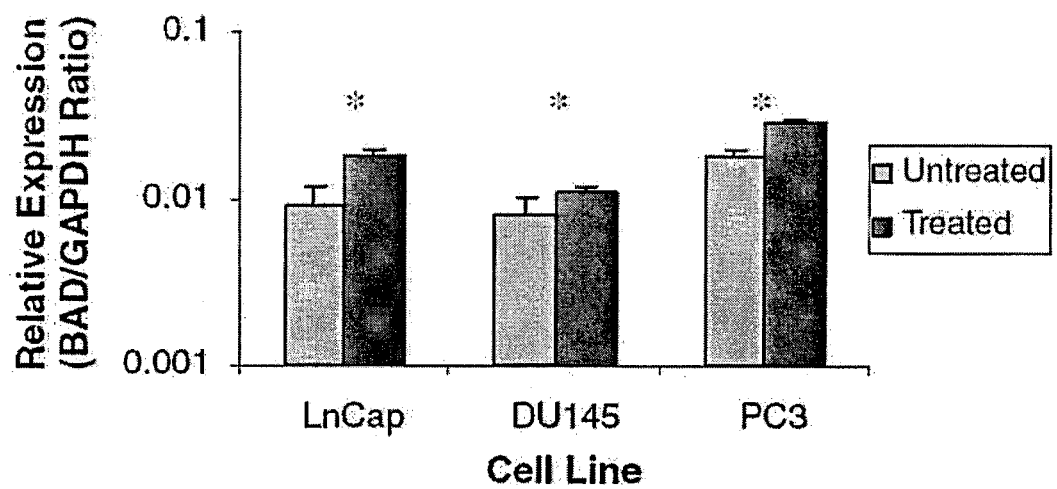
FIGS. 40A-40C show apoptotic factor expression patterns following PAX2 siRNA treatment. Results represent mean±SD, n=9. Asterisks represents statistical differences (p<0.05).
Figure 40B:
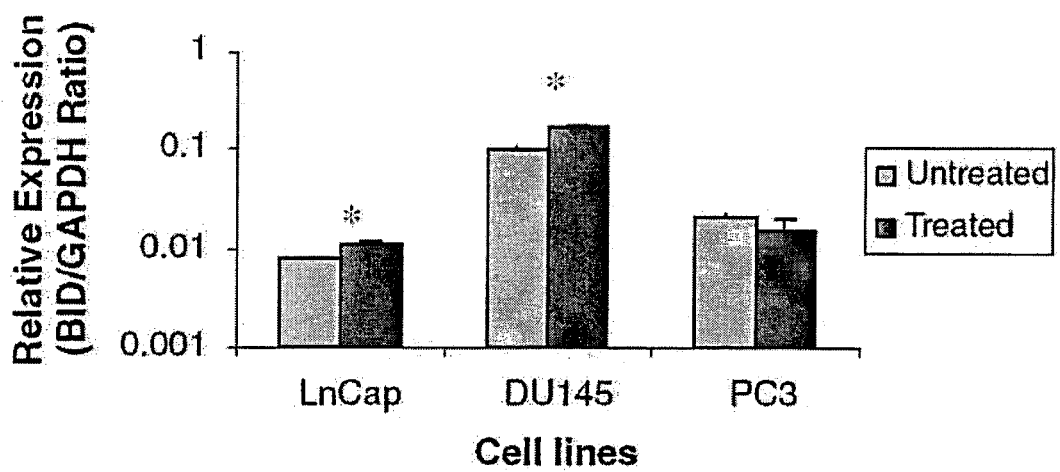
Figure 40C:
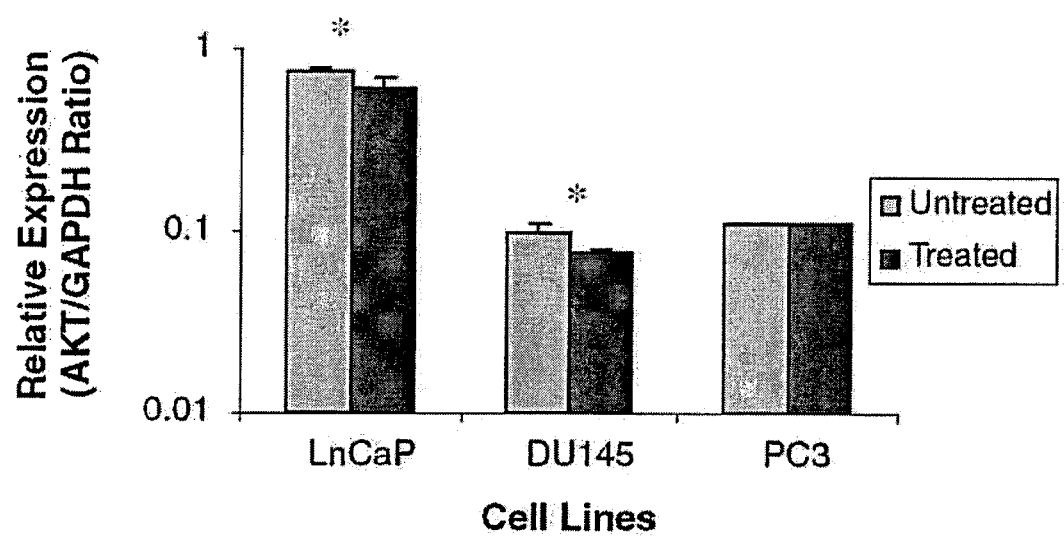

Effect of PAX2 inhibition on apoptotic factors: LNCaP, DU145 and PC3 cells were treated with siRNA against PAX2 for 4 days and expression of both pro- and anti-apoptotic factors were measured by QRT-PCR. Following PAX2 knockdown, analysis of BAD revealed a 2-fold in LNCaP, 1.58-fold in DU145 and 1.375 in PC3 (FIG. 40A). Expression levels of BID increased by 1.38-fold in LNCaP and a 1.78-fold increase in DU145, but there was no statistically significant difference in BID observed in PC3 after suppressing PAX2 expression (FIG. 40B). Analysis of the anti-apoptotic factor AKT revealed a 1.25-fold decrease in expression in LNCaP and a 1.28-fold decrease in DU145 following treatment, but no change was observed in PC3 (FIG. 40C).

Analysis of membrane integrity and necrosis: Membrane integrity was monitored by confocal analysis in LNCaP, DU145 and PC3 cells. Intact cells stained green due to AO which is membrane permeable, while cells with compromised plasma membranes would stained red due to incorporation of membrane impermeable EtBr into the cytoplasm, and yellow due to co-localization of AO and EtBr in the nuclei. Untreated LNCaP, DU145 and PC3 cells stained positively with AO and emitted green color, but did not stain with EtBr. Following PAX2 knockdown, there were no observable alterations to membrane integrity in LNCaP cells as indicated by positive green fluorescence with AO and absence of red EtBr fluorescence. These finding further indicate that LNCaP cells can be undergoing apoptotic, but not necrotic cell death following PAX2 knockdown. Conversely, PAX2 knockdown in DU145 and PC3 resulted in the accumulation of EtBr in the cytoplasm as indicated by the red staining. In addition, both DU145 and PC3 possessed condensed nuclei which appeared yellow due to the co-localization of green and red staining from AO and EtBr, respectively. These results indicate that DU145 and PC3 are undergoing an alternate cell death pathway involving necrotic cell death compared to LNCaP.

EXAMPLE 12

Oncogenic Role of Engrailed-2 (En-2) in Prostate Cancer Cell Growth and Survival Cell culture: hPrEC cells and DU145, LnCap, and PC3 cell lines were cultured as described in Example 1. siRNA silencing of PAX2 and EN2: Small interfering RNA knock-down was performed as previously described (Gibson et al., Cancer Lett., 248 (2):251-261, 2007). Briefly, a pool of four complementary siRNAs (SEQ ID NOS: 3-10), targeting human PAX2 mRNA (Accession no. NM_003989.1) were synthesized (Dharmacon Research, Lafayette, Colo., USA) to knock down PAX2 expression. To achieve EN2 gene silencing, siRNA sequences (SEQ ID NOS:107, 108, 110, 111, 113, 114) targeting human EN2 mRNA (Accession no. NM_001427.2) were purchased from Ambion (Applied Biosystem, Inc.). In addition, a second pool of four non-specific siRNAs was used as a negative control (Dharmacon, Inc.). siRNA molecules were transfected with Code-Breaker transfection reagent according to the manufacturer's protocol (Promega, Inc.).

RNA isolation and quantitative real-time PCR: RNA was isolated and subjected to two-step QRT-PCR as described in Example 1. The primer pair for human PAX2 (Cat #PPH06881-A, SEQ ID NOS: 33 and 34) and EN2 (Cat. #PPH00975A, forward primer 5'-GTTCGTGGAT-TCAAAGGTGGCT-3' (SEQ ID NO:115), reverse primer 5'-TAAATCCCACACTGGTTCTCCG-3' (SEQ ID NO:116)) were purchased from Super Array Bioscience, Md., USA. GAPDH was amplified as a housekeeping gene to normalize the initial content of total cDNA as previously described (Gibson et al., Cancer Lett., 248 (2):251-261, 2007).

Cell proliferation assay: The rate of cell proliferation was determined by [3H] thymidine ribotide ([3H]TdR) incorporation into DNA. Approximately $2.5-5 \times 10^4$ cells were plated onto 24-well plates in their appropriate media. Cells were incubated for 72 hours in the absence or presence of siRNA at the indicated concentrations. The cells were exposed to 37 kBq/ml [methyl-3H] thymidine in the same medium for 6 hours. The adherent cells were fixed by 5% trichloro-acetic acid and lysed in SDS/NaOH lysis buffer overnight. Radioactivity was measured with a Beckman LS3801 liquid scintillation counter. All assays were run three times in triplicate.

Western blot analysis: Western blot analysis was performed as described in Example 2.

Statistical analysis: Statistical analysis was performed using the Student's t-test for unpaired values. P values were determined by a two-sided calculation, and a P value of less than 0.05 was considered statistically significant. Statistical differences are indicated by asterisks.

Figure 41:
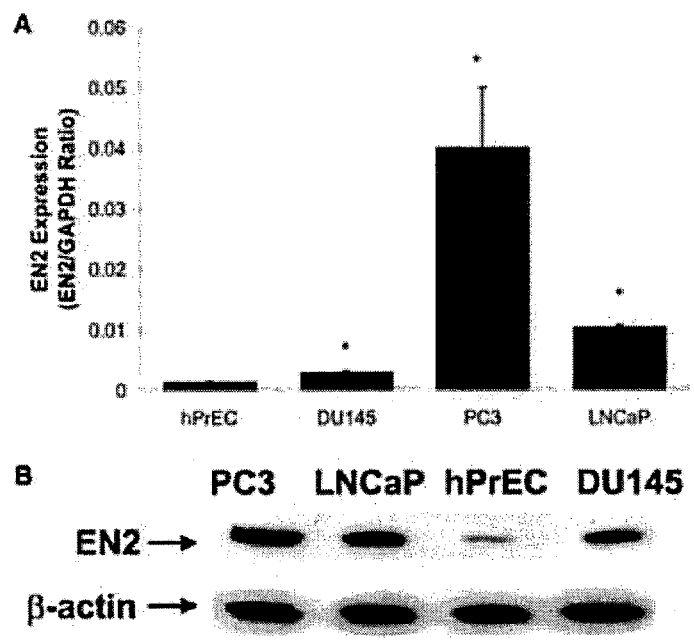
FIG. 41A shows an analysis of Engrailed-2 (EN2) mRNA levels by QRT-PCR in hPrEC prostate primary epithelial cells, DU145, PC3, and LNCaP prostate cancer cells.
FIG. 41B shows a Western blot analysis of EN2 expression in PC3, LNCaP, hPrEC, and DU145 cells.

Analysis of EN2 expression in prostate cancer cells: To investigate EN2 expression, QRT-PCR was performed on prostate cancer cell lines and hPrEC prostate primary culture. As shown in FIG. 41A, EN2 mRNA expression was 2.15-fold higher in DU145 (lane 2), 30-fold higher in PC3 (lane 3) and 7.8-fold higher in LNCaP (lane 4) compared to hPrEC cells (lane 1). Western blot analysis of EN2 protein levels showed low levels of EN2 protein in hPrEC cells (FIG. 41B, lane 3). However, EN2 was over-expressed in all of the prostate cancer cell lines. EN2 expression was lowest in DU145, while PC3 cells showed the greatest level of expression. EN2 expression was 8-fold higher in PC3 (lane 1), 6-fold higher in LNCaP (lane 2) and 4-fold higher in DU145 (lane 4) prostate cancer cells compared to hPrEC cells.

Figure 42:
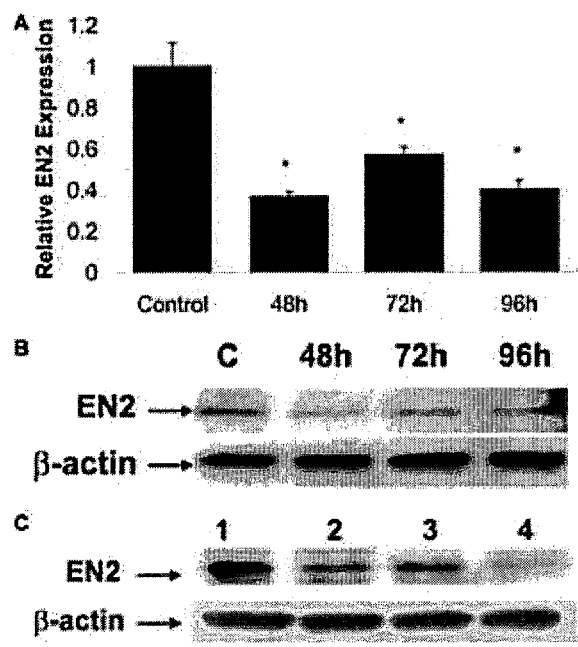
FIG. 42A shows a QRT analysis of silencing of EN2 expression in PC3 and LNCaP cells following EN2 siRNA treatment.
FIG. 42B is a Western blot analysis of silencing of EN2 expression in PC3 following EN2 siRNA treatment.
FIG. 42C is a Western blot analysis of silencing of EN2 expression in LNCaP cells following EN2 siRNA treatment.

Small interfering RNA-mediated suppression of EN2: QRT-PCR analysis of EN2 expression was monitored in PC3 cells following treatment with an EN2 siRNA comprising SEQ ID NO: 107, 108, 110, 111, 113, or 114. This study revealed a 63% decrease after 48 hours, 43% after 72 hours, and 60% after 96 hours of EN2 siRNA treatment in PC3 (FIG. 42A). Western blot analysis was performed to monitor changes in EN2 protein levels after selective targeting and inhibition by EN2 specific siRNA in PC3 prostate cancer cells. Following treatment in PC3 cells, protein expression decreased by 70% at 48 hours, 20% at 72 hours and 26% at 96 hours (FIG. 42B). Efficiency of EN2 knock-down was compared in PC3 (FIG. 42B) and LNCaP cell lines (FIG. 42C). After siRNA treatment for 72 hours, EN2 protein levels decreased by 25% in PC3 (FIG. 42B, lane 2), and by 60% in LNCaP (FIG. 42C, lane 4) when compared to untreated PC3 (FIG. 42B, lane 1) and LNCaP (FIG. 42C, lane 3) cells.

Figure 43:
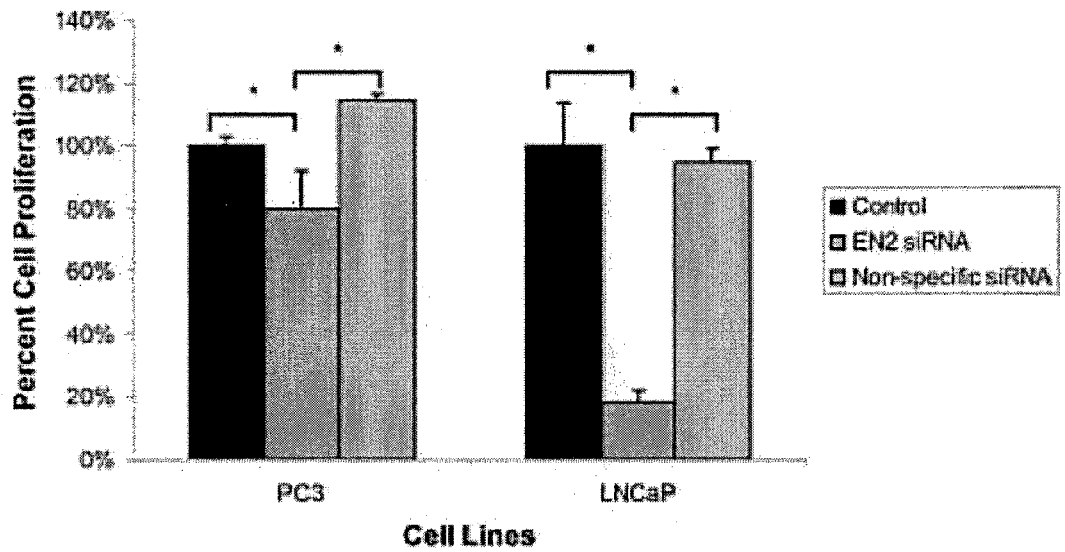
FIG. 43 is a thymidine incorporation analysis of cell proliferation in PC3 and LNCaP cells following EN2 siRNA treatment.

Effect of EN2 knockdown on prostate cancer cell growth: To examine the effect of therapeutic targeting and inhibition of EN2 expression on the rate of prostate cancer cell growth, cell proliferation was monitored by a thymidine incorporation assay after 72 hours of siRNA treatment against EN2 in PC3 and LNCaP cells. Treatment of PC3 cells with 150 nM EN2 siRNA resulted in a 20% inhibition in cell proliferation rate compared to cell treated with media only (FIG. 43). However, treatment of LNCaP cells with EN2 siRNA resulted in an 81% decrease in proliferation rate as compared to those treated with the non-specific siRNA. As a negative control, cells were treated with an equal amount of non-specific siRNA, and there was no significant change in cell viability.

Figure 44:
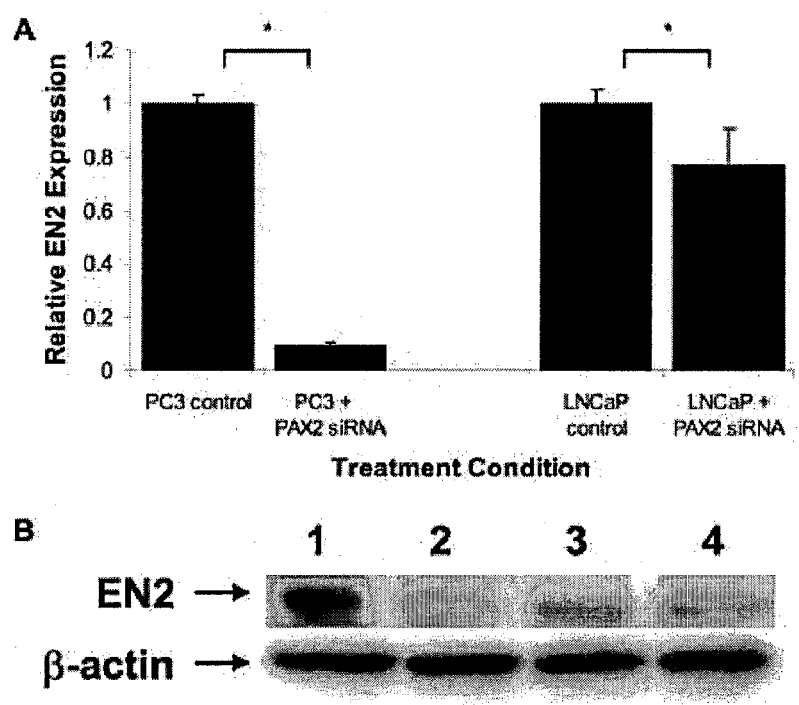
FIG. 44A is a QRT-PCR analysis analysis of EN2 mRNA expression in PC3 and LNCaP cells after PAX2 siRNA treatment.
FIG. 44B is a Western blot analysis of EN2 protein expression in PC3 and LNCaP cells after PAX2 siRNA treatment.

Effect of PAX2 knockdown on EN2 expression in prostate cancer: To determine the role of PAX2 on EN2 expression in prostate cancer, PC3 and LNCaP cells were treated for 3 days with a pool of siRNAS specifically targeted against PAX2. It was previously demonstrated that siRNA knockdown of PAX2 expression occurs as early as 2 days in the prostate cancer cell lines (Gibson et al., Cancer Lett., 248 (2):251-261, 2007). QRT-PCR analysis revealed that EN2 mRNA level was down-regulated in PC3 cell line by 91% as compared to control cells treated with media only (FIG. 44A). In addition, EN2 mRNA in LNCaP cells was suppressed by 23% compared to control. Western blot analysis of EN2 protein expression in the prostate cancer cell lines after 3 days of PAX2 siRNA treatment (FIG. 44B) demonstrated that EN2 expression was decreased 70% in PC3 (lane 2) and 26% in LNCaP (lane 4) prostate cancer cell lines as compared to PC3 (lanes 1) and LNCaP (lanes 3) controls.

Figure 45:
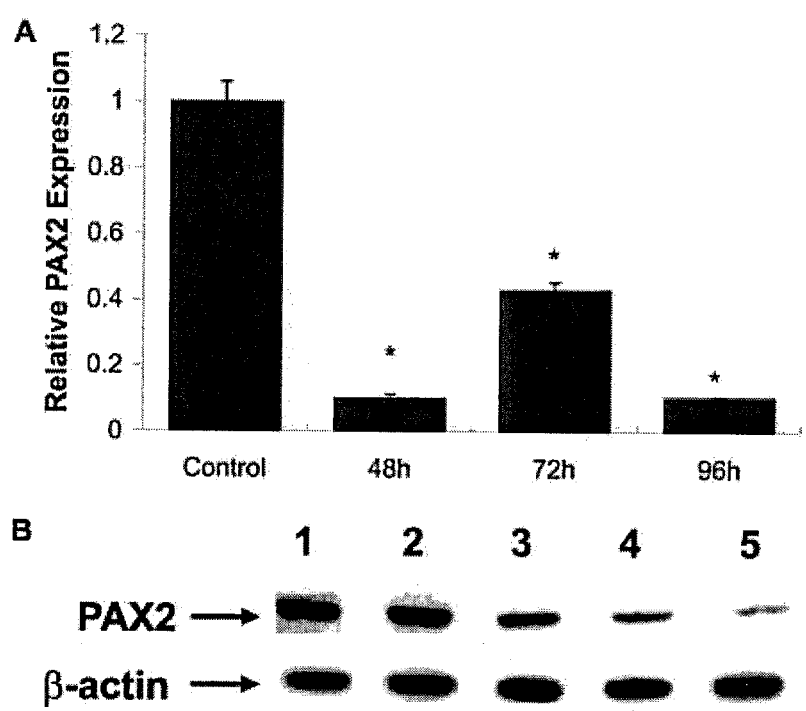
FIG. 45A a QRT-PCR analysisis of PAX2 mRNA expression in LNCaP prostate cancer cells after EN2 siRNA treatment.
FIG. 45B is a Western blot analysis of PAX2 protein expression in LNCaP prostate cancer cells after EN2 siRNA treatment.

Analysis of PAX2 expression after EN2 knockdown in prostate cancer: QRT-PCR analysis of PAX2 was performed in LNCaP cells after treatment with EN2 siRNA to determine whether EN2 can modulate PAX2 expression in prostate cancer. The data shows that PAX2 mRNA level was significantly decreased by 90% at 48 hours, 67% at 72 hours and 90% at 96 hours in LNCaP cells (FIG. 45A). Further, to test the correlation between PAX2 and EN2 at the protein level, Western blot analysis was performed. PAX2 protein levels were decreased by 50% at 48 hours (lane 3), by 66% at 72 hours (lane 4) and by 72% at 96 hours (lane 5) following EN2 siRNA treatment compared to untreated cells (lane 1) and non-specific siRNA treated cells (lane 2) (FIG. 45B).

This example demonstrates that EN2 is over-expressed in human prostate cancer cells as compared to normal prostate epithelial cells. It is plausible that deregulated expression of PAX2 and EN2 may ultimately promote tumor progression specifically via cancer cell proliferation and survival.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for treating a prostate condition in a subject, comprising:
   administering to the subject an effective amount of a pharmaceutical composition comprising:
      a first agent that inhibits Engrailed-2 (EN2) expression and/or EN2 activity, wherein said first agent comprises:
   an siRNA comprising a sequence selected from the group consisting of SEQ ID NOS: 107, 108, 110, 111, 113 and 114 or an expression vector encoding a short hairpin RNA comprising a sequence selected from the group consisting of SEQ ID NOS: 107, 108, 110, 111, 113 and 114; and
      a second agent that enhances DEFB1 gene expression or DEFB1 activity.

2. The method of claim 1, wherein said first agent comprises an siRNA comprising a sequence selected from the group consisting of SEQ ID NOS: 107, 108, 110, 111, 113 and 114.

3. The method of claim 1, wherein said first agent comprises an expression vector encoding a short hairpin RNA comprising a sequence selected from the group consisting of SEQ ID NOS: 107, 108, 110, 111, 113 and 114.

4. The method of claim 1, wherein the second agent comprises DEFB1 protein.

5. The method of claim 1, wherein the second agent comprises an expression vector that expresses DEFB1 protein.

6. The method of claim 1, wherein the second agent comprises a DEFB1 saRNA or an expression vector encoding a DEFB1 saRNA.

7. The method of claim 1, wherein the second agent comprises interferon-γ.

8. The method of claim 1, wherein said pharmaceutical composition further comprises a pharmaceutically acceptable carrier.

9. The method of claim 1, wherein one or both of said first agent and said second agent comprise a targeting moiety capable of binding to the surface of a prostate cell, said targeting moiety is selected from the group consisting of aptamers, peptides, antibody-derived epitope binding domains, cellular ligands, and combination thereof.

10. The method of claim 1, wherein said prostate condition is prostate cancer or prostate intraepithelial neoplasia (PIN).

11. A method for treating prostate cancer or prostatic intraepithelial neoplasia (PIN) in a test subject, comprising:
   (a) determining expression levels of EN2 and DEFB1 in cells or bodily fluids obtained from tissue of the test subject suspected to be at risk for prostate cancer and from cells or bodily fluids from the corresponding cells or bodily fluids of a cancer-free control subject;
   (b) determining EN2-to-DEFB1 expression ratios from said cells or bodily fluids from said cells or bodily fluids from the test subject and from the cancer-free control subject;
   (c) administering to said subject (1) an effective amount of an agent that inhibits EN2 expression and/or EN2 activity; (2) an effective amount of an agent that inhibits PAX2 expression and/or PAX2 activity, and/or (3) an effective amount of an agent that enhances expression and/or DEFB1 activity when the EN2-to-DEFB1 expression ratio is increased in the test subject relative to the control subject.

12. A pharmaceutical composition for treating prostate cancer or PIN, comprising:
   (1) a first agent that inhibits EN2 expression and/or EN2 activity, wherein said first agent comprises:
   an siRNA comprising a sequence selected from the group consisting of SEQ ID NOS: 107, 108, 110, 111, 113 and 114 or an expression vector encoding a short hairpin RNA comprising a sequence selected from the group consisting of SEQ ID. NOS: 107, 108, 110, 111, 113 and 114; and; and
   (2) a second agent that enhances expression and/or DEFB1 activity.

13. The pharmaceutical composition of claim 12, further comprising a pharmaceutically acceptable carrier.

* * * * *

SEQUENCE LISTING

<160> NUMBER OF SEQ ID NOS: 117

<210> SEQ ID NO 1
<211> LENGTH: 5
<212> TYPE: DNA
<213> ORGANISM: Homo sapiens

<400> SEQUENCE: 1 ccttg                                                                    5

<210> SEQ ID NO 2
<211> LENGTH: 5
<212> TYPE: DNA
<213> ORGANISM: Homo sapiens

<400> SEQUENCE: 2 caagg                                                                    5

<210> SEQ ID NO 3
<211> LENGTH: 21
<212> TYPE: RNA
<213> ORGANISM: Homo sapiens

<400> SEQUENCE: 3
auagacucga cuugacuucu u                                                 21

<210> SEQ ID NO 4
<211> LENGTH: 21
<212> TYPE: RNA
<213> ORGANISM: Homo sapiens

<400> SEQUENCE: 4
aucuucauca cguuccucu u                                                  21

<210> SEQ ID NO 5
<211> LENGTH: 21
<212> TYPE: RNA
<213> ORGANISM: Homo sapiens

<400> SEQUENCE: 5
guauucagca aucuuguccu u                                                 21

<210> SEQ ID NO 6
<211> LENGTH: 21
<212> TYPE: RNA
<213> ORGANISM: Homo sapiens

<400> SEQUENCE: 6
gauuugaugu gcucugaugu u                                                 21

<210> SEQ ID NO 7
<211> LENGTH: 21
<212> TYPE: RNA
<213> ORGANISM: Homo sapiens

<400> SEQUENCE: 7
gaagucaagu cgagucuauu u                                                 21

<210> SEQ ID NO 8
<211> LENGTH: 21
<212> TYPE: RNA
<213> ORGANISM: Homo sapiens

```
<400> SEQUENCE: 8
gaggaaacgu gaugaagauu u                                              21

<210> SEQ ID NO 9
<211> LENGTH: 21
<212> TYPE: RNA
<213> ORGANISM: Homo sapiens

<400> SEQUENCE: 9
ggacaagauu gcugaauacu u                                              21

<210> SEQ ID NO 10
<211> LENGTH: 21
<212> TYPE: RNA
<213> ORGANISM: Homo sapiens

<400> SEQUENCE: 10
caucagagca caucaaaucu u                                              21

<210> SEQ ID NO 11
<211> LENGTH: 20
<212> TYPE: DNA
<213> ORGANISM: Homo sapiens

<400> SEQUENCE: 11
acccgactat gttcgcctgg                                                20

<210> SEQ ID NO 12
<211> LENGTH: 21
<212> TYPE: DNA
<213> ORGANISM: Homo sapiens

<400> SEQUENCE: 12
aagctctgga tcgagtcttt g                                              21

<210> SEQ ID NO 13
<211> LENGTH: 20
<212> TYPE: DNA
<213> ORGANISM: Homo sapiens

<400> SEQUENCE: 13
atgtgtcagg cacacagacg                                                20

<210> SEQ ID NO 14
<211> LENGTH: 21
<212> TYPE: RNA
<213> ORGANISM: Homo sapiens

<400> SEQUENCE: 14
gucgagucua ucugcauccu u                                              21

<210> SEQ ID NO 15
<211> LENGTH: 21
<212> TYPE: RNA
<213> ORGANISM: Homo sapiens

<400> SEQUENCE: 15
ggaugcagau agacucgacu u                                              21

<210> SEQ ID NO 16
<211> LENGTH: 19
<212> TYPE: DNA
<213> ORGANISM: Homo sapiens
```

```
<400> SEQUENCE: 16
aagttcaccc ttgactgtg                                              19

<210> SEQ ID NO 17
<211> LENGTH: 75
<212> TYPE: DNA
<213> ORGANISM: Artificial Sequence
<220> FEATURE:
<223> OTHER INFORMATION: Degenerate PAX2 binding site
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (2)..(35)
<223> OTHER INFORMATION: n=a, g, c, or t where positions 2-35 may be
      present or absent
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (42)..(75)
<223> OTHER INFORMATION: n=a, g, c, or t where positions 42-75 may be
      present or absent

<400> SEQUENCE: 17
nnnnnnnnnn nnnnnnnnnn nnnnnnnnnn nnnnnccttg nnnnnnnnnn nnnnnnnnnn   60
nnnnnnnnnn nnnnn                                                    75

<210> SEQ ID NO 18
<211> LENGTH: 20
<212> TYPE: DNA
<213> ORGANISM: Homo sapiens

<400> SEQUENCE: 18
ctcccttcag ttccgtcgac                                               20

<210> SEQ ID NO 19
<211> LENGTH: 20
<212> TYPE: DNA
<213> ORGANISM: Homo sapiens

<400> SEQUENCE: 19
ctcccttcac cttggtcgac                                               20

<210> SEQ ID NO 20
<211> LENGTH: 40
<212> TYPE: DNA
<213> ORGANISM: Homo sapiens

<400> SEQUENCE: 20
actgtggcac ctcccttcag ttccgtcgac gaggttgtgc                         40

<210> SEQ ID NO 21
<211> LENGTH: 40
<212> TYPE: DNA
<213> ORGANISM: Homo sapiens

<400> SEQUENCE: 21
actgtggcac ctcccttcac cttggtcgac gaggttgtgc                         40

<210> SEQ ID NO 22
<211> LENGTH: 5
<212> TYPE: DNA
```

<213> ORGANISM: Homo sapiens

<400> SEQUENCE: 22 ctctg                                                                   5

<210> SEQ ID NO 23
<211> LENGTH: 20
<212> TYPE: DNA
<213> ORGANISM: Homo sapiens

<400> SEQUENCE: 23
ctcccttcac tctggtcgac                                                   20

<210> SEQ ID NO 24
<211> LENGTH: 40
<212> TYPE: DNA
<213> ORGANISM: Homo sapiens

<400> SEQUENCE: 24
actgtggcac ctcccttcac tctggtcgac gaggttgtgc                             40

<210> SEQ ID NO 25
<211> LENGTH: 20
<212> TYPE: DNA
<213> ORGANISM: Homo sapiens

<400> SEQUENCE: 25
agaagttcac ccttgactgt                                                   20

<210> SEQ ID NO 26
<211> LENGTH: 20
<212> TYPE: DNA
<213> ORGANISM: Homo sapiens

<400> SEQUENCE: 26
agaagttcac gttccactgt                                                   20

<210> SEQ ID NO 27
<211> LENGTH: 20
<212> TYPE: DNA
<213> ORGANISM: Homo sapiens

<400> SEQUENCE: 27
agaagttcac gctctactgt                                                   20

<210> SEQ ID NO 28
<211> LENGTH: 39
<212> TYPE: DNA
<213> ORGANISM: Homo sapiens

<400> SEQUENCE: 28
ttagcgatta gaagttcacc cttgactgtg gcacctccc                              39

<210> SEQ ID NO 29
<211> LENGTH: 40
<212> TYPE: DNA
<213> ORGANISM: Homo sapiens

<400> SEQUENCE: 29
gttagcgatt agaagttcac gttccactgt ggcacctccc                             40

<210> SEQ ID NO 30
<211> LENGTH: 40
<212> TYPE: DNA

<213> ORGANISM: Homo sapiens

<400> SEQUENCE: 30
gttagcgatt agaagttcac gctctactgt ggcacctccc     40

<210> SEQ ID NO 31
<211> LENGTH: 20
<212> TYPE: DNA
<213> ORGANISM: Homo sapiens

<400> SEQUENCE: 31
actgcccatt gcccaaacac     20

<210> SEQ ID NO 32
<211> LENGTH: 21
<212> TYPE: DNA
<213> ORGANISM: Homo sapiens

<400> SEQUENCE: 32
aaaatcttgc cagctttccc c     21

<210> SEQ ID NO 33
<211> LENGTH: 23
<212> TYPE: DNA
<213> ORGANISM: Homo sapiens

<400> SEQUENCE: 33
gtcggttacg gagcggaccg gag     23

<210> SEQ ID NO 34
<211> LENGTH: 24
<212> TYPE: DNA
<213> ORGANISM: Homo sapiens

<400> SEQUENCE: 34
taacatatag acaaacgcac accg     24

<210> SEQ ID NO 35
<211> LENGTH: 23
<212> TYPE: DNA
<213> ORGANISM: Homo sapiens

<400> SEQUENCE: 35
gcgcttgtgt cgccattgta ttc     23

<210> SEQ ID NO 36
<211> LENGTH: 24
<212> TYPE: DNA
<213> ORGANISM: Homo sapiens

<400> SEQUENCE: 36
gtcacaccac agaagtaagg ttcc     24

<210> SEQ ID NO 37
<211> LENGTH: 23
<212> TYPE: DNA
<213> ORGANISM: Homo sapiens

<400> SEQUENCE: 37
gtcggttacg gagcggaccg gag     23

<210> SEQ ID NO 38
<211> LENGTH: 25
<212> TYPE: DNA

<213> ORGANISM: Homo sapiens

<400> SEQUENCE: 38
cacagagcat tggcgatctc gatgc                                              25

<210> SEQ ID NO 39
<211> LENGTH: 135
<212> TYPE: PRT
<213> ORGANISM: Homo sapiens

<400> SEQUENCE: 39

Met Asp Met His Cys Lys Ala Asp Pro Phe Ser Ala Met His Arg His
1               5                   10                  15

Gly Gly Val Asn Gln Leu Gly Gly Val Phe Val Asn Gly Arg Pro Leu
            20                  25                  30

Pro Asp Val Val Arg Gln Arg Ile Val Glu Leu Ala His Gln Gly Val
        35                  40                  45

Arg Pro Cys Asp Ile Ser Arg Gln Leu Arg Val Ser His Gly Cys Val
    50                  55                  60

Ser Lys Ile Leu Gly Arg Tyr Tyr Glu Thr Gly Ser Ile Lys Pro Gly
65                  70                  75                  80

Val Ile Gly Gly Ser Lys Pro Lys Val Ala Thr Pro Lys Val Val Asp
                85                  90                  95

Lys Ile Ala Glu Tyr Lys Arg Gln Asn Pro Thr Met Phe Ala Trp Glu
            100                 105                 110

Ile Arg Asp Arg Leu Leu Ala Glu Gly Ile Cys Asp Asn Asp Thr Val
        115                 120                 125

Pro Ser Val Ser Ser Ile Asn
    130                 135

<210> SEQ ID NO 40
<211> LENGTH: 7331
<212> TYPE: DNA
<213> ORGANISM: Homo sapiens
<220> FEATURE:
<221> NAME/KEY: misc_feature
<222> LOCATION: (1)..(7331)
<223> OTHER INFORMATION: n=a, c, g, or t

<400> SEQUENCE: 40
ttcccccttt ccangagggc ctaatccgtt gcgcgcgcgc acgcggacac acacacacac        60
acacacacac acacacacac acacacggcc cccatagcca ccgcaactct cagcagcagn      120
ncctagctcc tctgacccga ggccccaaga cggcgggcac aggaacccct gggacgtcct      180
ggctccaggc tggacgtagg cggaggtggc aggagtggac aaacccaggc gggtcccacg      240 acgcccccttt cctcgggtct ctccttgttt cagccagccg ctctcgcccc tggtcccctc     300
ttccctgcgt tagggtcctt tgtctccagc cacctcgcag cctgtccccg cctcggcggc      360
cctgcccttt gggcctccca gatctctctg gcgggtcccc ctgccttacc agctcccggc      420
tgtggcgcgc tcttcgcctg ctcctcacat ncacacagct gctgggagag gaggaaggaa      480
aggcggncgc gccgcggatg gatccgagac ggtagatttg gtgccggctc gcaaactctg      540
ggaaacttaa ngccggttct tccgcccctc tncaactatg nccagcgcgg cccggtcgcg      600
cgcgctcacc ccgcggggac cctttccttt cctgtatttt cggctgcggc tgtttcgctt      660
cctctggtct cccagccttt ggagtggctt ccctggccct gcactccgtt ccctttcggc      720 cgccccggc tgtcgcctgc ccccacccctc cgcaggtccc acggtcgcgg cggcgatgac      780
tgtggaggta acgccgggga cgtcctgggt cagcctgcac cgtctccctc gaccacagcc      840

```
cgatgaggcc gcgggctccg ggccggctgc taagagagtt aatcattact tcgccagcga    900
cactcagcct cccccttccga ctctctcgcc cggcctaggg gaggagggga ggggacagct    960
ggccaggtgg ggacttcggc ttcgcacaaa ccagcctctt caggcctccc agagacaggt   1020
ggtggcttct cagttccctc ggcaactctc taaggtcctc tttcttcccc tcctgtctct   1080
ccctccttcg agcctcctcc cagccaggcc tctccccacc gtctcctgtc cgctctggct   1140
ttgactgatt aactgcaggt cctgggagaa ccaactttct ttgtttggaa ccggaccgga   1200
cgggatttcc ttccctaggt ctccgccaat gggccagctc ctcccgacgg ttttggcgga   1260
ctggctgaag aggaccgcgc ctgaggccac aattaacccg gctgttggtg gtggtggttg   1320
gggggtgggc agtgaggaat ttaaccgatc tctctagcagc tgcgctggtg cagttgggag   1380
gggggtgcag gaagtgggaa tggaggagtg gcaggaggta tagacagagg gaagaacgat   1440
aaacctggac aggtgtggca tagccaatag aagggggaaac aaaataaaac aggaaggcgg   1500
cgcggggagg aatccccagt aacctttata ggattgaagt tgggtggaaa acgccacctc   1560
ctgccctacc ttagcactca gatccctcct ttacctcttt gtgaaagggt aagagttcag   1620
aaagctggcc atttactcca taatctacta gagaaatgtc tgggtttgca aaatgcctat   1680
tgattagctc catggagtag acaagacagg cgtaattatc cccatttttac aggtgagaaa   1740
actgagtctc aaagaagcaa agggactgtg tatgtagtgg ctgtcacttt ttcctgtagg   1800
ctgtggggtg agtggcccct ttagctgtgc agaggtccat gggtatctag ggaggcggta   1860
caggctgtgt ccaggtctga gccagaagta ccagggcctc acggggctcc tagccctttt   1920
agcttgttct ctgttggaca ggaccttcac tcttactctc tagacctgct ggctgggttt   1980
ctcccagctt cgctattttt tcagttccct agtagagtgg cccatgggcg gtagccacct   2040
ggctggcccg tgccactaag aggcagcttt ggtggccaag tggcttgcat tgttgttgct   2100
cctcaaaggg cctgtgaagg gctgggcagg tcgcaaagac ctcttgtgag gggaaagcta   2160
gattaaaggg ggtaaggatc ctggaggata aaggccaagc acgtgcgcct ggactccaca   2220
ggaccaacag accgagcggg cggggccngc tgggagtcag gccccccggg cttcacgcag   2280
ggagcccaaa tattgggaac aaaagcagga aaagaagagt gagagcagga gggagggagg   2340
gagcgaggaa gcagaaatta gggggtctta gatgaaaaaa aaagaaagt agctttaggg   2400
ggaatgtgct gtggagtgtg aaattgcagc ccatggtgct ccatattgta ccagaagctc   2460
ttccaaaaaa aaaaaaaaaa accatcctcc aacgtgacca gagggccagg caggggggaag   2520
ggcggggaga gaatggggag gaggaggggg aaaggccggg caggagccgg tcaggccttt   2580
ctgcggaagg ggctggggtg taagtttcgg ctccctggga tctgacagcc gagggtatgc   2640
gccctgggt gcgccgggac ccagagggcg agtgagcctc ggttggtcgg ctctggagtt   2700
cggttgtcag aagaactttt attttttcttt ttggtggtga cttctaaaag tgggaataat   2760
ccagaaatga agctcagctg cggagctgca gctctgttct ccctctctcc cctgcctttc   2820
tgcttctctt cccttcggac tactttttctc cccttggttc taaatagctt tttcccctct   2880
gaactttaat gcatttaatt tggtccgcgc tgtggggagc atttcctggg gagatgcatt   2940
taatttcgga atttctaatc ccctcccctca gaccccggtc ctagctcccc tagccgctcc   3000
ccgggaagtg gaaggaggaa ggcaggtccc ggccacgggg gaggggcgcg gctgggatgc   3060
tcccgcggcc ccctccgtct caccaaggct cagccgcctt cccaagctac tggaggccgg   3120
gcgcctgggc cccgggtcag ggcctgcan gaagaagaga ggcaacccccc gctttctgcc   3180
ttttcttcgc ctgggcaaga aaacgctggg ccagggaact ggaaaccgga aaacaggaga   3240
```

```
aagggttttnt ggaaggcanc gggagcgggt ggcagncggg gcancgggca ntggactagg    3300
tctacaccgg cacttcactt ttgcacaaca tgcccagaaa cgcatttgag agccctggag    3360
tcgcgcttgg cttggcttgg ggcgccggtg cgtgggtaca ctcgaggtcg gggtgcctat    3420
ccgccacccc gacacctaca cccagtgcag agcaggcgcg gcccagccag acaaccaggc    3480
cggcagtagc tcggcctgga gggcggaggc aaggttgggg gccgccaggc gcctgggcaa    3540
gcctggcagg gaagggagcc gagaaggcaa aggagccgag atccacaagg aagattnntt    3600
gggcagatca gatgcacaga ggcggctaat gaagcaaatc ccgagatggg tttcagagca    3660
actccccaaa agtttatttt gcctttaaat ttccgcaggg aggcgggctc cttgtttgaa    3720
gtgtaaatgc ccctaggttg gggggtggaa gggccgcttt gaaaacacca gagagaaaag    3780
gttcatttag aggcggacgg gaaaagcaac caaccctgac aggtcggagc ccgggtagtg    3840 tttgggggttg ggtngttttc tttctttctc tttcttttcc cctttcctct tctttcttcc    3900
cttttgtgnn ttttnnttgt ttttttttntn ttnttttttnt ttaantggct ttcttgcttc    3960
cccccacccc tctactagac tctatagaag aaagagaaca gaaaaggggg agtcagagga    4020
gcggccagtg actggatgaa ggccagccct tcatcctgga gccccaggag aaggcagagc    4080
tttggagaaa aggggttcct aatctccagg gagcattact ctttgactct ctagacccag    4140
gaatgggctg gacgctaatg gggaagcggc caggaacccg gcctggcgga agagtgagtg    4200
tccagctagt gcagtgctgg gaagacgatc ccaggagcag gggggactct caggggctac    4260
ctgggaatgg gactatcaga agggtcttta ctcctcanaa ggtgcatgtg aaggacaggt    4320
gtgtgaggac aacttccagc acacttggcg cattaagtcc ccttctctac aaaatggaaa    4380
atccttctcg cccaacatgt gaaaatgctt gttgtgggca cccacatttc atggtacttg    4440
taacatagga catgtctagc tggttctaga aaaatctgtg tctgtgtgga agggggggg    4500 tttactcaca gctttcttcc ttcaatagtt cacacacccc gagacaaatt cctggatgac    4560
caacttggag agacctgggg caaaggttac tttagttctg agctcctcta aataaggacc    4620 cttttctcaac gttcctttca ccccagttct gggttaatta cttccagtta gtgcgtgttc    4680
gtggggttgt gaggccaaag caaacccggg agcgccatct gcaggcctca agaggaagag    4740
actgacctta gaggctaggc cctgcgtctt caacctctag cccaagggaa ccaacctgcc    4800
tagccaccca agggaagtgg gataggggct gggaggggca ggcggtgagg agtgttttcc    4860
tcccagactt taccccgcag gtggattaag cttattgggc tctggaggat acaggaggga    4920
gggcaaatgc caggatccca gcggacccag gccccacagg agtgagaggc tcagaacctc    4980
gtcccgctga gcctggcctg agctcctcct gaggaataag ggcatcccaa aaacccgggt    5040
acaagacgcc cagtagtagt agttaggctg agtcaggcag gtgcatctct ccccatggta    5100
tctgccgccc aggctccggc cagagggagg ggagcgcgag tccgcggcgc ttccgcgggg    5160
cgcccggaac tgcagacggg ggctggagga atctcggatt cgggctgcaa gagcgctgcg    5220
caagcttcgc cgagccgccc tttcgcagac ccagggaagc gggggggagg agcgaaggag    5280
ggagagagag ttaaaacatc agcttgaaag tgcccaagat gatttttatta agaccgaggg    5340 gaaaattatt ttcatgaaag attctccccg gaatatttct tgtacttaac ccagttagga    5400
agacaaaggg cttcttctg cctggtgcgg tgcgagcgga ccccagcgag caaggagct    5460 agtgccaaag agaactgcgg aggctccggc aggagtgggg acgtcccgt ggttgcgcct    5520 cctgcgctcg ccccggatcc accgagctag cagcgggcgg cgctcagccg cgtccgcagc    5580
ctcctcttct ccccagccgg ggagagccag cctcgtctcc cacatcctct gccgccagcg    5640
```

```
acctgcagct ccgcactgtt tccctcccct gtaccccctt cccagtcacc cgagggttca    5700
gaaaccaagt cccccggctc tcccgccatc cgctgggtcc caccgaggca ggtgggtact    5760
cgccggaggt cttcagctcg attctgaacc aagcgttctg gactgcccag acccggtggg    5820
caaggggact ggggaggccc tgcgcacagt cgcgtggaac gggaggggac aagacaaact    5880
gctggacact tttccgtgga atgagaagtg ggggtgcgt gggtgggaag gtacctccgg     5940
agggaaaggc caagggaag gaccagaaag agaggaagga agagccggga aggaacggaa     6000
gggaactcag agccgaggt ggtgggttg gggctaggga tgcgcactgg gcccggggcc      6060
gcgcggccca ggcgggcact ggccagtgga tggcagggct gggcgagtta gaactgagag    6120
cccggcttca cagcgcagcg cgctccgagg ccctctgtcg ttacctgaat attcattaga    6180
ctgaccgctc tttatcctta tctaacgttt atcttatcgg cgagtttcgt ttctcagtgt    6240
agttttaatc ccgggctccc attcccctc ccccggtccg ctcccctccc tcctcttcc     6300 ttcgccggct gctccctccc tccctccctc ccatttctcc ctcccctgcc ctcccctgc    6360 cggcaccgga gtgacaggct cggggccctc ctcgccgaag ctcggggctc cagcgctggc    6420
gaatcacaga gtggtggaat ctattgcctt tgtctgacaa gtcatccatc tcccggcgcg    6480
gggaggggga ggaggtctgg agggggcttt gcagctttta gagagacaca caccgggagc    6540
cgaggctcca gtctccggcc gagtcttcta gcagccgcaa cccacctggg gccagcccag    6600
agctgccagc gccgctcggc tccctccctc cctccggcc cttcggccgc ggcggcgtgc     6660
gcctgccttt tccgggggcg gggcctggc ccgcgcgctc ccctcccgca ggcgccacct    6720
cggacatccc cgggattgct acttctctgc caacttcgcc aactcgccag cacttggaga    6780
ggcccggctc ccctcccggc gccctctgac cgccccgcc ccgcgcgctc tccgaccacc     6840
gcctctcgga tgaacaggtt ccaggggagc tgagcgagtc gcctcccccg cccagcttca    6900
gccctggctg cagctgcagc gcgagccatg cgccccagt gcaccccggc ccggcccacc     6960
gccccggggc cattctgctg accgcccagc cccgagcccc gacagtggca agttgcggct    7020
actgcggttg caagctccgg ccaacccgga ggagccccag cggggagcgc agtgttgcgc    7080
cccccgcccc cgcgcgcgcc gcagcagccg ggcgttcact catcctcct ccccaccgt      7140 ccctcccttt tctcctcaag tcctgaagtt gagtttgaga ggcgacacgg cggcggcggc    7200
cgcgctgctc ccgctcctct gcctccccat ggatatgcac tgcaaagcag accccttctc    7260
cgcgatgcac cgtgagtacc cgcgcccggc tcctgtcccg gctcgggctc tccgtcccaa    7320
ccctgtccag t                                                        7331
```

<210> SEQ ID NO 41
<211> LENGTH: 416
<212> TYPE: PRT
<213> ORGANISM: Homo sapiens

<400> SEQUENCE: 41

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
        50                  55                  60

Val Ser Lys Ile Leu Gly Arg Tyr Tyr Glu Thr Gly Ser Ile Lys Pro

```
             65                  70                  75                  80
Gly Val Ile Gly Gly Ser Lys Pro Lys Val Ala Thr Pro Lys Val Val
                         85                  90                  95

Asp Lys Ile Ala Glu Tyr Lys Arg Gln Asn Pro Thr Met Phe Ala Trp
                100                 105                 110

Glu Ile Arg Asp Arg Leu Leu Ala Glu Gly Ile Cys Asp Asn Asp Thr
            115                 120                 125

Val Pro Ser Val Ser Ser Ile Asn Arg Ile Ile Arg Thr Lys Val Gln
        130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Val Glu Val
        195                 200                 205

Tyr Thr Asp Pro Ala His Ile Arg Gly Gly Gly Leu His Leu Val
    210                 215                 220

Trp Thr Leu Arg Asp Val Ser Glu Gly Ser Val Pro Asn Gly Asp Ser
225                 230                 235                 240

Gln Ser Gly Val Asp Ser Leu Arg Lys His Leu Arg Ala Asp Thr Phe
                245                 250                 255

Thr Gln Gln Gln Leu Glu Ala Leu Asp Arg Val Phe Glu Arg Pro Ser
            260                 265                 270

Tyr Pro Asp Val Phe Gln Ala Ser Glu His Ile Lys Ser Glu Gln Gly
        275                 280                 285

Asn Glu Tyr Ser Leu Pro Ala Leu Thr Pro Gly Leu Asp Glu Val Lys
    290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
                325                 330                 335

Thr Leu Pro Gly Tyr Pro Pro His Val Pro Pro Thr Gly Gln Gly Ser
            340                 345                 350

Tyr Pro Thr Ser Thr Leu Ala Gly Met Val Pro Gly Ser Glu Phe Ser
        355                 360                 365

Gly Asn Pro Tyr Ser His Pro Gln Tyr Thr Ala Tyr Asn Glu Ala Trp
    370                 375                 380

Arg Phe Ser Asn Pro Ala Leu Leu Ser Ser Pro Tyr Tyr Tyr Ser Ala
385                 390                 395                 400

Ala Pro Arg Ser Ala Pro Ala Ala Ala Ala Ala Tyr Asp Arg His
                405                 410                 415
```

<210> SEQ ID NO 42
<211> LENGTH: 4276
<212> TYPE: DNA
<213> ORGANISM: Homo sapiens

<400> SEQUENCE: 42

```
aggctccagt ctccggccga gtcttctcgc agccgcaacc cacctggggc cagcccagag      60
ctgccagcgc cgctcggctc cctccctccc tcccggccct tcggccgcgg cggcgtgcgc     120 ctgcctttc  cggggcgggg ggcctggccc gcgcgctccc ctcccgcagg cgccacctcg     180
gacatccccg ggattgctac ttctctgcca acttcgccaa ctcgccagca cttggagagg     240
```

```
cccggctccc ctcccggcgc cctctgaccg ccccogccce gcgcgctctc cgaccaccgc   300
ctctcggatg accaggttcc aggggagctg agcgagtcgc ctcccccgcc cagcttcagc   360
cctggctgca gctgcagcgc gagccatgcg cccccagtgc accccggccc ggcccaccgc   420
cccggggcca ttctgctgac cgcccagccc cgagccccga cagtggcaag ttgcggctac   480
tgcagttgca agctccggcc aacccggagg agccccagcg gggagcgcag tgttgcgccc   540
cccgcccccg cgcgccccgc agcagccggg cgttcactca tcctcccctcc cccaccgtcc   600 ctcccttttc tcctcaagtc ctgaagttga gtttgagagg cgacacgcg gcggcggccg    660 cgctgctccc gctcctctgc ctccccatgg atatgcactg caaagcagac cccttctccg   720
cgatgcaccc agggcacggg ggtgtgaacc agctcggggg ggtgtttgtg aacggccggc   780
ccctacccga cgtggtgagg cagcgcatcg tggagctggc ccaccagggt gtgcggccct   840
gtgacatctc ccggcagctg cgggtcagcc acggctgtgt cagcaaaatc ctgggcaggt   900
actacgagac cggcagcatc aagccgggtg tgatcggtgg ctccaagccc aaagtggcga   960
cgcccaaagt ggtggacaag attgctgaat acaaacgaca gaacccgact atgttcgcct  1020
gggagattcg agaccggctc ctggccgagg gcatctgtga caatgacaca gtgcccagcg  1080
tctcttccat caacagaatc atccggacca aagttcagca gcctttccac ccaacgccgg  1140
atggggctgg acaggagtg accgcccctg gccacaccat tgttcccagc acggcctccc  1200
ctcctgtttc cagcgcctcc aatgacccag tgggatccta ctccatcaat gggatcctgg  1260
ggattcctcg ctccaatggt gagaagagga acgtgatga agttgaggta tacactgatc  1320
ctgcccacat tagaggaggt ggaggtttgc atctggtctg gactttaaga gatgtgtctg  1380
agggctcagt ccccaatgga gattcccaga gtggtgtgga cagtttgcgg aagcacttgc  1440
gagctgacac cttcacccag cagcagctgg aagctttgga tcgggtcttt gagcgtcctt  1500
cctaccctga cgtcttccag gcatcagagc acatcaaatc agaacagggg aacgagtact  1560
ccctcccagc cctgacccct gggcttgatg aagtcaagtc gagtctatct gcatccacca  1620
accctgagct gggcagcaac gtgtcaggca cacagacata cccagttgtg actggtcgtg  1680
acatggcgag caccactctg cctggttacc ccctcacgt gccccccact ggccagggaa  1740
gctaccccac ctcacccctg gcaggaatgg tgcctgggag cgagttctcc ggcaacccgt  1800
acagccaccc ccagtacacg gcctacaacg aggcttggag attcagcaac cccgccttac  1860
taagttcccc ttattattat agtgccgccc cccggtccgc cctgccgct gctgccgctg  1920 cctatgaccg ccactagtta ccgcggggac cacatcaagc ttcaggccga cagcttcggc  1980
ctccacatcg tccccgtctg acccoccaccc ggagggaggg aggaccgacg cgacgcgatg  2040
cctcccggcc accgcccag cctcaccccca tcccacgacc cccgcaaccc ttcacatcac  2100 cccoctcgaa ggtcggacag gacgggtgga gccgtgggcg ggaccctcag gcccgggccc  2160
gccgccccca gccccgcctg ccgccccctcc ccgcctgcct ggactgcgcg cgccgtgag   2220 ggggattcgg cccagctcgt cccggcctcc accaagccag ccccgaagcc cgccagccac  2280
cctgccggac tcgggcgcga cctgctggcg cgcgccggat gtttctgtga cacacaatca  2340
gcgcggaccg cagcgcggcc cagccccggg caccgcctc ggacgctcgg gcgcaggag   2400 gcttcgctgg aggggctggg ccaaggagat taagaagaaa acgactttct gcaggaggaa  2460
gagcccgctg ccgaatccct gggaaaaatt cttttccccc agtgccagcc ggactgccct  2520
cgccttccgg gtgtgccctg tcccagaaga tggaatgggg gtgtggggt ccggctctag   2580 gaacgggctt tgggggcgtc aggtcttttcc aaggttggga cccaaggatc gggggggccca  2640
```

-continued

```
gcagcccgca ccgatcgagc cggactctcg gctcttcact gctcctcctg gcctgcctag    2700
ttccccaggg cccggcacct cctgctgcga gacccggctc tcagccctgc cttgcccta     2760 cctcagcgtc tcttccacct gctggcctcc cagtttcccc tcctgccagt ccttcgcctg    2820
tcccttgacg ccctgcatcc tcctccctga ctcgcagccc atcggacgc tctcccggga     2880 ccgccgcagg accagtttcc atagactgcg gactggggtc ttcctccagc agttacttga    2940 tgcccccctcc cccgacacag actctcaatc tgccggtggt aagaaccggt tctgagctgg   3000
cgtctgagct gctgcggggt ggaagtgggg ggctgcccac tccactcctc ccatcccctc    3060
ccagcctcct cctccggcag gaactgaaca gaaccacaaa aagtctacat ttatttaata    3120
tgatggtctt tgcaaaaagg aacaaaacaa cacaaaagcc caccaggctg ctgctttgtg    3180
gaaagacggt gtgtgtcgtg tgaaggcgaa acccggtgta cataacccct cccctccgc     3240 cccgccccgc ccggccccgt agagtccctg tcgcccgccg gccctgcctg tagatacgcc    3300
ccgctgtctg tgctgtgaga gtcgccgctc gctggggggg aagggggga cacagctaca    3360 cgcccattaa agcacagcac gtcctggggg aggggggcat tttttatgtt acaaaaaaaa    3420
attacgaaag aaaagaaatc tctatgcaaa atgacgaaca tggtcctgtg gactcctctg    3480
gcctgttttg ttggctcttt ctctgtaatt ccgtgttttc gcttttcct ccctgcccct     3540 ctctcccctct gcccctctct cctctccgct tctctccccc tctgtctctg tctctctccg    3600
tctctgtcgc tcttgtctgt ctgtctctgc tctttcctcg gcctctctcc ccagacctgg    3660
cccggccgcc ctgtctccgc aggctagatc cgaggtggca gctccagccc ccgggctcgc    3720
cccctcgcgg gcgtgccccg cgcgccccgg gcggccgaag gccgggccgc ccgtcccgc     3780 cccgtagttg ctctttcggt agtggcgatg cgccctgcat gtctcctcac ccgtggatcg    3840
tgacgactcg aaataacaga acaaagtca ataaagtgaa atataataaa aatccttgaa     3900
caaatccgaa aaggcttgga gtcctcgccc agatctctct cccctgcgag cccttttttat   3960 ttgagaagga aaaagagaaa agagaatcgt ttaagggaac ccggcgccca gccaggctcc    4020
agtggcccga acggggcggc gagggcggcg agggcgccga ggtccggccc atcccagtcc    4080
tgtggggctg gccgggcaga gaccccggac ccaggcccag gcctaacctg ctaaatgtcc    4140
ccggacggtt ctggtctcct cggccacttt cagtgcgtcg gttcgttttg attcttttc     4200 ttttgtgcac ataagaaata aataataata ataaataaag aataaaattt tgtatgtcaa    4260
aaaaaaaaaa aaaaaa                                                    4276
```

<210> SEQ ID NO 43
<211> LENGTH: 393
<212> TYPE: PRT
<213> ORGANISM: Homo sapiens

<400> SEQUENCE: 43

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                    85                  90                  95

Asp Lys Ile Ala Glu Tyr Lys Arg Gln Asn Pro Thr Met Phe Ala Trp
                100                 105                 110

Glu Ile Arg Asp Arg Leu Leu Ala Glu Gly Ile Cys Asp Asn Asp Thr
            115                 120                 125

Val Pro Ser Val Ser Ser Ile Asn Arg Ile Ile Arg Thr Lys Val Gln
        130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
            195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
        355                 360                 365

Leu Ser Ser Pro Tyr Tyr Tyr Ser Ala Ala Pro Arg Ser Ala Pro Ala
370                 375                 380

Ala Ala Ala Ala Ala Tyr Asp Arg His
385                 390

<210> SEQ ID NO 44
<211> LENGTH: 4207
<212> TYPE: DNA
<213> ORGANISM: Homo sapiens

<400> SEQUENCE: 44
aggctccagt ctccggccga gtcttctcgc agccgcaacc cacctggggc cagcccagag    60
ctgccagcgc cgctcggctc cctccctccc tcccggccct tcggccgcgg cggcgtgcgc   120
ctgccttttc cggggcgggg ggcctggccc gcgcgctccc ctcccgcagg cgccacctcg   180
gacatccccg ggattgctac ttctctgcca acttcgccaa ctcgccagca cttggagagg   240
cccggctccc ctcccggcgc cctctgaccg ccccgcccc gcgcgctctc cgaccaccgc   300
ctctcggatg accaggttcc aggggagctg agcgagtcgc ctccccgcc cagcttcagc   360

-continued

```
cctggctgca gctgcagcgc gagccatgcg cccccagtgc accccggccc ggcccaccgc    420
cccggggcca ttctgctgac cgcccagccc cgagccccga cagtggcaag ttgcggctac    480
tgcagttgca agctccggcc aacccggagg agcccagcg gggagcgcag tgttgcgccc    540
cccgccccg cgcgccccgc agcagccggg cgttcactca tcctccctcc ccaccgtcc     600
ctcccttttc tcctcaagtc ctgaagttga gtttgagagg cgacacggcg gcggcggccg    660
cgctgctccc gctcctctgc ctccccatgg atatgcactg caaagcagac cccttctccg    720
cgatgcaccc agggcacggg ggtgtgaacc agctcggggg ggtgtttgtg aacggccggc    780
ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg gcatctgtga caatgacaca gtgcccagcg   1080
tctcttccat caacagaatc atccggacca aagttcagca gcctttccac ccaacgccgg   1140
atggggctgg gacaggagtg accgcccctg gccacaccat tgttcccagc acggcctccc   1200
ctcctgtttc cagcgcctcc aatgacccag tgggatccta ctccatcaat gggatcctgg   1260
ggattcctcg ctccaatggt gagaagagga acgtgatga agatgtgtct gagggctcag   1320
tccccaatgg agattcccag agtggtgtgg acagtttgcg gaagcacttg cgagctgaca   1380
ccttcaccca gcagcagctg gaagctttgg atcgggtctt tgagcgtcct tcctaccctg   1440
acgtcttcca ggcatcagag cacatcaaat cagaacaggg gaacgagtac tccctcccag   1500
ccctgacccc tgggcttgat gaagtcaagt cgagtctatc tgcatccacc aaccctgagc   1560
tgggcagcaa cgtgtcaggc acacagacat acccagttgt gactggtcgt gacatggcga   1620
gcaccactct gcctggttac cccccctcacg tgccccccac tggccaggga agctacccca   1680
cctccaccct ggcaggaatg gtgcctggga gcgagttctc cggcaacccg tacagccacc   1740
cccagtacac ggcctacaac gaggcttgga gattcagcaa ccccgcctta ctaagttccc   1800
cttattatta tagtgccgcc ccccggtccg ccctgccgc tgctgccgct gcctatgacc    1860
gccactagtt accgcgggga ccacatcaag cttcaggccg acagcttcgg cctccacatc   1920
gtccccgtct gaccccaccc cggagggagg gaggaccgac gcgacgcgat gcctcccggc   1980
caccgcccca gcctcacccc atcccacgac ccccgcaacc cttcacatca ccccccctcga  2040
aggtcggaca ggacgggtgg agccgtgggc gggaccctca ggcccgggcc cgccgccccc   2100
agccccgcct gccgcccctc cccgcctgcc tggactgcgc ggcgccgtga gggggattcg   2160
gcccagctcg tccggcctc caccaagcca gccccgaagc ccgccagcca ccctgccgga   2220
ctcgggcgcg acctgctggc gcgcgccgga tgtttctgtg acacacaatc agcgcggacc   2280
gcagcgcggc ccagccccgg gcacccgcct cggacgctcg ggcgcagga ggcttcgctg    2340
gagggggctgg gccaaggaga ttaagaagaa aacgactttc tgcaggagga agagcccgct   2400
gccgaatccc tggaaaaaat tcttttcccc cagtgccagc cggactgccc tcgccttccg   2460
ggtgtgccct gtcccagaag atggaatggg ggtgtggggg tccggctcta ggaacgggct   2520
ttgggggcgt caggtctttc caaggttggg acccaaggat cgggggggccc agcagcccgc   2580
accgatcgag ccggactctc ggctcttcac tgctcctcct ggcctgccta gttccccagg   2640
gcccggcacc tcctgctgcg agacccggct ctcagccctg ccttgcccct acctcagcgt   2700
ctcttccacc tgctggcctc ccagtttccc ctcctgccag tccttcgcct gtcccttgac   2760
```

```
gccctgcatc ctcctccctg actcgcagcc ccatcggacg ctctcccggg accgccgcag    2820
gaccagtttc catagactgc ggactggggt cttcctccag cagttacttg atgcccctc     2880 ccccgacaca gactctcaat ctgccggtgg taagaaccgg ttctgagctg cgtctgagc     2940 tgctgcgggg tggaagtggg gggctgccca ctccactcct cccatcccct ccagcctcc     3000 tcctccggca ggaactgaac agaaccacaa aaagtctaca tttatttaat atgatggtct    3060
ttgcaaaaag gaacaaaaca acacaaaagc ccaccaggct gctgctttgt ggaaagacgg    3120
tgtgtgtcgt gtgaaggcga aacccggtgt acataacccc tcccctccg ccccgccccg    3180 cccggccccg tagagtccct gtcgcccgcc ggccctgcct gtagatacgc cccgctgtct    3240
gtgctgtgag agtcgccgct cgctgggggg aaggggggg acacagctac acgcccatta     3300
aagcacagca cgtcctgggg gagggggca tttttatgt tacaaaaaaa aattacgaaa      3360
gaaaagaaat ctctatgcaa aatgacgaac atggtcctgt ggactcctct ggcctgtttt    3420
gttggctctt tctctgtaat tccgtgtttt cgcttttcc tccctgcccc tctctccctc     3480
tgcccctctc tcctctccgc ttctctcccc ctctgtctct gtctctctcc gtctctgtcg    3540
ctcttgtctg tctgtctctg ctctttcctc ggcctctctc cccagacctg gcccggccgc    3600
cctgtctccg caggctagat ccgaggtggc agctccagcc cccgggctcg cccctcgcg    3660 ggcgtgcccc gcgcgccccg ggcggccgaa ggccgggccg ccccgtcccg ccccgtagtt    3720
gctctttcgg tagtggcgat gcgccctgca tgtctcctca cccgtggatc gtgacgactc    3780 gaataacag aaacaaagtc aataaagtga aaataaataa aaatccttga acaaatccga     3840
aaaggcttgg agtcctcgcc cagatctctc tcccctgcga gccttttta tttgagaagg     3900 aaaaagagaa aagagaatcg tttaaggaa cccggcgccc agccaggctc cagtggcccg     3960 aacgggcgg cgagggcggc gagggcgccg aggtccggcc catcccagtc ctgtggggct     4020
ggccgggcag agaccccgga cccaggccca ggcctaacct gctaaatgtc cccgacggt     4080 tctggtctcc tcggccactt tcagtgcgtc ggttcgtttt gattcttttt cttttgtgca    4140
cataagaaat aaataataat aataaataaa gaataaaatt ttgtatgtca aaaaaaaaa    4200 aaaaaaa                                                             4207

<210> SEQ ID NO 45
<211> LENGTH: 396
<212> TYPE: PRT
<213> ORGANISM: Homo sapiens

<400> SEQUENCE: 45

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
```

```
                115                 120                 125
Val Pro Ser Val Ser Ile Asn Arg Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
                195                 200                 205

Glu Gly Ser Val Pro Asn Gly Asp Ser Gln Ser Gly Val Asp Ser Leu
            210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Glu Ala Ala Val Gly Pro Ser Ser Ser Leu Met Ser
            340                 345                 350

Lys Pro Gly Arg Lys Leu Ala Glu Val Pro Pro Cys Val Gln Pro Thr
        355                 360                 365

Gly Ala Ser Ser Pro Ala Thr Arg Thr Ala Thr Pro Ser Thr Arg Pro
370                 375                 380

Thr Thr Arg Leu Gly Asp Ser Ala Thr Pro Pro Tyr
385                 390                 395

<210> SEQ ID NO 46
<211> LENGTH: 4290
<212> TYPE: DNA
<213> ORGANISM: Homo sapiens

<400> SEQUENCE: 46
aggctccagt ctccggccga gtcttctcgc agccgcaacc cacctggggc cagcccagag      60
ctgccagcgc cgctcggctc cctccctccc tcccggccct tcggccgcgg cggcgtgcgc     120
ctgccttttc cggggcggg ggcctggccc gcgcgctccc ctcccgcagg cgccacctcg     180
gacatccccg ggattgctac ttctctgcca acttcgccaa ctcgccagca cttggagagg    240
cccggctccc ctcccggcgc cctctgaccg ccccgcccc gcgcgctctc cgaccaccgc     300
ctctcggatg accaggttcc aggggagctg agcgagtcgc ctccccgcc cagcttcagc     360 cctggctgca gctgcagcgc gagccatgcg ccccagtgc accccggccc ggcccaccgc    420
cccggggcca ttctgctgac cgcccagccc cgagccccga cagtggcaag ttgcggctac   480
tgcagttgca agctccggcc aaccggagg agccccagcg ggagcgcag tgttgcgccc    540 cccgccccg cgcgccccgc agcagccggg cgttcactca tcctcccctcc cccaccgtcc   600
```

```
ctcccttttc tcctcaagtc ctgaagttga gtttgagagg cgacacggcg gcggcggccg    660
cgctgctccc gctcctctgc ctccccatgg atatgcactg caaagcagac cccttctccg    720
cgatgcaccc agggcacggg ggtgtgaacc agctcggggg ggtgtttgtg aacggccggc    780
ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg gcatctgtga caatgacaca gtgcccagcg   1080
tctcttccat caacagaatc atccggacca aagttcagca gcctttccac ccaacgccgg   1140
atggggctgg acaggagtg accgcccctg gccacaccat tgttcccagc acggcctccc   1200
ctcctgtttc cagcgcctcc aatgacccag tgggatccta ctccatcaat gggatcctgg   1260
ggattcctcg ctccaatggt gagaagagga acgtgatga agatgtgtct gagggctcag   1320
tccccaatgg agattcccag agtggtgtgg acagtttgcg gaagcacttg cgagctgaca   1380
ccttcaccca gcagcagctg gaagctttgg atcgggtctt tgagcgtcct tcctaccctg   1440
acgtcttcca ggcatcagag cacatcaaat cagaacaggg gaacgagtac tccctcccag   1500
ccctgacccc tgggcttgat gaagtcaagt cgagtctatc tgcatccacc aaccctgagc   1560
tgggcagcaa cgtgtcaggc acacagacat acccagttgt gactggtcgt gacatggcga   1620
gcaccactct gcctggttac ccccctcacg tgcccccac tggccaggga agctaccca   1680 cctccaccct ggcaggaatg gtgcctgagg ctgcagttgg tccctcatcc tccctcatga   1740
gcaagccggg gaggaagctt gcagaagtgc ccccttgtgt gcaacccact ggagcgagtt   1800
ctccggcaac ccgtacagcc accccagta cacggcctac aacgaggctt ggagattcag   1860 caaccccgc ttactaagtt cccccttatta ttatagtgcc gcccccggt ccgcccctgc   1920 cgctgctgcc gctgcctatg accgccacta gttaccgcgg ggaccacatc aagcttcagg   1980
ccgacagctt cggcctccac atcgtccccg tctgacccca cccggagg agggaggacc   2040 gacgcgacgc gatgcctccc ggccaccgcc ccagcctcac cccatcccac gaccccgca   2100 acccttcaca tcaccccct cgaaggtcgg acaggacggg tggagccgtg ggcgggaccc   2160
tcaggcccgg gcccgccgcc cccagccccg cctgccgccc ctccccgcct gcctggactg   2220
cgcggcgccg tgagggggat tcggcccagc tcgtcccggc ctccaccaag ccagccccga   2280
agcccgccag ccaccctgcc ggactcgggc gcgacctgct ggcgcgcgcc ggatgtttct   2340
gtgacacaca atcagcgcgg accgcagcgc ggcccagccc cggcacccg ctcggacgc   2400 tcgggcgcca ggaggcttcg ctggaggggc tgggccaagg agattaagaa gaaaacgact   2460
ttctgcagga ggaagagccc gctgccgaat ccctgggaaa aattcttttc ccccagtgcc   2520
agccggactg ccctcgcctt ccgggtgtgc cctgtcccag aagatggaat gggggtgtgg   2580
gggtccggct ctaggaacgg gctttggggg cgtcaggtct ttccaaggtt gggacccaag   2640 gatcggggg cccagcagcc cgcaccgatc gagccggact ctcggctctt cactgctcct   2700
cctggcctgc ctagttcccc agggcccggc acctcctgct gcgagacccg gctctcagcc   2760
ctgccttgcc cctacctcag cgtctcttcc acctgctggc ctcccagttt ccctcctgc   2820 cagtccttcg cctgtccctt gacgccctgc atcctcctcc ctgactcgca gccccatcgg   2880
acgtctcccc gggaccgccg caggaccagt ttccatagac tgcggactgg ggtcttcctc   2940
cagcagttac ttgatgcccc ctcccccgac acagactctc aatctgccgg tggtaagaac   3000
```

```
cggttctgag ctggcgtctg agctgctgcg gggtggaagt gggggggctgc ccactccact    3060 cctcccatcc cctcccagcc tcctcctccg gcaggaactg aacagaacca caaaaagtct    3120
acatttattt aatatgatgg tctttgcaaa aaggaacaaa acaacacaaa agcccaccag    3180
gctgctgctt tgtggaaaga cggtgtgtgt cgtgtgaagg cgaaacccgg tgtacataac    3240
ccctccccct ccgccccgcc ccgcccggcc ccgtagagtc cctgtcgccc gccggccctg    3300
cctgtagata cgccccgctg tctgtgctgt gagagtcgcc gctcgctggg ggggaagggg    3360
gggacacagc tacacgccca ttaaagcaca gcacgtcctg ggggagggg gcatttttta    3420 tgttacaaaa aaaaattacg aaagaaaaga aatctctatg caaaatgacg aacatggtcc    3480
tgtggactcc tctggcctgt tttgttggct cttctctgt aattccgtgt tttcgcttt     3540 tcctccctgc ccctctctcc ctctgcccct ctctcctctc cgcttctctc ccctctgtc    3600 tctgtctctc tccgtctctg tcgctcttgt ctgtctgtct ctgctctttc ctcggcctct    3660
ctccccagac ctggccggc cgccctgtct ccgcaggcta gatccgaggt ggcagctcca    3720 gccccgggc tcgccccctc gcgggcgtgc cccgcgcgcc ccgggcggcc gaaggccggg    3780 ccgcccgtc ccgcccgta gttgctcttt cggtagtggc gatgcgccct gcatgtctcc    3840
tcacccgtgg atcgtgacga ctcgaaataa cagaaacaaa gtcaataaag tgaaaataaa    3900
taaaaatcct tgaacaaatc cgaaaaggct tggagtcctc gcccagatct ctctcccctg    3960 cgagccctt ttatttgaga aggaaaaaga gaaaagagaa tcgtttaagg gaacccggcg     4020
cccagccagg ctccagtggc ccgaacgggg cggcgagggc ggcgagggcg ccgaggtccg    4080
gcccatccca gtcctgtggg gctggccggg cagagacccc ggacccaggc ccaggcctaa    4140
cctgctaaat gtccccggac ggttctggtc tcctcggcca ctttcagtgc gtcggttcgt    4200
tttgattctt tttcttttgt gcacataaga aataaataat aataataaat aaagaataaa    4260
attttgtatg tcaaaaaaaa aaaaaaaaa                                       4290
```

<210> SEQ ID NO 47
<211> LENGTH: 408
<212> TYPE: PRT
<213> ORGANISM: Homo sapiens

<400> SEQUENCE: 47

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140
```

```
Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
            165                 170                 175

Ala Ser Asn Asp Pro Val Gly Ser Tyr Ser Ile Asn Gly Ile Leu Gly
        180                 185                 190

Ile Pro Arg Ser Asn Gly Glu Lys Arg Lys Arg Asp Glu Asp Val Ser
    195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
                260                 265                 270

Leu Thr Pro Gly Leu Asp Glu Val Lys Ser Ser Leu Ser Ala Ser Thr
            275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
        355                 360                 365

Leu Met Pro Pro Pro Gly Pro Pro Leu Pro Leu Leu Pro Leu Pro Met
370                 375                 380

Thr Ala Thr Ser Tyr Arg Gly Asp His Ile Lys Leu Gln Ala Asp Ser
385                 390                 395                 400

Phe Gly Leu His Ile Val Pro Val
            405

<210> SEQ ID NO 48
<211> LENGTH: 4188
<212> TYPE: DNA
<213> ORGANISM: Homo sapiens

<400> SEQUENCE: 48
aggctccagt ctccggccga gtcttctcgc agccgcaacc cacctggggc cagcccagag      60
ctgccagcgc cgctcggctc cctccctccc tccggccct tcggccgcgg cggcgtgcgc     120
ctgccttttc cggggcggg ggcctggccc gcgcgctccc ctcccgcagg cgccacctcg     180
gacatccccg ggattgctac ttctctgcca acttcgccaa ctcgccagca cttggagagg    240
cccggctccc ctcccggcgc cctctgaccg ccccgccccc gcgcgctctc cgaccaccgc    300
ctctcggatg accaggttcc aggggagctg agcgagtcgc ctccccccgcc cagcttcagc   360 cctggctgca gctgcagcgc gagccatgcg ccccagtgc accccggccc ggccaccgc     420 cccggggcca ttctgctgac cgcccagccc cgagccccga cagtggcaag ttgcggctac    480
tgcagttgca agctccggcc aaccggagg agcccagcg gggagcgcag tgttgcgccc     540
cccgcccccg cgcgccccgc agcagccggg cgttcactca tcctccctcc cccaccgtcc    600
ctcccttttc tcctcaagtc ctgaagttga gtttgagagg cgacacggcg gcggcggccg   660
```

```
cgctgctccc gctcctctgc ctccccatgg atatgcactg caaagcagac cccttctccg    720
cgatgcaccc agggcacggg ggtgtgaacc agctcggggg ggtgtttgtg aacggccggc    780
ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg gcatctgtga caatgacaca gtgcccagcg   1080
tctcttccat caacagaatc atccggacca aagttcagca gcctttccac ccaacgccgg   1140
atggggctgg gacaggagtg accgcccctg gccacaccat tgttcccagc acggcctccc   1200
ctcctgtttc cagcgcctcc aatgacccag tgggatccta ctccatcaat gggatcctgg   1260
ggattcctcg ctccaatggt gagaagagga acgtgatga agatgtgtct gagggctcag   1320
tccccaatgg agattcccag agtggtgtgg acagtttgcg gaagcacttg cgagctgaca   1380
ccttcaccca gcagcagctg gaagctttgg atcgggtctt tgagcgtcct cctacccctg   1440
acgtcttcca ggcatcagag cacatcaaat cagaacaggg gaacgagtac tccctcccag   1500
ccctgacccc tgggcttgat gaagtcaagt cgagtctatc tgcatccacc aaccctgagc   1560
tgggcagcaa cgtgtcaggc acacagacat acccagttgt gactggtcgt gacatggcga   1620
gcaccactct gcctggttac cccctcacgt gcccccac tggccaggga agctacccca   1680
cctccaccct ggcaggaatg gtgcctggga gcgagttctc cggcaacccg tacagccacc   1740
cccagtacac ggcctacaac gaggcttgga gattcagcaa ccccgcctta ctaatgccgc   1800
cccccggtcc gccctgccg ctgctgccgc tgcctatgac cgccactagt taccgcgggg   1860
accacatcaa gcttcaggcc gacagcttcg gcctccacat cgtccccgtc tgaccccacc   1920
ccggagggag ggaggaccga cgcgacgcga tgcctcccgg ccaccgcccc agcctcaccc   1980
catcccacga ccccgcaac ccttcacatc acccccctcg aaggtcggac aggacgggtg   2040
gagccgtggg cgggaccctc aggccgggc ccgccgcccc cagccccgcc tgccgccct    2100
ccccgcctgc ctggactgcg cggcgccgtg agggggattc ggcccagctc gtcccggcct   2160
ccaccaagcc agccccgaag cccgccagcc accctgccgg actcgggcgc gacctgctgg   2220
cgcgcgccgg atgtttctgt gacacacaat cagcgcggac cgcagcgcgg cccagccccg   2280
ggcacccgcc tcggacgctc gggcgccagg aggcttcgct ggaggggctg ggccaaggag   2340
attaagaaga aaacgacttt ctgcaggagg aagagcccgc tgccgaatcc ctgggaaaaa   2400
ttcttttccc ccagtgccag ccggactgcc ctcgccttcc gggtgtgccc tgtcccagaa   2460
gatggaatgg gggtgtgggg gtccggctct aggaacgggc tttgggggcg tcaggtcttt   2520
ccaaggttgg gacccaagga tcgggggcc cagcagcccg caccgatcga gccggactct   2580
cggctcttca ctgctcctcc tggcctgcct agttccccag ggcccggcac ctcctgctgc   2640
gagacccggc tctcagccct gccttgcccc tacctcagcg tctcttccac ctgctggcct   2700
cccagttcc cctcctgcca gtccttcgcc tgtcccttga cgccctgcat cctcctccct   2760
gactcgcagc cccatcggac gctctcccgg gaccgccgca ggaccagttt ccatagactg   2820
cggactgggg tcttcctcca gcagttactt gatgcccct cccccgacac agactctcaa   2880
tctgccggtg gtaagaaccg gttctgagct ggcgtctgag ctgctgcggg gtggaagtgg   2940
ggggctgccc actccactcc tcccatcccc tcccagcctc ctcctccggc aggaactgaa   3000
cagaaccaca aaaagtctac atttatttaa tatgatggtc tttgcaaaaa ggaacaaaac   3060
```

```
aacacaaaag cccaccaggc tgctgctttg tggaaagacg gtgtgtgtcg tgtgaaggcg   3120
aaacccggtg tacataaccc ctcccctcc gccccgcccc gccggcccc gtagagtccc    3180 tgtcgcccgc cggccctgcc tgtagatacg ccccgctgtc tgtgctgtga gagtcgccgc   3240
tcgctggggg ggaaggggg gacacagcta cacgcccatt aaagcacagc acgtcctggg   3300
ggaggggggc attttttatg ttacaaaaaa aaattacgaa agaaaagaaa tctctatgca   3360
aaatgacgaa catggtcctg tggactcctc tggcctgttt tgttggctct ttctctgtaa   3420
ttccgtgttt tcgcttttc ctccctgcc ctctctccct ctgccctct ctcctctccg    3480 cttctctccc cctctgtctc tgtctctctc cgtctctgtc gctcttgtct gtctgtctct   3540
gctctttcct cggcctctct ccccagacct ggcccggccg ccctgtctcc gcaggctaga   3600
tccgaggtgg cagctccagc ccccgggctc gcccctcgc gggcgtgccc cgcgcgcccc   3660
gggcggccga aggccgggcc gccccgtccc gccccgtagt tgctctttcg gtagtggcga   3720
tgcgccctgc atgtctcctc acccgtggat cgtgacgact cgaaataaca gaaacaaagt   3780
caataaagtg aaaataaata aaaatccttg aacaaatccg aaaaggcttg gagtcctcgc   3840
ccagatctct ctcccctgcg agccttttt atttgagaag gaaaaagaga aaagagaatc   3900
gtttaaggga acccggcgcc cagccaggct ccagtggccc gaacggggcg gcgagggcgg   3960
cgagggcgcc gaggtccggc ccatcccagt cctgtgggc tggccgggca gagacccgg    4020 acccaggccc aggcctaacc tgctaaatgt ccccggacgg ttctggtctc ctcggccact   4080
ttcagtgcgt cggttcgttt tgattctttt tcttttgtgc acataagaaa taaataataa   4140
taataaataa agaataaaat tttgtatgtc aaaaaaaaaa aaaaaaa              4188
```

<210> SEQ ID NO 49
<211> LENGTH: 431
<212> TYPE: PRT
<213> ORGANISM: Homo sapiens

<400> SEQUENCE: 49

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
        50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175
```

-continued

```
Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Val Glu Val
            195                 200                 205

Tyr Thr Asp Pro Ala His Ile Arg Gly Gly Gly Leu His Leu Val
            210                 215                 220

Trp Thr Leu Arg Asp Val Ser Glu Gly Ser Val Pro Asn Gly Asp Ser
225                 230                 235                 240

Gln Ser Gly Val Asp Ser Leu Arg Lys His Leu Arg Ala Asp Thr Phe
                245                 250                 255

Thr Gln Gln Gln Leu Glu Ala Leu Asp Arg Val Phe Glu Arg Pro Ser
            260                 265                 270

Tyr Pro Asp Val Phe Gln Ala Ser Glu His Ile Lys Ser Glu Gln Gly
            275                 280                 285

Asn Glu Tyr Ser Leu Pro Ala Leu Thr Pro Gly Leu Asp Glu Val Lys
            290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
                325                 330                 335

Thr Leu Pro Gly Tyr Pro Pro His Val Pro Pro Thr Gly Gln Gly Ser
            340                 345                 350

Tyr Pro Thr Ser Thr Leu Ala Gly Met Val Pro Gly Ser Glu Phe Ser
            355                 360                 365

Gly Asn Pro Tyr Ser His Pro Gln Tyr Thr Ala Tyr Asn Glu Ala Trp
            370                 375                 380

Arg Phe Ser Asn Pro Ala Leu Leu Met Pro Pro Gly Pro Pro Leu
385                 390                 395                 400

Pro Leu Leu Pro Leu Pro Met Thr Ala Thr Ser Tyr Arg Gly Asp His
            405                 410                 415

Ile Lys Leu Gln Ala Asp Ser Phe Gly Leu His Ile Val Pro Val
            420                 425                 430
```

<210> SEQ ID NO 50
<211> LENGTH: 4257
<212> TYPE: DNA
<213> ORGANISM: Homo sapiens

<400> SEQUENCE: 50

| | | |
|---|---|---|
| aggctccagt ctccggccga gtcttctcgc agccgcaacc cacctggggc cagcccagag | 60 |
| ctgccagcgc cgctcggctc cctccctccc tccggccct tcggccgcgg cggcgtgcgc | 120 |
| ctgccttttc cggggcggg ggcctggccc gcgcgctccc ctcccgcagg cgccacctcg | 180 |
| gacatccccg ggattgctac ttctctgcca acttcgccaa ctcgccagca cttggagagg | 240 |
| cccggctccc ctcccggcgc cctctgaccg ccccgcccc gcgcgctctc cgaccaccgc | 300 |
| ctctcggatg accaggttcc aggggagctg agcgagtcgc ctcccccgcc cagcttcagc | 360 |
| cctggctgca gctgcagcgc gagccatgcg ccccagtgc accccggccc ggcccaccgc | 420 |
| cccggggcca ttctgctgac cgcccagccc cgagccccga cagtggcaag ttgcggctac | 480 |
| tgcagttgca agctccggcc aaccggagg agcccagcg gggagcgcag tgttgcgccc | 540 |
| cccgccccg cgcgccccgc agcagccggg cgttcactca tcctccctcc ccaccgtcc | 600 |
| ctccctttc tcctcaagtc ctgaagttga gtttgagagg cgacacgcg cggcggccg | 660 |
| cgctgctccc gctcctctgc ctccccatgg atatgcactg caaagcagac cccttctccg | 720 |

```
cgatgcaccc agggcacggg ggtgtgaacc agctcggggg ggtgtttgtg aacggccggc    780
ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg gcatctgtga caatgacaca gtgcccagcg   1080
tctcttccat caacagaatc atccggacca aagttcagca gcctttccac ccaacgccgg   1140
atggggctgg gacaggagtg accgcccctg gccacaccat tgttcccagc acggcctccc   1200
ctcctgtttc cagcgcctcc aatgacccag tgggatccta ctccatcaat gggatcctgg   1260
ggattcctcg ctccaatggt gagaagagga aacgtgatga agttgaggta tacactgatc   1320
ctgcccacat tagaggaggt ggaggtttgc atctggtctg gactttaaga gatgtgtctg   1380
agggctcagt ccccaatgga gattcccaga gtggtgtgga cagtttgcgg aagcacttgc   1440
gagctgacac cttcacccag cagcagctgg aagctttgga tcgggtcttt gagcgtcctt   1500
cctaccctga cgtcttccag gcatcagagc acatcaaatc agaacagggg aacgagtact   1560
ccctcccagc cctgaccccct gggcttgatg aagtcaagtc gagtctatct gcatccacca   1620
accctgagct gggcagcaac gtgtcaggca cacagacata cccagttgtg actggtcgtg   1680
acatggcgag caccactctg cctggttacc cccctcacgt gccccccact ggccagggaa   1740
gctaccccac ctcacccctg gcaggaatgg tgcctgggag cgagttctcc ggcaacccgt   1800
acagccaccc ccagtacacg gcctacaacg aggcttggag attcagcaac cccgccttac   1860
taatgccgcc ccccggtccg cccctgccgc tgctgccgct gcctatgacc gccactagtt   1920
accgcgggga ccacatcaag cttcaggccg acagcttcgg cctccacatc gtccccgtct   1980
gaccccaccc cggagggagg gaggaccgac gcgacgcgat gcctcccggc caccgcccca   2040
gcctcacccc atcccacgac ccccgcaacc cttcacatca ccccccctcga aggtcggaca   2100
ggacgggtgg agccgtgggc gggaccctca ggcccgggcc cgccgccccc agccccgcct   2160
gccgcccctc cccgcctgcc tggactgcgc ggcgccgtga gggggattcg gcccagctcg   2220
tcccggcctc caccaagcca gccccgaagc ccgccagcca ccctgccgga ctcgggcgcg   2280
acctgctggc gcgcgccgga tgtttctgtg acacacaatc agcgcggacc gcagcgcggc   2340
ccagccccgg gcacccgcct cggacgctcg ggcgccagga ggcttcgctg gaggggctgg   2400
gccaaggaga ttaagaagaa aacgactttc tgcaggagga gagcccgct gccgaatccc   2460
tgggaaaaat tcttttcccc cagtgccagc cggactgccc tcgccttccg ggtgtgccct   2520
gtcccagaag atggaatggg ggtgtggggg tccggctcta ggaacgggct ttggggcgt    2580
caggtctttc caaggttggg acccaaggat cgggggccc agcagcccgc accgatcgag    2640
ccggactctc ggctcttcac tgctcctcct ggcctgccta gttccccagg gcccggcacc    2700
tcctgctgcg agacccggct ctcagccctg ccttgcccct acctcagcgt ctcttccacc    2760
tgctggcctc ccagtttccc ctcctgccag tccttcgcct gtcccttgac gccctgcatc    2820
ctcctccctg actcgcagcc ccatcggacg ctctcccggg accgccgcag gaccagtttc    2880
catagactgc ggactggggt cttcctccag cagttacttg atgccccctc ccccgacaca    2940
gactctcaat ctgccggtgg taagaaccgg ttctgagctg gcgtctgagc tgctgcgggg    3000
tggaagtggg gggctgccca ctccactcct cccatcccct cccagcctcc tcctccggca    3060
ggaactgaac agaaccacaa aaagtctaca tttatttaat atgatggtct ttgcaaaaag    3120
```

```
gaacaaaaca acacaaaagc ccaccaggct gctgctttgt ggaaagacgg tgtgtgtcgt    3180
gtgaaggcga aacccggtgt acataacccc tccccctccg ccccgccccg ccggccccg     3240 tagagtccct gtcgcccgcc ggccctgcct gtagatacgc cccgctgtct gtgctgtgag    3300
agtcgccgct cgctgggggg aaggggggga acacagctac acgcccatta aagcacagca    3360
cgtcctgggg gagggggggca ttttttatgt tacaaaaaaa aattacgaaa gaaaagaaat   3420
ctctatgcaa aatgacgaac atggtcctgt ggactcctct ggcctgtttt gttggctctt    3480
tctctgtaat tccgtgtttt cgcttttttcc tccctgcccc tctctccctc tgcccctctc   3540
tcctctccgc ttctctccccc ctctgtctct gtctctctcc gtctctgtcg ctcttgtctg   3600
tctgtctctg ctctttcctc ggcctctctc cccagacctg gccggccgc cctgtctccg     3660 caggctagat ccgaggtggc agctccagcc cccgggctcg cccctcgcg ggcgtgcccc     3720 gcgcgccccg ggcggccgaa ggccgggccg cccgtcccg ccccgtagtt gctctttcgg     3780
tagtggcgat gcgccctgca tgtctcctca cccgtggatc gtgacgactc gaaataacag    3840
aaacaaagtc aataaagtga aaataaataa aaatccttga acaaatccga aaaggcttgg    3900
agtcctcgcc cagatctctc tccctgcga gcccttttta tttgagaagg aaaaagagaa     3960
aagagaatcg tttaagggaa cccggcgccc agccaggctc cagtggcccg aacggggcgg    4020
cgagggcggc gagggcgccg aggtccggcc catcccagtc ctgtggggct ggccgggcag    4080
agaccccgga cccaggccca ggcctaacct gctaaatgtc cccggacggt tctggtctcc    4140
tcggccactt tcagtgcgtc ggttcgtttt gattcttttt cttttgtgca cataagaaat    4200
aaataataat aataaataaa gaataaaatt ttgtatgtca aaaaaaaaa aaaaaaa       4257
```

<210> SEQ ID NO 51
<211> LENGTH: 18
<212> TYPE: DNA
<213> ORGANISM: Homo sapiens

<400> SEQUENCE: 51
cctggcaccc agcacaat                                                    18

<210> SEQ ID NO 52
<211> LENGTH: 20
<212> TYPE: DNA
<213> ORGANISM: Homo sapiens

<400> SEQUENCE: 52
gccgatccac acggagtact                                                  20

<210> SEQ ID NO 53
<211> LENGTH: 32
<212> TYPE: DNA
<213> ORGANISM: Homo sapiens

<400> SEQUENCE: 53
gttgcctgcc agtcgccatg agaacttcct ac                                    32

<210> SEQ ID NO 54
<211> LENGTH: 32
<212> TYPE: DNA
<213> ORGANISM: Homo sapiens

<400> SEQUENCE: 54
tggccttccc tctgtaacag gtgccttgaa tt                                    32

<210> SEQ ID NO 55

```
<211> LENGTH: 24
<212> TYPE: DNA
<213> ORGANISM: Homo sapiens

<400> SEQUENCE: 55
ccacccatgg caaattccat ggca                                          24

<210> SEQ ID NO 56
<211> LENGTH: 24
<212> TYPE: DNA
<213> ORGANISM: Homo sapiens

<400> SEQUENCE: 56
tctagacggc aggtcaggtc aacc                                          24

<210> SEQ ID NO 57
<211> LENGTH: 23
<212> TYPE: DNA
<213> ORGANISM: Homo sapiens

<400> SEQUENCE: 57
ctcaggccta tgcaaaaaga gga                                           23

<210> SEQ ID NO 58
<211> LENGTH: 20
<212> TYPE: DNA
<213> ORGANISM: Homo sapiens

<400> SEQUENCE: 58
gccctccctc caaaggagac                                               20

<210> SEQ ID NO 59
<211> LENGTH: 23
<212> TYPE: DNA
<213> ORGANISM: Homo sapiens

<400> SEQUENCE: 59
aacctacgca cctacgtgag gag                                           23

<210> SEQ ID NO 60
<211> LENGTH: 22
<212> TYPE: DNA
<213> ORGANISM: Homo sapiens

<400> SEQUENCE: 60
cgttcagtcc atcccatttc tg                                            22

<210> SEQ ID NO 61
<211> LENGTH: 20
<212> TYPE: DNA
<213> ORGANISM: Homo sapiens

<400> SEQUENCE: 61
gacacctgag ctgaccttgg                                               20

<210> SEQ ID NO 62
<211> LENGTH: 20
<212> TYPE: DNA
<213> ORGANISM: Homo sapiens

<400> SEQUENCE: 62
gaggaagtcc agtgtccagc                                               20

<210> SEQ ID NO 63
```

```
<211> LENGTH: 68
<212> TYPE: PRT
<213> ORGANISM: Homo sapiens

<400> SEQUENCE: 63

Met Arg Thr Ser Tyr Leu Leu Leu Phe Thr Leu Cys Leu Leu Leu Ser
1               5                  10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 64
<211> LENGTH: 914
<212> TYPE: DNA
<213> ORGANISM: Homo sapiens
<220> FEATURE:
<221> NAME/KEY: misc_feature
<222> LOCATION: (1)..(914)
<223> OTHER INFORMATION: n= a, c, g, or t

<400> SEQUENCE: 64
ctgcagggtg ggcccaggct gggccnagac cctcaccctc caagggccac actggggct      60 cactttctga ggagtgccct ttggaaacgt cccaggaaca cgtctagtgg gaaaagagaa    120
aagttggtcc atcgaggaga gtgttctgca taaggggaga gatgagaagg tagccttggc    180
cagaggaaga aacttcatta caaccagctc tccttctsca agggaagagg gtgaagtttg    240
agtttgtctt gcaggaagac aatcaaacta agaggccaa caccagctta gagccgagcg    300
gccccctgct cagagcttcc ctgtggctct cctccatgtg atccagaagg agggactcca    360
gtgtgaactg cctgttccag aaaccccatc agaactgcct aacctagaaa accaaacagg    420
aggagctggc accagggctc caggctgaaa gctaaatcca gcggcagcca gatggagaca    480
atgtgccatg tgactgctga ctgctcaggg caaatgacac caggggttag cgattagaag    540
ttcacccttg actgtggcac ctcccttcag ttccgtcgac gaggttgtgc aatccaccag    600
tcttataaat acagtgacgc tccagcctct ggaagcctct gtcagctcag cctccaaagg    660
agccagcctc tccccagttc ctgaaatcct gagtgttgcc tgccagtcgc catgagaact    720
tcctaccttc tgctgtttac tctctgctta cttttgtctg agatggcctc aggtaagctc    780
tggtacctgc tagagtttcc catccccagg gctggggaca atgggctga tgtgagtctc      840 ggatggctgc ctccgtgtcc caagggacga ggaacaagca gcaggaaagc atcccgtggt    900
tgagtggcct gcag                                                      914

<210> SEQ ID NO 65
<211> LENGTH: 19
<212> TYPE: DNA
<213> ORGANISM: Homo sapiens

<400> SEQUENCE: 65
tcagcagtgg agggcaatg                                                  19

<210> SEQ ID NO 66
<211> LENGTH: 23
<212> TYPE: DNA
<213> ORGANISM: Homo sapiens
```

```
<400> SEQUENCE: 66
cctctgtaac aggtgccttg aat                                          23

<210> SEQ ID NO 67
<211> LENGTH: 21
<212> TYPE: DNA
<213> ORGANISM: Homo sapiens

<400> SEQUENCE: 67
acagcaaacc tcctcacagc c                                            21

<210> SEQ ID NO 68
<211> LENGTH: 20
<212> TYPE: DNA
<213> ORGANISM: Homo sapiens

<400> SEQUENCE: 68
tggagacgtg gcacctcttg                                              20

<210> SEQ ID NO 69
<211> LENGTH: 24
<212> TYPE: DNA
<213> ORGANISM: Homo sapiens

<400> SEQUENCE: 69
tatgataccc gggagatcgt gatc                                         24

<210> SEQ ID NO 70
<211> LENGTH: 24
<212> TYPE: DNA
<213> ORGANISM: Homo sapiens

<400> SEQUENCE: 70
gtgcagatgc cggttcaggt actc                                         24

<210> SEQ ID NO 71
<211> LENGTH: 20
<212> TYPE: DNA
<213> ORGANISM: Homo sapiens

<400> SEQUENCE: 71
tcagccctgg actacctgca                                              20

<210> SEQ ID NO 72
<211> LENGTH: 20
<212> TYPE: DNA
<213> ORGANISM: Homo sapiens

<400> SEQUENCE: 72
gaggtcccgg tacaccacgt                                              20

<210> SEQ ID NO 73
<211> LENGTH: 19
<212> TYPE: RNA
<213> ORGANISM: Homo sapiens

<400> SEQUENCE: 73
auagacucga cuugacuuc                                               19

<210> SEQ ID NO 74
<211> LENGTH: 17
<212> TYPE: RNA
<213> ORGANISM: Homo sapiens
```

```
<400> SEQUENCE: 74
cuucaucacg uuuccuc                                                      17

<210> SEQ ID NO 75
<211> LENGTH: 19
<212> TYPE: RNA
<213> ORGANISM: Homo sapiens

<400> SEQUENCE: 75
guauucagca aucuugucc                                                    19

<210> SEQ ID NO 76
<211> LENGTH: 19
<212> TYPE: RNA
<213> ORGANISM: Homo sapiens

<400> SEQUENCE: 76
gauuugaugu gcucugaug                                                    19

<210> SEQ ID NO 77
<211> LENGTH: 19
<212> TYPE: RNA
<213> ORGANISM: Homo sapiens

<400> SEQUENCE: 77
gucgagucua ucugcaucc                                                    19

<210> SEQ ID NO 78
<211> LENGTH: 20
<212> TYPE: RNA
<213> ORGANISM: Homo sapiens

<400> SEQUENCE: 78
augugucagg cacacagacg                                                   20

<210> SEQ ID NO 79
<211> LENGTH: 9
<212> TYPE: PRT
<213> ORGANISM: Artificial Sequence
<220> FEATURE:
<223> OTHER INFORMATION: HIV TAT 48-60

<400> SEQUENCE: 79

Arg Lys Lys Arg Arg Gln Arg Arg Arg
1               5

<210> SEQ ID NO 80
<211> LENGTH: 13
<212> TYPE: PRT
<213> ORGANISM: Artificial Sequence
<220> FEATURE:
<223> OTHER INFORMATION: HIV TAT 48-60 peptide

<400> SEQUENCE: 80

Gly Arg Lys Lys Arg Arg Gln Arg Arg Arg Pro Pro Gln
1               5                   10

<210> SEQ ID NO 81
<211> LENGTH: 14
<212> TYPE: PRT
<213> ORGANISM: Artificial Sequence
<220> FEATURE:
<223> OTHER INFORMATION: TDSP5 peptide

<400> SEQUENCE: 81
```

```
Val Ser Arg Arg Arg Arg Arg Gly Gly Arg Arg Arg Arg
1               5                   10
```

```
<210> SEQ ID NO 82
<211> LENGTH: 21
<212> TYPE: PRT
<213> ORGANISM: Artificial Sequence
<220> FEATURE:
<223> OTHER INFORMATION: PEP-1 peptide (Chariot)

<400> SEQUENCE: 82
```

```
Lys Glu Thr Trp Trp Glu Thr Trp Trp Thr Glu Trp Ser Gln Pro Lys
1               5                   10                  15

Lys Lys Arg Lys Val
            20
```

```
<210> SEQ ID NO 83
<211> LENGTH: 16
<212> TYPE: PRT
<213> ORGANISM: Artificial Sequence
<220> FEATURE:
<223> OTHER INFORMATION: Antp 43-58 peptide

<400> SEQUENCE: 83
```

```
Arg Gln Ile Lys Ile Trp Phe Gln Asn Arg Arg Met Lys Trp Lys Lys
1               5                   10                  15
```

```
<210> SEQ ID NO 84
<211> LENGTH: 27
<212> TYPE: PRT
<213> ORGANISM: Artificial Sequence
<220> FEATURE:
<223> OTHER INFORMATION: HIV Gp41-SV40 NLS peptide

<400> SEQUENCE: 84
```

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25
```

```
<210> SEQ ID NO 85
<211> LENGTH: 18
<212> TYPE: PRT
<213> ORGANISM: Artificial Sequence
<220> FEATURE:
<223> OTHER INFORMATION: SAP peptide

<400> SEQUENCE: 85
```

```
Val Arg Leu Pro Pro Pro Val Arg Leu Pro Pro Pro Val Arg Leu Pro
1               5                   10                  15

Pro Pro
```

```
<210> SEQ ID NO 86
<211> LENGTH: 9
<212> TYPE: PRT
<213> ORGANISM: Artificial Sequence
<220> FEATURE:
<223> OTHER INFORMATION: MPG R9 peptide

<400> SEQUENCE: 86
```

```
Arg Arg Arg Arg Arg Arg Arg Arg Arg
1               5
```

```
<210> SEQ ID NO 87
<211> LENGTH: 18
```

```
<212> TYPE: PRT
<213> ORGANISM: Artificial Sequence
<220> FEATURE:
<223> OTHER INFORMATION: MAP peptide

<400> SEQUENCE: 87

Lys Leu Ala Leu Lys Leu Ala Leu Lys Ala Leu Lys Ala Ala Leu Lys
1               5                   10                  15

Leu Ala

<210> SEQ ID NO 88
<211> LENGTH: 12
<212> TYPE: PRT
<213> ORGANISM: Artificial Sequence
<220> FEATURE:
<223> OTHER INFORMATION: synthetic peptide

<400> SEQUENCE: 88

Lys Ala Leu Ala Lys Ala Leu Ala Lys Ala Leu Ala
1               5                   10

<210> SEQ ID NO 89
<211> LENGTH: 16
<212> TYPE: PRT
<213> ORGANISM: Artificial Sequence
<220> FEATURE:
<223> OTHER INFORMATION: K-FGF peptide

<400> SEQUENCE: 89

Ala Ala Val Ala Leu Leu Pro Ala Val Leu Leu Ala Leu Leu Ala Pro
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Penetratin peptide

<400> SEQUENCE: 90

Arg Gln Ile Lys Ile Trp Phe Gln Asn Arg Arg Met Lys Trp Lys Lys
1               5                   10                  15

<210> SEQ ID NO 91
<211> LENGTH: 21
<212> TYPE: PRT
<213> ORGANISM: Artificial Sequence
<220> FEATURE:
<223> OTHER INFORMATION: Buforin II peptide

<400> SEQUENCE: 91

Thr Arg Ser Ser Arg Ala Gly Leu Gln Phe Pro Val Gly Arg Val His
1               5                   10                  15

Arg Leu Leu Arg Lys
            20

<210> SEQ ID NO 92
<211> LENGTH: 26
<212> TYPE: PRT
<213> ORGANISM: Artificial Sequence
<220> FEATURE:
<223> OTHER INFORMATION: Transportan peptide

<400> SEQUENCE: 92

Gly Trp Thr Leu Asn Ser Ala Gly Tyr Leu Leu Gly Lys Ile Asn Lys
1               5                   10                  15
```

```
Ala Leu Ala Ala Leu Ala Lys Lys Ile Leu
            20                  25

<210> SEQ ID NO 93
<211> LENGTH: 5
<212> TYPE: PRT
<213> ORGANISM: Artificial Sequence
<220> FEATURE:
<223> OTHER INFORMATION: Ku70 peptide

<400> SEQUENCE: 93

Val Pro Met Leu Lys
1               5

<210> SEQ ID NO 94
<211> LENGTH: 28
<212> TYPE: PRT
<213> ORGANISM: Artificial Sequence
<220> FEATURE:
<223> OTHER INFORMATION: Prion peptide

<400> SEQUENCE: 94

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 95
<211> LENGTH: 19
<212> TYPE: PRT
<213> ORGANISM: Artificial Sequence
<220> FEATURE:
<223> OTHER INFORMATION: pVEC peptide

<400> SEQUENCE: 95

Leu Leu Ile Ile Ile Leu Arg Arg Arg Ile Arg Lys Gln Ala His Ala
1               5                   10                  15

His Ser Lys

<210> SEQ ID NO 96
<211> LENGTH: 15
<212> TYPE: PRT
<213> ORGANISM: Artificial Sequence
<220> FEATURE:
<223> OTHER INFORMATION: Pep-7 peptide

<400> SEQUENCE: 96

Ser Asp Leu Trp Glu Met Met Met Val Ser Leu Ala Cys Gln Tyr
1               5                   10                  15

<210> SEQ ID NO 97
<211> LENGTH: 12
<212> TYPE: PRT
<213> ORGANISM: Artificial Sequence
<220> FEATURE:
<223> OTHER INFORMATION: HN-1 peptide

<400> SEQUENCE: 97

Thr Ser Pro Leu Asn Ile His Asn Gly Gln Lys Leu
1               5                   10

<210> SEQ ID NO 98
<211> LENGTH: 26
<212> TYPE: PRT
<213> ORGANISM: Artificial Sequence
<220> FEATURE:
<223> OTHER INFORMATION: CP26 peptide
```

<400> SEQUENCE: 98

Lys Trp Lys Ser Phe Ile Lys Lys Leu Thr Ser Ala Ala Lys Lys Val
1               5                   10                  15

Val Thr Thr Ala Lys Pro Leu Ile Ser Ser
            20                  25

<210> SEQ ID NO 99
<211> LENGTH: 333
<212> TYPE: PRT
<213> ORGANISM: Homo sapiens

<400> SEQUENCE: 99

Met Glu Glu Asn Asp Pro Lys Pro Gly Glu Ala Ala Ala Val Glu
1               5                   10                  15

Gly Gln Arg Gln Pro Glu Ser Ser Pro Gly Gly Ser Gly Gly
            20                  25                  30

Gly Gly Ser Ser Pro Gly Glu Ala Asp Thr Gly Arg Arg Ala Leu
            35                  40                  45

Met Leu Pro Ala Val Leu Gln Ala Pro Gly Asn His Gln His Pro His
50                  55                  60

Arg Ile Thr Asn Phe Phe Ile Asp Asn Ile Leu Arg Pro Glu Phe Gly
65                  70                  75                  80

Arg Arg Lys Asp Ala Gly Thr Cys Cys Ala Gly Ala Gly Gly Gly Arg
                85                  90                  95

Gly Gly Gly Ala Gly Gly Glu Gly Gly Ala Ser Gly Ala Glu Gly Gly
            100                 105                 110

Gly Gly Ala Gly Gly Ser Glu Gln Leu Leu Gly Ser Gly Ser Arg Glu
            115                 120                 125

Pro Arg Gln Asn Pro Pro Cys Ala Pro Gly Ala Gly Gly Pro Leu Pro
130                 135                 140

Ala Ala Gly Ser Asp Ser Pro Gly Asp Gly Glu Gly Gly Ser Lys Thr
145                 150                 155                 160

Leu Ser Leu His Gly Gly Ala Lys Lys Gly Gly Asp Pro Gly Gly Pro
                165                 170                 175

Leu Asp Gly Ser Leu Lys Ala Arg Gly Leu Gly Gly Gly Asp Leu Ser
            180                 185                 190

Val Ser Ser Asp Ser Asp Ser Gln Ala Gly Ala Asn Leu Gly Ala
            195                 200                 205

Gln Pro Met Leu Trp Pro Ala Trp Val Tyr Cys Thr Arg Tyr Ser Asp
210                 215                 220

Arg Pro Ser Ser Gly Pro Arg Ser Arg Lys Pro Lys Lys Asn Pro
225                 230                 235                 240

Asn Lys Glu Asp Lys Arg Pro Arg Thr Ala Phe Thr Ala Glu Gln Leu
                245                 250                 255

Gln Arg Leu Lys Ala Glu Phe Gln Thr Asn Arg Tyr Leu Thr Glu Gln
            260                 265                 270

Arg Arg Gln Ser Leu Ala Gln Glu Leu Ser Leu Asn Glu Ser Gln Ile
            275                 280                 285

Lys Ile Trp Phe Gln Asn Lys Arg Ala Lys Ile Lys Lys Ala Thr Gly
290                 295                 300

Asn Lys Asn Thr Leu Ala Val His Leu Met Ala Gln Gly Leu Tyr Asn
305                 310                 315                 320

His Ser Thr Thr Ala Lys Glu Gly Lys Ser Asp Ser Glu
                325                 330

<210> SEQ ID NO 100
<211> LENGTH: 3405
<212> TYPE: DNA
<213> ORGANISM: Homo sapiens

<400> SEQUENCE: 100

| | | | | | | |
|---|---|---|---|---|---|---|
| tctctcatcg | tctgggcgag | cggggcggct | cgtggtgttt | ctaacccagt | tcgtggattc | 60 |
| aaaggtggct | ccgcgccgag | cgcggccggc | gacttgtagg | acctcagccc | tggccgcggc | 120 |
| cgccgcgcac | gccctcggaa | gactcggcgg | ggtgggggcg | cggggtctc | cgtgtgcgcc | 180 |
| gcgggagggc | cgaaggctga | tttggaaggg | cgtccccgga | gaaccagtgt | gggatttact | 240 |
| gtgaacagca | tggaggagaa | tgacccaag | cctggcgaag | cagcggcggc | ggtggaggga | 300 |
| cagcggcagc | cggaatccag | ccccggcggc | ggctcgggcg | gcgcggcgg | tagcagcccg | 360 |
| ggcgaagcgg | acaccgggcg | ccggcgggct | ctgatgctgc | ccgcggtcct | gcaggcgccc | 420 |
| ggcaaccacc | agcacccgca | ccgcatcacc | aacttcttca | tcgacaacat | cctgcggccc | 480 |
| gagttcggcc | ggcgaaagga | cgcggggacc | tgctgtgcgg | gcgcgggagg | aggaaggggc | 540 |
| ggcggagccg | gcggcgaagg | cggcgcgagc | ggtgcggagg | gaggcggcgg | cgcgggcggc | 600 |
| tcggagcagc | tcttgggctc | gggctcccga | gagccccggc | agaacccgcc | atgtgcgccc | 660 |
| ggcgcgggcg | ggccgctccc | agccgccggc | agcgactctc | cgggtgacgg | ggaaggcggc | 720 |
| tccaagacgc | tctcgctgca | cggtggcgcc | aagaaaggcg | gcgaccccgg | cggcccctg | 780 |
| gacgggtcgc | tcaaggcccg | cggcttgggc | ggcggcgacc | tgtcggtgag | ctcggactcg | 840 |
| gacagctcgc | aagccggcgc | caacctgggc | gcgcagccca | tgctctggcc | ggcgtgggtc | 900 |
| tactgtacgc | gctactcgga | ccggccttct | tcaggtccca | ggtctcgaaa | accaaagaag | 960 |
| aagaacccga | acaaagagga | caagcggccg | cgcacggcct | ttaccgccga | gcagctgcag | 1020 |
| aggctcaagg | ccgagttcca | gaccaacagg | tacctgacgg | agcagcggcg | ccagagcctg | 1080 |
| gcgcaggagc | tgagcctcaa | cgagtcacag | atcaagattt | ggttccagaa | caagcgcgcc | 1140 |
| aagatcaaga | aggccacggg | caacaagaac | acgctggccg | tgcacctcat | ggcacagggc | 1200 |
| ttgtacaacc | actccaccac | agccaaggag | ggcaagtcgg | acagcgagta | gggcgggggg | 1260 |
| catggaggcc | aggtctcagt | ccgcgctaaa | caatgcaata | atttaaaatc | ataagggcc | 1320 |
| agtgtataaa | gattatacca | gcattaatag | tgaaaatatt | gtgtattagc | taaggttctg | 1380 |
| aaatattcta | tgtatatatc | atttacaggt | ggtataaaat | ccaaatatc | tgactataaa | 1440 |
| atattttttt | gagtttttg | tgtttatgag | attatgctaa | ttttatgggt | tttttcttt | 1500 |
| tttgcgaagg | gggctgctta | gggtttcacc | ttttttaat | ccctaagct | ccattatatg | 1560 |
| acattggaca | ctttttatt | attccaaaag | aagaaaaaat | taaacaact | tgctgaagtc | 1620 |
| caaagatttt | ttattgctgc | atttcacaca | actgtgaacc | gaataaatag | ctcctatttg | 1680 |
| gtctatgact | tctgccactt | tgtttgtgtt | ggcttggtga | ggacagcagg | aggggcccac | 1740 |
| acctcaagcc | tggaccagcc | acctcaaggc | cttggggagc | ttaggggacc | tggtgggaga | 1800 |
| gaggggactt | ccagggtcct | tgggccagtt | ctgggatttg | gccctgggaa | gcagcccagc | 1860 |
| gtaccccagg | cctgctctgg | gaagtcggct | ccatgctcac | cagcagccgc | ccaggccgc | 1920 |
| agcctcaccc | ggctccctct | cctcacccctc | ctgcacctaa | ctcccctcctc | cttctccttt | 1980 |
| ttcctcctct | tcctccttcc | tccttcctcc | tgctcctcct | ttcttcttct | ttttcttctc | 2040 |
| ctcctcctcc | ttccttcctc | ctcctccttc | tctttcctcc | tcctcctcac | caagggccca | 2100 |
| accgtgtgca | tacatcgtct | gcgtctgtgg | tctgtgtcgc | tgtccccagt | cccaccgcag | 2160 |

-continued

```
tcctgccgca ggcctaaccc tcctgccctg ggcactgcct ccatgcagaa gcgcttcgag    2220
gttctggggc taaaggcctg gggtgtgtgg cctaaagccc aagagcggtg gggcgaccct    2280 cctttttggct tggccccagg aatttcctgt gactccacca gccatcatgg gtgccagcca   2340
gggtcccaga aatgaggcca tggctcactg tttctgggcg ggcagaaggc tctgtagagg    2400
gagatggcat catctatctt cctttccttt ttcttttctt ccctattttt ttcttttttt    2460
cctttatttt tttcttttct tggagtggct gcttctgcta tagagaacat tcttccaaga   2520
taaatatgtg tgtttacaca tatgtctgca tgcatgtgaa cacacacaca cacacacaca   2580
caccaggcgt gtttgagtcc acagttctga aacatgtggc taccttgtct ttcaaaagaa   2640
ctcagaatcc tccaggatct agaagaagga agaaagtgtg taaataatca tttcttatca   2700 tcacttttg tcttttcttg ttttttaaaa tatacatttt attttgaag gtgtggtaca     2760 gtgtaaatta aatatattca atatatttcc caccaagtac ctatatatgt atataaacaa   2820
acacattatc tatatataac gccacactgt cttctgttta gtgtatgggg aaagaccaat   2880
ccaactgtcc atctgtggct gggacagccc aggggtgtg cccacggctg acccaggggt    2940
gtgcacacgg ctgagctggg agtcccgctg gtctccctga ggactgaggg tgaacttcgc   3000
tctttgcctt aaacctcttt atttcattgc agtaatagtt ttacgttgta cataatagtg   3060 taaaccttt taaaaggaa agtataaaaa caaaagttgt aatttaaaag tctgaataac     3120
catctgctgc ttaggaaact caatgaaatg acatgccttt ttagcaggaa gcaaagttgg   3180
tttctgtttt ttgttttctt tgttgtttta gtttataaaa catgtgcatt ttacagttcc   3240
agtatcaaat atttataatc ttatgagaaa tgaatgaatg tttctattta caactgtgct   3300
tatcaaaatt gtgaacaccc ccaccccgc atttttgtgt gttgaaattc ttgaaggtta    3360
cattaaataa aacaaaatct ctttattata aaataaaaaa aaaaa                   3405
```

<210> SEQ ID NO 101
<211> LENGTH: 9
<212> TYPE: DNA
<213> ORGANISM: Homo sapiens

<400> SEQUENCE: 101 acccttgac                                                                 9

<210> SEQ ID NO 102
<211> LENGTH: 13
<212> TYPE: DNA
<213> ORGANISM: Homo sapiens

<400> SEQUENCE: 102
tcacccttga ctg                                                           13

<210> SEQ ID NO 103
<211> LENGTH: 17
<212> TYPE: DNA
<213> ORGANISM: Homo sapiens

<400> SEQUENCE: 103 gttcacccctt gactgtg                                                      17

<210> SEQ ID NO 104
<211> LENGTH: 29
<212> TYPE: DNA
<213> ORGANISM: Homo sapiens

<400> SEQUENCE: 104

```
gcgattagaa gttcaccctt gactgtggc                                         29

<210> SEQ ID NO 105
<211> LENGTH: 33
<212> TYPE: DNA
<213> ORGANISM: Homo sapiens

<400> SEQUENCE: 105
gcgattagaa gttcaccctt gactgtggca cct                                    33

<210> SEQ ID NO 106
<211> LENGTH: 19
<212> TYPE: DNA
<213> ORGANISM: Homo sapiens

<400> SEQUENCE: 106
tcaacgagtc acagatcaa                                                    19

<210> SEQ ID NO 107
<211> LENGTH: 19
<212> TYPE: RNA
<213> ORGANISM: artificial
<220> FEATURE:
<223> OTHER INFORMATION: sense siRNA

<400> SEQUENCE: 107
ucaacgaguc acagaucaa                                                    19

<210> SEQ ID NO 108
<211> LENGTH: 19
<212> TYPE: RNA
<213> ORGANISM: artificial
<220> FEATURE:
<223> OTHER INFORMATION: antisense siRNA

<400> SEQUENCE: 108
uugaucugug acucguuga                                                    19

<210> SEQ ID NO 109
<211> LENGTH: 19
<212> TYPE: DNA
<213> ORGANISM: Homo sapiens

<400> SEQUENCE: 109
ccaacttctt catcgacaa                                                    19

<210> SEQ ID NO 110
<211> LENGTH: 19
<212> TYPE: RNA
<213> ORGANISM: artificial
<220> FEATURE:
<223> OTHER INFORMATION: sense siRNA

<400> SEQUENCE: 110
ccaacuucuu caucgacaa                                                    19

<210> SEQ ID NO 111
<211> LENGTH: 19
<212> TYPE: RNA
<213> ORGANISM: artificial
<220> FEATURE:
<223> OTHER INFORMATION: antisense siRNA

<400> SEQUENCE: 111
uugucgauga agaaguugg                                                    19
```

```
<210> SEQ ID NO 112
<211> LENGTH: 19
<212> TYPE: DNA
<213> ORGANISM: Homo sapiens

<400> SEQUENCE: 112
ctcgaaaacc aaagaagaa                                                      19

<210> SEQ ID NO 113
<211> LENGTH: 19
<212> TYPE: RNA
<213> ORGANISM: artificial
<220> FEATURE:
<223> OTHER INFORMATION: sense siRNA

<400> SEQUENCE: 113
cucgaaaacc aaagaagaa                                                      19

<210> SEQ ID NO 114
<211> LENGTH: 19
<212> TYPE: RNA
<213> ORGANISM: artificial
<220> FEATURE:
<223> OTHER INFORMATION: antisense siRNA

<400> SEQUENCE: 114
uucuucuuug guuuucgag                                                      19

<210> SEQ ID NO 115
<211> LENGTH: 22
<212> TYPE: DNA
<213> ORGANISM: artificial
<220> FEATURE:
<223> OTHER INFORMATION: forward primer

<400> SEQUENCE: 115
gttcgtggat tcaaaggtgg ct                                                  22

<210> SEQ ID NO 116
<211> LENGTH: 22
<212> TYPE: DNA
<213> ORGANISM: artificial
<220> FEATURE:
<223> OTHER INFORMATION: reverse primer

<400> SEQUENCE: 116
taaatcccac actggttctc cg                                                  22

<210> SEQ ID NO 117
<211> LENGTH: 104
<212> TYPE: DNA
<213> ORGANISM: Homo sapiens

<400> SEQUENCE: 117
ttcacccttg actgtggcac ctcccttcag ttccgtcgac gaggttgtgc aatccaccag         60
tcttataaat acagtgacgc tccagcctct ggaagcctct gtca                         104
```